(12) United States Patent
Song et al.

(10) Patent No.: US 11,485,782 B2
(45) Date of Patent: Nov. 1, 2022

(54) ANTI-CLAUDIN 18.2 ANTIBODIES

(71) Applicant: Beijing Xuanyi PharmaSciences Co., Ltd., Beijing (CN)

(72) Inventors: Yuntao Song, Palo Alto, CA (US); Yi Ding, Milpitas, CA (US); Chen Dong, Cupertino, CA (US); Zhiwei Li, West Sacramento, CA (US); John Lippincott, San Mateo, CA (US); Ping Hui Szu, Walnut Creek, CA (US)

(73) Assignee: Beijing Xuanyi Pharmasciences Co., Ltd., Beijing (CN)

( * ) Notice: Subject to any disclaimer, the term of this patent is extended or adjusted under 35 U.S.C. 154(b) by 123 days.

(21) Appl. No.: 16/980,294

(22) PCT Filed: Mar. 14, 2019

(86) PCT No.: PCT/CN2019/078150
§ 371 (c)(1),
(2) Date: Sep. 11, 2020

(87) PCT Pub. No.: WO2019/174617
PCT Pub. Date: Sep. 19, 2019

(65) Prior Publication Data
US 2021/0009686 A1     Jan. 14, 2021

Related U.S. Application Data

(60) Provisional application No. 62/803,297, filed on Feb. 8, 2019, provisional application No. 62/643,035, filed on Mar. 14, 2018.

(51) Int. Cl.
| | | |
|---|---|---|
| *C07K 16/28* | (2006.01) | |
| *A61P 35/00* | (2006.01) | |
| *A61K 39/395* | (2006.01) | |
| *A61K 39/00* | (2006.01) | |
| *G01N 33/68* | (2006.01) | |
| *A61K 45/06* | (2006.01) | |

(52) U.S. Cl.
CPC ........ *C07K 16/28* (2013.01); *A61K 39/39558* (2013.01); *A61K 45/06* (2013.01); *A61P 35/00* (2018.01); *G01N 33/68* (2013.01); *A61K 2039/505* (2013.01); *C07K 2317/31* (2013.01); *C07K 2317/33* (2013.01); *C07K 2317/56* (2013.01); *G01N 2333/705* (2013.01)

(58) Field of Classification Search
CPC ............... C07K 16/28; C07K 2317/31; C07K 2317/33; C07K 2317/56; A61P 35/00; A61K 39/39558; A61K 45/06; A61K 2039/505; G01N 33/68; G01N 2333/705
See application file for complete search history.

(56) References Cited

U.S. PATENT DOCUMENTS

| | | |
|---|---|---|
| 4,179,337 A | 12/1979 | Davis |
| 4,301,144 A | 11/1981 | Iwashita |
| RE30,985 E | 6/1982 | Cartaya |
| 4,485,045 A | 11/1984 | Regen |
| 4,496,689 A | 1/1985 | Mitra |
| 4,544,545 A | 10/1985 | Ryan |
| 4,560,655 A | 12/1985 | Baker |
| 4,640,835 A | 2/1987 | Shimizu |
| 4,657,866 A | 4/1987 | Kumar |
| 4,670,417 A | 6/1987 | Iwasaki |
| 4,676,980 A | 6/1987 | Segal |
| 4,767,704 A | 8/1988 | Cleveland et al. |
| 4,791,192 A | 12/1988 | Nakagawa |
| 4,816,567 A | 3/1989 | Cabilly |
| 4,927,762 A | 5/1990 | Darfler |
| 4,933,294 A | 6/1990 | Waterfield |
| 4,994,560 A | 2/1991 | Kruper, Jr. |
| 5,013,556 A | 5/1991 | Woodle |
| 5,122,469 A | 6/1992 | Mather |
| 5,199,942 A | 4/1993 | Gillis |
| 5,274,119 A | 12/1993 | Frazier |
| 5,342,604 A | 8/1994 | Wilson |
| 5,399,346 A | 3/1995 | Anderson |
| 5,401,638 A | 3/1995 | Carney |
| 5,428,139 A | 6/1995 | Kiefer |
| 5,435,990 A | 7/1995 | Cheng |

(Continued)

FOREIGN PATENT DOCUMENTS

| | | |
|---|---|---|
| EP | 3263702 A1 | 1/2018 |
| JP | 6232646 B2 | 11/2017 |

(Continued)

OTHER PUBLICATIONS

Almagro, J. et al., (Jan. 1, 2008). "Humanization of Antibodies," Frontiers in Bioscience 13:1619-1633.
Baca, M. et al. (Apr. 18, 1997). "Antibody Humanization Using Monovalent Phage Display," J. Biol. Chem. 272(16):10678-10684.
Barnes, D. et al. (Mar. 1, 1980). "Methods for Growth of Cultured Cells In Serum-Free Medium," Anal. Biochem. 102(2):255-270.
Boerner, P. et al. (Jul. 1, 1991). "Production of a Antigen-Specific Human Monoclonal Antibodies from In Vitro-Primed Human Splenocytes," J. Immunol. 147(1):86-95.
Brennan, M. et al. (Jul. 5, 1985). "Preparation of Bispecific Antibodies by Chemical Recombination of Monoclonal Immunoglobulin G1 Fragments," Science 229:81-83.

(Continued)

*Primary Examiner* — Misook Yu
*Assistant Examiner* — Dennis J Sullivan
(74) *Attorney, Agent, or Firm* — Morrison & Foerster LLP

(57) ABSTRACT

Provided are anti-claudin 18.2 (CLDN18.2) antibodies and fragments thereof. Also provided are isolated nucleic acid molecules that encode anti-CLDN18.2 antibodies, vectors comprising such nucleic acid, and host cells comprising such vectors or nucleic acids. Provided are methods of making anti-CLDN18.2. Also provided are related pharmaceutical compositions and methods using such pharmaceutical compositions in the treatment of disorders associated with aberrant CLDN18.2 expression, such as cancers.

16 Claims, 9 Drawing Sheets

Specification includes a Sequence Listing.

(56) References Cited

U.S. PATENT DOCUMENTS

| | | |
|---|---|---|
| 5,489,425 A | 2/1996 | Kruper, Jr. |
| 5,505,931 A | 4/1996 | Pribish |
| 5,545,806 A | 8/1996 | Lonberg et al. |
| 5,545,807 A | 8/1996 | Surani |
| 5,569,825 A | 10/1996 | Lonberg |
| 5,571,894 A | 11/1996 | Wels |
| 5,580,859 A | 12/1996 | Felgner |
| 5,587,458 A | 12/1996 | King |
| 5,589,466 A | 12/1996 | Felgner |
| 5,625,126 A | 4/1997 | Lonberg |
| 5,633,425 A | 5/1997 | Lonberg et al. |
| 5,641,870 A | 6/1997 | Rinderknecht |
| 5,652,361 A | 7/1997 | Simon |
| 5,661,016 A | 8/1997 | Lonberg et al. |
| 5,696,239 A | 12/1997 | Wilson |
| 5,714,631 A | 2/1998 | Wilson |
| 5,731,168 A | 3/1998 | Carter |
| 5,756,065 A | 5/1998 | Wilson |
| 5,808,003 A | 9/1998 | Subramanian |
| 5,869,046 A | 2/1999 | Presta |
| 6,075,181 A | 6/2000 | Kucherlapati |
| 6,143,559 A | 11/2000 | Michael |
| 6,150,584 A | 11/2000 | Kucherlapati |
| 6,248,516 B1 | 6/2001 | Winter |
| 6,326,193 B1 | 12/2001 | Liu |
| 6,602,684 B1 | 8/2003 | Umana |
| 7,332,581 B2 | 2/2008 | Presta |
| 7,521,541 B2 | 4/2009 | Eigenbrot |
| 8,313,913 B2 | 11/2012 | Nakamura |
| 8,592,644 B2 | 11/2013 | Harriman |
| 9,380,769 B2 | 7/2016 | Leighton |
| 11,111,295 B2 * | 9/2021 | Wang .................. A61K 39/395 |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2005/0031613 A1 | 2/2005 | Nakamura |
| 2005/0123546 A1 | 6/2005 | Umana |
| 2007/0134759 A1 | 6/2007 | Nishiya |
| 2008/0241884 A1 | 10/2008 | Shitara |
| 2015/0147763 A1 | 5/2015 | Sahin et al. |

FOREIGN PATENT DOCUMENTS

| | | |
|---|---|---|
| WO | 1987000195 A1 | 1/1987 |
| WO | 1990003430 A1 | 4/1990 |
| WO | 1991005264 A1 | 4/1991 |
| WO | 1991010741 A1 | 7/1991 |
| WO | 1993016185 A2 | 8/1993 |
| WO | 1994004690 A1 | 3/1994 |
| WO | 1994011026 A2 | 5/1994 |
| WO | 1996033735 A1 | 10/1996 |
| WO | 1996034096 A1 | 10/1996 |
| WO | 1997030087 A1 | 8/1997 |
| WO | 1998024893 A2 | 6/1998 |
| WO | 1998058964 A1 | 12/1998 |
| WO | 1999022764 A1 | 5/1999 |
| WO | 2000042072 A2 | 7/2000 |
| WO | 2000061739 A1 | 10/2000 |
| WO | 2001029058 A1 | 4/2001 |
| WO | 2001029246 A1 | 4/2001 |
| WO | 2001096584 A2 | 12/2001 |
| WO | 2003011878 A2 | 2/2003 |
| WO | 2003084570 A1 | 10/2003 |
| WO | 2003085107 A1 | 10/2003 |
| WO | 2002031140 A1 | 2/2004 |
| WO | 2004056312 A2 | 7/2004 |
| WO | 2005014653 A2 | 2/2005 |
| WO | 2005035586 A1 | 4/2005 |
| WO | 2005035778 A1 | 4/2005 |
| WO | 2005053742 A1 | 6/2005 |
| WO | 2003085119 A1 | 8/2005 |
| WO | 2008077546 A1 | 7/2008 |
| WO | 2008145338 A2 | 12/2008 |
| WO | 2011019844 A1 | 2/2011 |
| WO | 2012162422 A2 | 11/2012 |
| WO | 2013059159 A1 | 4/2013 |
| WO | 2013174404 A1 | 11/2013 |
| WO | 2016166122 A1 | 10/2016 |
| WO | 2019174617 A1 | 9/2019 |

OTHER PUBLICATIONS

Brüggemann, M. et al. (1993). "Designer Mice: The Production of Human Antibody Repertoires in Transgenic Animals," Year in Immuno. 7:33-40.

Caron, P.C. et al. (Oct. 1, 1992). "Engineering Humanized Dimeric Forms of IgG are More Effective Antibodies," J. Exp Med. 176:1191-1195.

Carter, P. et al. (Feb. 1992). "High Level *Escherichia coli* Expression and Production of a Bivalent Humanized Antibody Fragment," Bio/Technology 10:163-167.

Carter, P. et al. (May 1992). "Humanization of an Anti-p185HER2 Antibody for Human Cancer Therapy," Proc. Natl. Acad. Sci. USA 89:4285-4289.

Chothia, C. et al. (Aug. 20, 1987). "Canonical Structures for the Hypervariable Regions of Immunoglobulins," J. Mol. Biol. 196(4):901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Cunningham, B.C. et al. (Jun. 2, 1989). "High-Resolution Epitope Mapping of hGH-Receptor Interactions by Alanine-Scanning Mutagenesis," Science 244:1081-1085.

Daneschdar, M. et al. (Apr. 2014), "Rapid Mimotope Optimization for Pharmacokinetic Analysis of the Novel Therapeutic Antibody IMAB362," JPT Peptide Technologies 5(12489):1-2, 2 pages.

Eisenhauer, E.A. et al. (2009) "New Response Evaluation Criteria in Solid Tumors: Revised RECIST Guideline (version 1.1)." Eur. J. Cancer 45: 228-247.

Ellison, G. et al. (2013, e-pub. Nov. 20, 2012). "EGFR Mutation Testing In Lung Cancer: A Review of Available Methods and Their Use For Analysis of Tumour Tissue and Cytology Samples," J. Clin. Pathol. 66(2):79-89.

Epstein, D.A. et al. (Jun. 1985). "Biological Activity of Lipsome-Encapsulated Murine Interferon γ is Mediated by Cell Membrane Receptor," Proc. Natl. Acad. Sci. USA 82:3688-3692.

Evan, G.I. et al. (Dec. 1985). "Isolation of Monoclonal Antibodies Specific for Human c-myc Proto-Oncogene Product," Mol. Cell. Biol. 5(12):3610-3616.

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101 (34):12467-12472.

Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1,4-N-Acetylglucosaminyltransferase III and Golgi α-Mannosidase," Biotechnology and Bioengineering 93(5):851-861.

Field, J. et al. (May 1988), "Purification of a RAS-Responsive Adenylyl Cyclase Complex from *Saccharomyces cerevisiae* by Use of an Epitope Addition Method," Mol. Cell. Biol. 8(5):2159-2165.

Fishwild, D.M. et al. (Jul. 1996). "High-Avidity Human IgGK Monoclonal Antibodies from a Novel Strain of Minilocus Transgenic Mice," Nature Biotechnol. 14:845-851.

Gabizon, A. et al. (Oct. 4, 1989). "Pharmacokinetics and Issue Distribution of Doxorubicin Encapsulated in Stable Liposomes With Long Circulation Times," J. National Cancer Inst. 81(19)1484-1488.

(56) References Cited

OTHER PUBLICATIONS

Graham, F.L. et al. (1977). "Characteristics of a Human Cell Line Transforme by DNA From Human Adenovirus Type 5," Journal General Virology 36(1):59-74.
Griffiths, A.D. et al. (1993). "Human Anti-Self Antibodies with High Specificity from Phage Display Libraries," EMBO J. 12(2):725-734.
Gruber, M. et al. (1994). "Efficient Tumor Cell Lysis Mediated by a Bispecific Single Chain Antibody Expressed in *Escherichia coli*," J. Immunol. 152:5368-5374.
Guha, M. et al. (Jun. 21, 2013). "DISSECT Method Using PNA-LNA Clamp Improves Detection of EGFR T790m Mutation," PloS ONE 8(6):e67782, 5 pages.
Gupta, R. et al. (2009, e-pub, Nov. 7, 2008). "Evaluation of EGFR Abnormalities In Patients With Pulmonary Adenocarcinoma: The Need to Test Neoplasms With More Than One Method," Mod. Pathol. 22(1):128-133.
Ham, R.J. et al. (1979). "Media and Growth Requirements," Meth. Enz. 58:44-93.
Hamers-Casterman, C. et al. (Jun. 3, 1993). "Naturally Occurring Antibodies Devoid of Light Chains," Nature 363:446-448.
Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.
Harlow, E. et al. eds. (1988), "Using Antibodies: A Laboratory Manual," Cold Spring Harbor Laboratory Press, pp. iv-ix, (Table of Contents Only), 9 pages.
Holliger, P. et al. (Jul. 1993). "Diabodies": Small Bivalent and Bispecific Antibody Fragments, Proc. Natl. Acad. Sci. USA 90:6444-6448.
Hongo, J.A.S. et al. (1995). "Development and Characterization of Murine Monoclonal Antibodies to the Latency-Associated Peptide of Transforming Growth Factor Beta1," Hybridoma, 14(3):253-260.
Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.
Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.
Hopp, T.P. et al. (1988). "A Short Polypeptide Marker Sequence Useful for Recombinant Protein identification and Purification," BioTechnology 6:1204-1210.
Hudson, P.J. et al. (Jan. 2003). "Engineered Antibodies," Nat. Med. 9(1):129-134.
Hwang, K.J. et al. (Jul. 1980). "Hepatic Uptake and Degradation of Unilamellar Sphingomyelin/Cholesterol Liposomes: A Kinetic Study." Proc. Natl. Acad. Sci. USA 77:4030-4034.
International Search Report and Written Opinion of the International Searching Authority dated Jun. 17, 2019, for International Patent Application No. PCT/CN2019/078150, filed Mar. 27, 2019, 16 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.
Jalkanen, M. et al. (Dec. 1987). "Cell Surface Proteoglycan of Mouse Mammary Epithelial Cells is Shed by Cleavage of Its Matrix-Binding Ectodomain From Its Membrane-Associated Domain," J. Cell. Biol. 105(6):3087-3096.
Jalkanen, M. et al. (Sep. 1985). "Heparan Sulfate Proteoglycans From Mouse Mammary Epithelial Cells: Localization on The Cell Surface With a Monoclonal Antibody," J. Cell. Biol. 101:976-985.
Johnson, G. et al. (2003). "The Kabat Database and a Bioinformatics Example," Methods in Molecular Biology 248:11-25, 15 pages.
Jones, P.T. et al. (May 29, 1986). "Replacing the Complementarity-Determining Regions in a Human Antibody With Those From a Mouse," Nature 321:522-525.
Kanda, Y. et al. (2006, e-pub, Apr. 11, 2006), "Comparison of Cell Line for Stable Production of Fucose-Negative Antibodies with Enhanced ADCC," Biotechnol. Bioeng. 94(4):680-688.
Kohler, G. et al. (Aug. 7, 1975) "Continuous Cultures of Fused Cells Secreting Antibody of Predefined Specificity," Nature 256:495-497.
Kostelny, S.A. et al. (Mar. 1, 1992). "Formation of a Bispecific Antibody by The Use of Leucine Zippers," J. Immunol. 148(5):1547-1553.
Lee, C.V. et al. (2004). "Bivalent Antibody Phage Display Mimics Natural Immunoglobulin," .J. Immunol. Methods 284(1-2):119-132.
Lee, C.V. et al. (2004). "High-Affinity Human Antibodies From Phage-Displayed Synthetic Fab Libraries With a Single Framework Scaffold," J. Mol. Biol. 340:1073-1093.
Li, H. et al. (Feb. 2006, e-published on Jan. 22, 2006). "Optimization of Humanized IgGs in Glycoengineered Pichia Pastoris," Nature Biotechnology 24(2):210-215.
Lonberg, N. et al. (1995, e-pub. Jul. 10, 2009). "Human Antibodies From Transgenic Mice," Int. Rev. Immunol. 13(1):65-93.
Lonberg, N. et al. (2008, e-pub. Jul. 21, 2008). "Fully Human Antibodies From Transgenic Mouse and Phage Display Platforms," Curr. Opin. Immunol. 20:450-459.
Lonberg, N. et al. (Apr. 28, 1994). "Antigen-Specific Human Antibodies From Mice Comprising Four Distinct Genetic Modifications," Nature 368(6474):856-859.
Lopez-Rios, F. et al. (2013, e-pub, Feb. 5, 2013). "Comparison of Molecular Testing Methods for The Detection of EGFR Mutations In Formalin-Fixed Paraffin-Embedded Tissue Specimens of Non-Small Cell Lung Cancer," J. Clin. Pathol. 66(5):381-385.
Lutz-Freyermuth, C. et al. (Aug. 1990). "Quantitative Determination That One of Two Potential RNA-Binding Domains of the a Protein Component ofthe U1 Smail Nuclear Ribonucleoprotein Complex Binds with High Affinity to Stem-Loop II of U1 RNA," Proc. Natl. Acad. Sci. USA 87:6393-6397.
Marks, J.D. et al. (1991). "By-Passing Immunization Human Antibodies from V-gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
Martin, F.J. et al. (1982). "Irreversible Coupling of Immunoglobulin Fragments to Preformed Vesicles," J. Biol. Chem. 257(1):286-288.
Martin, G.A. el al. (Jan. 10, 1992), "GAP Domains Responsible for Ras P21-Dependent Inhibition of Muscarinic Atrial K+ Channel Currents," Science 255(5041):192-194.
Mather, J.P. et al. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals New York Academy of Sciences pp. 44-68.
Morimoto, K. et al. (1992). "Single-Step Purification of F(AB')2 Fragments of Mouse Monoclonal Antibodies (Immunoglobulins G1) by Hydrophobic Interaction High Performance Liquid Chromatography Using TSKgel Phenyl-5PW," J. Biochem. Biophys. Method 24:107-117.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Morrison, S.L. (Apr. 28, 1994) "Success in Specification," Nature 368: 812-813, 4 pages.
Neuberger, M. (Jul. 1996) "Generating High-Avidity Human Mabs in Mice," Nature Biotechnology 14:826, 1 page.
Okazaki, A. et al. (Mar. 5, 2004). "Fucose Depletion From Human IgG1 Oligosaccharide Enhances Binding Enthalpy and Association Rate Between IgGI and FcγRIIIa," J. Mol. Biol. 336(5):1239-1249.
Paborsky, L.R. et al. (1990). "Mammalian Cell Transient Expression of Tissue Factor for the Production of Antigen," Protein Eng. 3(6):547-553.

(56) References Cited

OTHER PUBLICATIONS

Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Presta, L.G. et al. (2002). "Engineering Therapeutic Antibodies for Improved Function," Biochemical Society Transactions 30(4):487-490.
Presta, L.G. et al. (Sep. 1, 1993). "Humanization of an Antibody Directed Against IgE," J. Immunol. 151(5):2623-2632.
Riechmann, L. et al. (Mar. 24, 1988). "Reshaping Human Antibodies for Therapy," Nature 332:323-329.
Ripka, J. et al. (Sep. 1986), "Two Chinese Hamster Ovary Glycosylation Mutants Affected in the Conversion of GDP-Mannose to GDP-Fucose," Arch Biochem Biophys. 249(2):533-545.
Rosenberg, S.A. et al. (Dec. 22, 1988). "Use of Tumor-Infiltrating Lymphocytes and Interleukin-2 in the Immunotherapy of Patients with Metastatic Melanoma—A preliminary Report," The New England Journal of Medicine 319:1676-1680.
Sahin, U. et al. (Dec. 1, 2008). "Claudin-18 Splice Variant 2 is a Pan-Cancer Target Suitable for Therapeutic Antibody Development," Clin Cancer Res 14(23):7624-7634.
Schwarze, S.R. et al. (Sep. 3, 1999). "In Vivo Protein Transduction: Delivery of a Biologically Active Protein into the Mouse," Science 285:1569-1572.
Sheriff, S. et al. (Sep. 1996). "Redefining the Minimal Antigen-Binding Fragment," Nature Struct. Biol. 3(9):733-736.
Shields, R.L. et al. (Mar. 2, 2001). "High Resolution Mapping of the Binding Site on Human IgGI for FcγRI, FcγRII, FcγRIII, and FcRn and Design of IgG1 Variants With Improved Binding to the FcγR," J. Biol.Chem. 276(9):6591-6604.
Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140:777-783.
Shopes, B. et al. (May 1, 1992). "A Genetically Engineered Human IgG Mutant With Enhanced Cytolytic Activity," J. Imniunol. 148:2918-2922.
Sias, P.E. et al. (1990). "ELISA for Quantitation of the Extracellular Domain of p185HER2 in Biological Fluids," J. Immunol. Methods 132:73-80.
Sidhu, S.S. et al. (2004). "Phage-Displayed Antibody Libraries of Synthetic Heavy Chain Complementarity Determining Regions," J. Mol. Biol. 338(2):299-310.
Sims, M.J. et al. (Aug. 15, 1993). "A Humanized CD18 Antibody can Block Function Without Cell Destruction," J. Immunol. 151:2296-2308.
Skinner, R.H. et al. (Aug. 5, 1991). "Use ofthe Glu-Glu-Phe C-Terminal Epitope for Rapid Purification of the Catalytic Domain of Normal and Mutant ras GTPase-Activating Proteins" J. Biol. Chem. 266(22):15163-15166.
Spiess, C. et al. (2015, e-pub. Jan. 27, 2015). "Alternative Molecular Formats and Therapeutic Applications for Bispecific Antibodies," Mol. Immunol. 67:95-106.
Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Torre, L.A. et al. (2015). "Global Cancer Statistics, 2012," CA Cancer J. Clin. 65(2):87-108.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Vitetta, E.S. et al. (Nov. 20, 1987). "Redesigning Nature's Poisons to Create Anti-Tumor Reagents," Science 238:1098-1104.
Vollmers, H.P. et al. (2005). "Death by Stress: Natural IgM-induced Apoptosis," Methods and Findings in Experimental and Clinical Pharmacology 27(3):185-191.
Vollmers, H.P. et al. (2005). "The 'Early Birds': Natural IgM Antibodies and Immune Surveillance," Histology and Histopathology, 20(3):927-937.
Winter, G. el al. (1994). "Making Antibodies by Phage Display Technology," Ann. Rev. Immunol. 12:433-455.
Wolff, E.A. et al. (Jun. 1, 1993). "Monoclonal Antibody Homodimers: Enhanced Antitumor Activity in Nude Mice," Can Res 53:2560-2565.
Wright, A. et al. (Jan. 1997). "Effect of Glycosylation on Antibody Function: Implications for Genetics Engineering," Trends Biotechnol. 15:26-32.
Yamane-Ohnuki, N. et al. (Sep. 5, 2004, e-pub Aug. 6, 2004). "Establishment of FUT8 Knockout Chinese Hamster Ovary Cells: An Ideal Host Cell Line for Producing Completely Defucosylated Antibodies With Enhanced Antibody-Dependent. Cellular Cytotoxicity," Biotechnology and Bioengineering 87(5):614-622.
Yazaki, P.J. et al. (2003). "Expression of Recombinant Antibodies in Mammalian Cell Lines," Methods in Molecular Biology, vol. 248 B.K.C. Lo, ed., Humana Press, Totowa, N.J. pp. 255-268.
Extended European Search Report and Search Opinion dated Apr. 20, 2022, for European Patent Application No. 19768583.7, filed on Jul. 22, 2020, 13 pages.
Singh, P. et al. (2017). "Anti-Claudin 18.2 Antibody as New Targeted Therapy for Advanced Gastric Cancer," Journal of Hematology & Oncology 10(105):1-5.

* cited by examiner

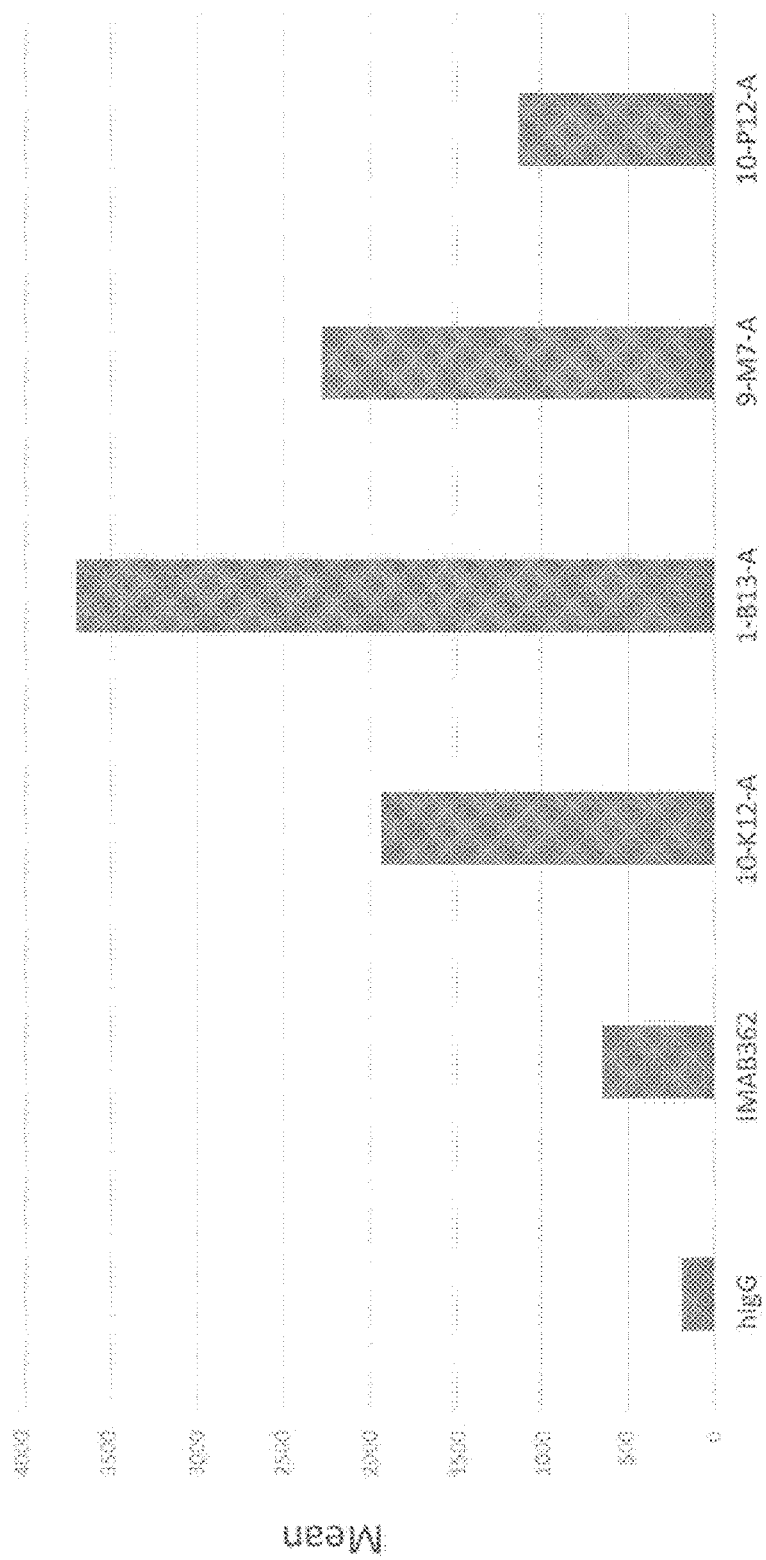

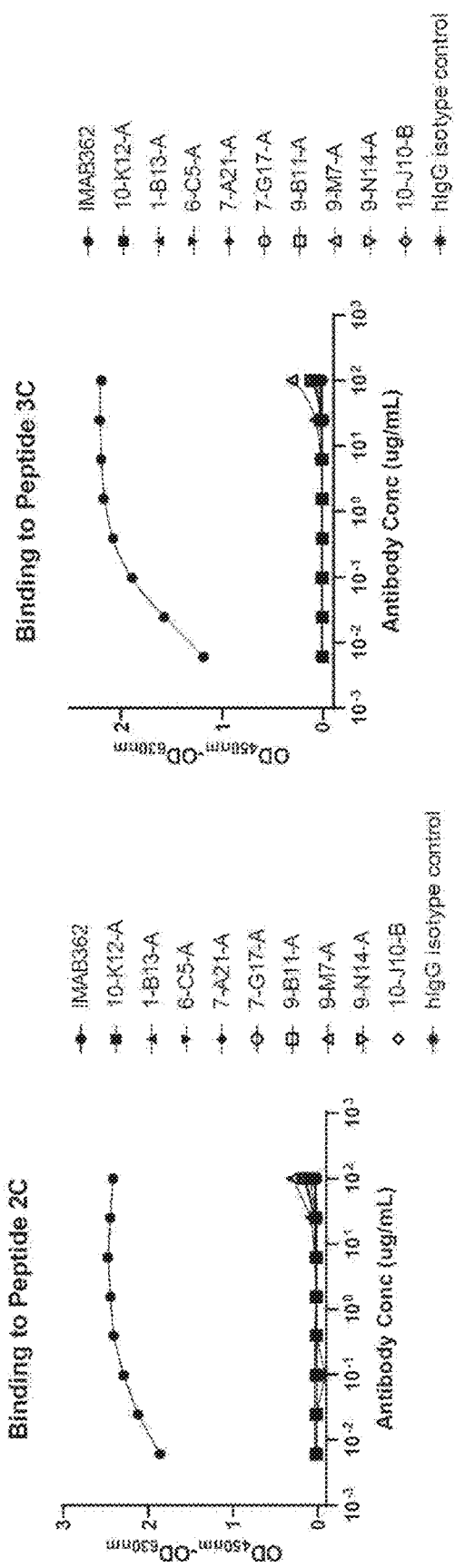

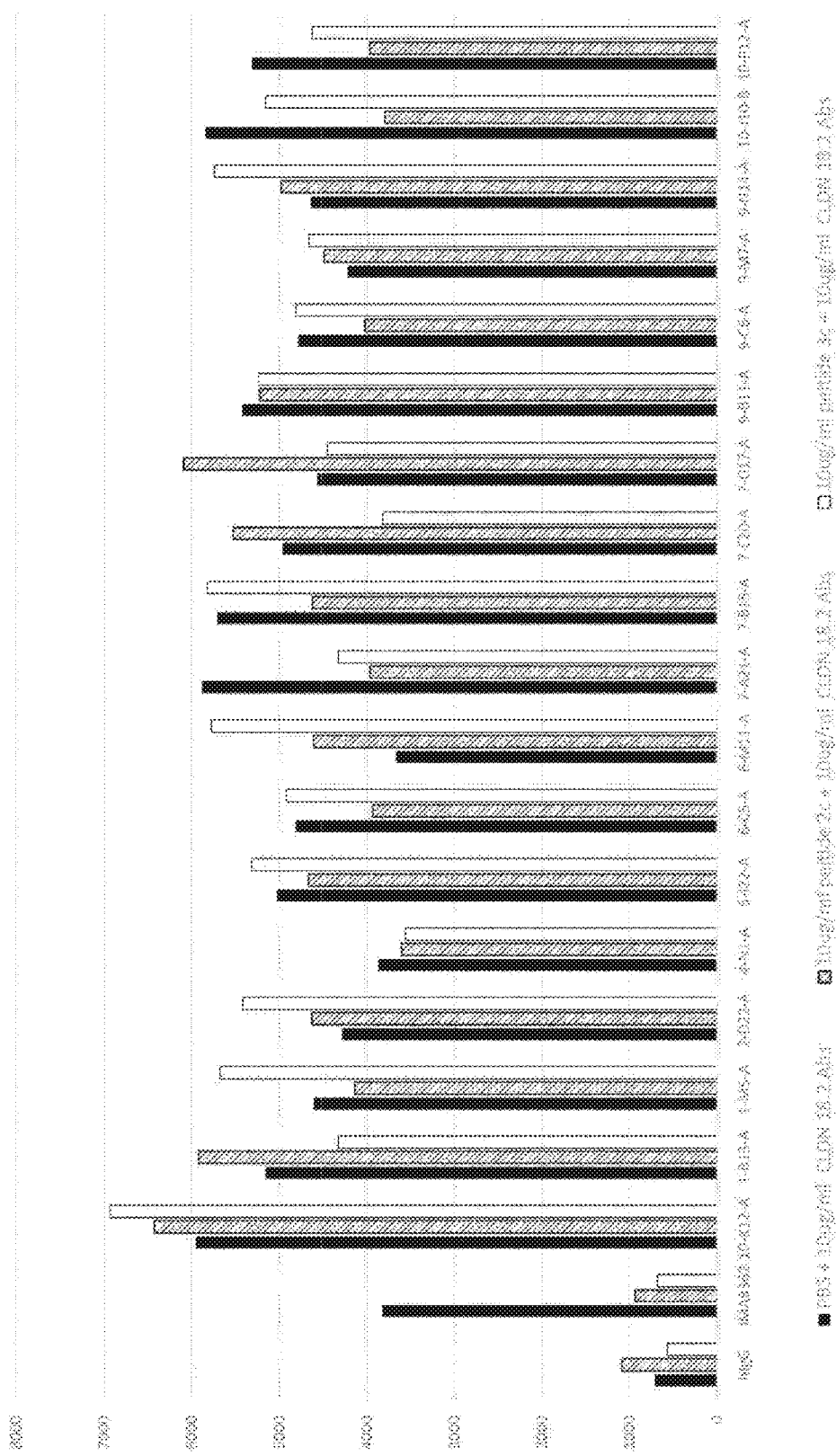

ANTI-CLAUDIN 18.2 ANTIBODIES

CROSS REFERENCE TO RELATED APPLICATIONS

This patent application is a national stage application under 35 U.S.C. § 371 of International Application No. PCT/CN2019/078150, filed internationally on Mar. 14, 2019, which claims priority to U.S. Provisional Application Ser. No. 62/643,035, filed Mar. 14, 2018, and U.S. Provisional Application Ser. No. 62/803,297, filed on Feb. 8, 2019, the contents of each of which are incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 776172000100SEQLIST.TXT date recorded: Sep. 9, 2020, size: 81 KB).

BACKGROUND OF THE INVENTION

Claudins are a family of tight junction membrane proteins that are expressed in epithelia and endothelia and form paracellular barriers and pores that determine tight junction permeability. Claudin 18 isotype 2 (CLDN18.2), a splice variant of the Claudin 18 protein, is a gastric lineage antigen that is expressed on short-lived differentiated gastric epithelial cells. The expression of CLDN18.2 is typically not detectable in other healthy human tissues. However, CLDN18.2 is ectopically expressed at significant levels in a variety of human cancers, including gastroesophageal and pancreatic cancer (Sahin et al. (2008) *Clin Cancer Res,* 14(23): 7624-34). CLDN18.2 is also frequently detected in metastases of gastric cancer.

Gastric cancer is one of the most common cancers worldwide, the fourth (in males) and fifth (in females) most common causes of cancer-related deaths in the developed world. An estimated 951,600 new stomach cancer cases and 723,100 deaths occurred in 2012 (Torre et al. (2015) *CA Cancer J. Clin.* 65(2): 87-108). The majority of patients with gastric cancer are often diagnosed in the advanced stage of the disease, and treatment typically entails palliative chemotherapy conferring a median survival time of 8-10 months. Accordingly, there is a need for antibody therapy directed against CLDN18.2-expressing cancer cells. The present invention meets this and other needs.

BRIEF SUMMARY OF THE INVENTION

Provided is an anti-CLDN18.2 antibody or antigen binding fragment, comprising: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9X_{10}X_{11}X_{12}X_{13}X_{14}KG$ (SEQ ID NO: 30), wherein $X_1$ is Y, E, T, H, or N; $X_2$ is S, N, D, Y, or I; $X_3$ is S, P, or I; $X_4$ is G, N, K, R, or Y; $X_5$ is S, N, G, or Y; $X_6$ is S, G, T, N, or D; $X_7$ is N, T, V, Y, I, or P; $X_8$ is I, T, or F; $X_9$ is Y, H, or N; $X_{10}$ is Y, or S; $X_{11}$ is A, N, P, T, or V; $X_{12}$ is D, Q, or E; $X_{13}$ is T, K, S, or R; and $X_{14}$ is V, F, M, or L; (c) a CDR-H3 comprising $X_1X_2X_3GNX_4X_5X_6Y$ (SEQ ID NO: 43), wherein: $X_1$ is I, F, P, A, Q, or H; $X_2$ is A, Y, V, T; $X_3$ is R or Y; $X_4$ is A, V, S, or T; $X_5$ is M, L, or F; and $X_6$ is D or A; (d) a CDR-L1 comprising $X_1SX_2QX_3LX_4NX_5X_6NX_7X_8NYLX_9$ (SEQ ID NO: 54), wherein: $X_1$ is K or R; $X_2$ is S or R; $X_3$ is S or I; $X_4$ is L or F; $X_5$ is S or T; $X_6$ is G or E; $X_7$ is Q or L; $X_8$ is K or R; $X_9$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QX_1X_2X_3X_4X_5PX_6X_7$ (SEQ ID NO: 71), wherein $X_1$ is N or D; $X_2$ is D, G, N, or A; $X_3$ is Y or F; $X_4$ is F, S, I, or Y; $X_5$ is Y or F; $X_6$ is L or F; and $X_7$ is T or P.

In some embodiments according to (or as applied to) any of the embodiments above, the anti-CLDN18.2 antibody or antigen binding fragment comprises (a) a CDR-H1 comprising an amino acid sequence set forth in any one of SEQ ID NOs: 1-6 and 8-10, (b) a CDR-H2 comprising an amino acid sequence forth in any one of SEQ ID NOs: 12-16 and 18-28, (c) a CDR-H3 comprising an amino acid sequence forth in any one of SEQ ID NOs: 31-42, (d) a CDR-L1 comprising an amino acid sequence set forth in any one of SEQ ID NOs: 44-47 and 49-52, (e) a CDR-L2 comprising an amino acid sequence set forth in any one of SEQ ID NOs: 55-57, and (f) a CDR-L3 comprising an amino acid sequence set forth in any one of SEQ ID NOs: 59-63 and 65-70. In some embodiments according to (or as applied to) any of the embodiments above, anti-CLDN18.2 antibody or antigen binding fragment thereof does not specifically bind CLDN18.1.

In some embodiments according to (or as applied to) any of the embodiments above, the anti-CLDN18.2 antibody or antigen binding fragment comprises a VH domain comprising (a) a CDR-H1 comprising GFTFSDYGMF (SEQ ID NO: 1), (b) a CDR-H2 comprising YISSGSSNIYYADTVKG (SEQ ID NO: 12), and (c) a CDR-H3 comprising IARGNAMDY (SEQ ID NO: 31) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYFYPLT (SEQ ID NO: 59). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YINSGSSTIYYADTVKG (SEQ ID NO: 13), and (c) a CDR-H3 comprising FARGNVLDY (SEQ ID NO: 32) and/or a VL domain comprising (d) a CDR-L1 comprising RSSQSLLNSGNQRNYLT (SEQ ID NO: 45), (e) a CDR-L2 comprising WASTRES (SEQ ID NO: 55), and (f) a CDR-L3 comprisingQNGYSYPLT (SEQ ID NO: 60). In some embodiments according to (or as applied to) any of the embodiments above, the anti-CLDN18.2 antibody or antigen binding fragment comprises a VH domain comprising (a) a CDR-H1 comprising GYSFTGYNIH (SEQ ID NO: 3), (b) a CDR-H2 comprising YIDPNNGVTYSNQKFKG (SEQ ID NO: 14), and (c) a CDR-H3 comprising PYYGNSFDY (SEQ ID NO: 33) and/or a VL domain comprising (d) a CDR-L1 comprising KSSQSLLNSGNLRNYLT (SEQ ID NO: 46), (e) a CDR-L2 comprising WASTRES (SEQ ID NO: 55), and (f) a CDR-L3 comprising QDGYFYPFP (SEQ ID NO: 61). In some embodiments according to (or as applied to) any of the embodiments above, the anti-CLDN18.2 antibody or antigen binding fragment comprises a VH domain comprising (a) a CDR-H1 comprising GYTFTVWSMS (SEQ ID NO: 4), (b) a CDR-H2 comprising EIYPKSGNTHYNEKFKG (SEQ ID NO: 15), and (c) a CDR-H3 comprising AYYGNSFAY (SEQ ID NO: 34) and/or a VL domain comprising (d) a CDR-L1 comprising KSSQSLLNSGNQRNYLT (SEQ ID NO: 47), (e) a CDR-L2 comprising WASTRES (SEQ ID NO: 55), and (f) a CDR-L3 comprising QNDFIYPFT (SEQ ID NO: 62). In some embodiments according to (or as applied to) any of the embodiments above, the anti-CLDN18.2 antibody or antigen binding fragment comprises a VH domain comprising (a) a CDR-H1 comprising GFTFSNNAMS (SEQ ID NO: 5), (b) a CDR-H2 comprising TIIIGGTYTYYPDSVKG (SEQ ID NO: 16), and (c) a CDR-H3 comprising QVYGNSFAY (SEQ ID NO: 35) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNNYFYPFT (SEQ ID NO: 63). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YISSGSSTIYYADTMKG (SEQ ID NO: 18), and (c) a CDR-H3 comprising FVRGNSMDY (SEQ ID NO: 36) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising HISSGSNIIHYADTLKG (SEQ ID NO: 19), and (c) a CDR-H3 comprising FARGNTMDY (SEQ ID NO: 37) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSFPLT (SEQ ID NO: 66). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YISSGSSTIYYADTMKG (SEQ ID NO: 18), and (c) a CDR-H3 comprising FARGNTMDY (SEQ ID NO: 37) and/or a VL domain comprising (d) a CDR-L1 comprising KSSQSLLNSGNQRNYLT (SEQ ID NO: 47), (e) a CDR-L2 comprising WASTRES (SEQ ID NO: 55), and (f) a CDR-L3 comprising QNGYSYPLT (SEQ ID NO: 60). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YISSGSNTFYYTDTVKG (SEQ ID NO: 20), and (c) a CDR-H3 comprising FTRGNALDY (SEQ ID NO: 38) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65). In some embodiments according to (or as applied to) any of the embodiments above, the anti-CLDN18.2 antibody or antigen binding fragment comprises a VH domain comprising (a) a CDR-H1 comprising GFTFSDYGMY (SEQ ID NO: 6), (b) a CDR-H2 comprising YISSGSNTIYYADTVKG (SEQ ID NO: 21), and (c) a CDR-H3 comprising IARGNAMDY (SEQ ID NO: 31) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYIYPLT (SEQ ID NO: 67). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising HISSGSSTIYYADTMKG (SEQ ID NO: 22), and (c) a CDR-H3 comprising FVRGNALDY (SEQ ID NO: 39) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNGYSYPLT (SEQ ID NO: 60). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YISSGSSTIHYVDTMKG (SEQ ID NO: 23), and (c) a CDR-H3 comprising FARGNTLDY (SEQ ID NO: 40) and/or a VL domain comprising (d) a CDR-L1 comprising KSSQSLFNTGNQKNYLT (SEQ ID NO: 49), (e) a CDR-L2 comprising WASTRES (SEQ ID NO: 55), and (f) a CDR-L3 comprising NGYSYPLT (SEQ ID NO: 60). In some embodiments according to (or as applied to) any of the embodiments above, the anti-CLDN18.2 antibody or antigen binding fragment comprises a VH domain comprising (a) a CDR-H1 comprising GFTFSDYGMY (SEQ ID NO: 6), (b) a CDR-H2 comprising YISSGSSTIYYADTVKG (SEQ ID NO: 24), and (c) a CDR-H3 comprising IARGNAMDY (SEQ ID NO: 31) and/or a VL domain comprising (d) a CDR-L1 comprising KSSQSLFNSGNQRNYLA (SEQ ID NO: 50), (e) a CDR-L2 comprising WASTRES (SEQ ID NO: 55), and (f) a CDR-L3 comprising QNDYFYPLT (SEQ ID NO: 59). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YISSGSSPIYYADTVKG (SEQ ID NO: 25), and (c) a CDR-H3 comprising FARGNAMDY (SEQ ID NO: 41) and/or a VL domain comprising (d) a CDR-L1 comprising KSSQSLLNSGNQKNYLT (SEQ ID NO: 44), (e) a CDR-L2 comprising WASTRDS (SEQ ID NO: 56), and (f) a CDR-L3 comprising QNNYYYPLT (SEQ ID NO: 68). In some embodiments according to (or as applied to) any of the embodiments above, the anti-CLDN18.2 antibody or antigen binding fragment comprises a VH domain comprising (a) a CDR-H1 comprising GFTFSDYGMH (SEQ ID NO: 2), (b) a CDR-H2 comprising YISSGSSTIYYADTMKG (SEQ ID NO: 18), and (c) a CDR-H3 comprising FVRGNSMDY (SEQ ID NO: 36) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65). In some embodiments according to (or as applied to) any of the embodiments above, the anti-CLDN18.2 antibody or antigen binding fragment comprises a VH domain comprising (a) a CDR-H1 comprising GFTFSNYAMS (SEQ ID NO: 8), (b) a CDR-H2 comprising TIIIGGTYTYYPDSVKG (SEQ ID NO: 16), and (c) a CDR-H3 comprising QVYGNSFAY (SEQ ID NO: 35) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNNYIYPFT (SEQ ID NO: 69). In some embodiments according to (or as applied to) any of the embodiments above, the anti-CLDN18.2 antibody or antigen binding fragment comprises a VH domain comprising (a) a CDR-H1 comprising GFTFSDYGMY (SEQ ID NO: 6), (b) a CDR-H2 comprising YISSGSNNIYYADTVKG (SEQ ID NO: 26), and (c) a CDR-H3 comprising IARGNAMDY (SEQ ID NO: 31) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYIYPLT (SEQ ID NO: 67). In some embodiments according to (or as applied to) any of the embodiments above, the anti-CLDN18.2 antibody or antigen binding fragment comprises a VH domain comprising (a) a CDR-H1 comprising GYTFTSWSIS (SEQ ID NO: 9), (b) a CDR-H2 comprising EIYPRSDNIHYNEKFKG (SEQ ID NO: 27), and (c) a CDR-H3 comprising AYYGNSFAY (SEQ ID NO: 34) and/or a VL domain comprising (d) a CDR-L1 comprising KSSQILLNSGNQKNYLT (SEQ ID NO: 51), (e) a CDR-L2 comprising WASTRES (SEQ ID NO: 55), and (f) a CDR-L3 comprising QNDYYYPFT (SEQ ID NO: 70). In some embodiments according to (or as applied to) any of the embodiments above, the anti-CLDN18.2 antibody or antigen binding fragment comprises a VH domain comprising (a) a CDR-H1 comprising GYSFTGYNMN (SEQ ID NO: 10), (b) a CDR-H2 comprising NINPYYSNTNYNQRFKG (SEQ ID NO: 28), and (c) a CDR-H3 comprising CDRGNSFDY (SEQ ID NO: 42) and/or a VL domain comprising (d) a CDR-L1 comprising KSRQSLFNSENQKNYLS (SEQ ID NO: 52), (e) a CDR-L2 comprising WTSTRES (SEQ ID NO: 57), and (f) a CDR-L3 comprising QNNYIYPFT (SEQ ID NO: 69). In some embodiments according to (or as applied to) any of the embodiments above, anti-CLDN18.2 antibody or antigen binding fragment thereof does not specifically bind CLDN18.1.

In some embodiments according to (or as applied to) any of the embodiments above, the anti-CLDN18.2 antibody or antigen binding fragment comprises a VH domain comprising an amino acid sequence set forth in any one of SEQ ID NOs: 72-76, 78-85, and 87-92 and/or a VL domain comprising an amino acid sequence set forth in any one of SEQ ID NOs: 94-98, 100-107, and 109-114. In some embodiments according to (or as applied to) any of the embodiments above, the anti-CLDN18.2 antibody or antigen binding fragment comprises a VH domain comprising SEQ ID NO: 72 and/or a VL domain comprising SEQ ID NO: 94. In some embodiments according to (or as applied to) any of the embodiments above, the anti-CLDN18.2 antibody or antigen binding fragment comprises a VH domain comprising SEQ ID NO: 73 and/or a VL domain comprising SEQ ID NO: 95. In some embodiments according to (or as applied to) any of the embodiments above, the anti-CLDN18.2 antibody or antigen binding fragment comprises a VH domain comprising SEQ ID NO: 74 and/or a VL domain comprising SEQ ID NO: 96. In some embodiments according to (or as applied to) any of the embodiments above, the anti-CLDN18.2 antibody or antigen binding fragment comprises a VH domain comprising SEQ ID NO: 75 and/or a VL domain comprising SEQ ID NO: 97. In some embodiments according to (or as applied to) any of the embodiments above, the anti-CLDN18.2 antibody or antigen binding fragment comprises a VH domain comprising SEQ ID NO: 76 and/or a VL domain comprising SEQ ID NO: 98. In some embodiments according to (or as applied to) any of the embodiments above, the anti-CLDN18.2 antibody or antigen binding fragment comprises a VH domain comprising SEQ ID NO: 78 and/or a VL domain comprising SEQ ID NO: 100. In some embodiments according to (or as applied to) any of the embodiments above, the anti-CLDN18.2 antibody or antigen binding fragment comprises a VH domain comprising SEQ ID NO: 79 and/or a VL domain comprising SEQ ID NO: 101. In some embodiments according to (or as applied to) any of the embodiments above, the anti-CLDN18.2 antibody or antigen binding fragment comprises a VH domain comprising SEQ ID NO: 80 and/or a VL domain comprising SEQ ID NO: 102. In some embodiments according to (or as applied to) any of the embodiments above, the anti-CLDN18.2 antibody or antigen binding fragment comprises a VH domain comprising SEQ ID NO: 81 and/or a VL domain comprising SEQ ID NO: 103. In some embodiments according to (or as applied to) any of the embodiments above, the anti-CLDN18.2 antibody or antigen binding fragment comprises a VH domain comprising SEQ ID NO: 82 and/or a VL domain comprising SEQ ID NO: 104. In some embodiments according to (or as applied to) any of the embodiments above, the anti-CLDN18.2 antibody or antigen binding fragment comprises a VH domain comprising SEQ ID NO: 83 and/or a VL domain comprising SEQ ID NO: 105. In some embodiments according to (or as applied to) any of the embodiments above, the anti-CLDN18.2 antibody or antigen binding fragment comprises a VH domain comprising SEQ ID NO: 84 and/or a VL domain comprising SEQ ID NO: 106. In some embodiments according to (or as applied to) any of the embodiments above, the anti-CLDN18.2 antibody or antigen binding fragment comprises a VH domain comprising SEQ ID NO: 85 and/or a VL domain comprising SEQ ID NO: 107. In some embodiments according to (or as applied to) any of the embodiments above, the anti-CLDN18.2 antibody or antigen binding fragment comprises a VH domain comprising SEQ ID NO: 87 and/or a VL domain comprising SEQ ID NO: 109. In some embodiments according to (or as applied to) any of the embodiments above, the anti-CLDN18.2 antibody or antigen binding fragment comprises a VH domain comprising SEQ ID NO: 88 and/or a VL domain comprising SEQ ID NO: 110. In some embodiments according to (or as applied to) any of the embodiments above, the anti-CLDN18.2 antibody or antigen binding fragment comprises a VH domain comprising SEQ ID NO: 89 and/or a VL domain comprising SEQ ID NO: 111. In some embodiments according to (or as applied to) any of the embodiments above, the anti-CLDN18.2 antibody or antigen binding fragment comprises a VH domain comprising SEQ ID NO: 90 and/or a VL domain comprising SEQ ID NO: 112. In some embodiments according to (or as applied to) any of the embodiments above, the anti-CLDN18.2 antibody or antigen binding fragment comprises a VH domain comprising SEQ ID NO: 91 and/or a VL domain comprising SEQ ID NO: 113. In some embodiments according to (or as applied to) any of the embodiments above, the anti-CLDN18.2 antibody or antigen binding fragment comprises a VH domain comprising SEQ ID NO: 92 and/or a VL domain comprising SEQ ID NO: 114. In some embodiments according to (or as applied to) any of the embodiments above, anti-CLDN18.2 antibody or antigen binding fragment thereof does not specifically bind CLDN18.1.

Provided is an anti-CLDN18.2 antibody or antigen binding fragment thereof comprising: (a) a CDR-H1 comprising GFX$_1$FSDYGMX$_2$(SEQ ID NO: 121), wherein X$_1$ is T or S; and X$_2$ is H or Y; (b) a CDR-H2 comprising X$_1$ISSGSSX$_2$YX$_3$ADTX$_4$KG (SEQ ID NO: 122), wherein X$_1$ is Y, H, or F; X$_2$ is S or T; X$_3$ is Y or C; and X$_4$ is V or M; (c) a CDR-H3 comprising X$_1$ARGNX$_4$MDY (SEQ ID NO: 123), wherein X$_1$ is I or F; and X$_4$ is T or A; (d) a CDR-L1 comprising KSSQSLLNSGNX$_1$X$_2$NYLX$_3$ (SEQ ID NO: 124), wherein X$_1$ is Q or L; X$_2$ is R or K; and X$_3$ is T or A; (e) a CDR-L2 comprising WASTRES (SEQ ID NO: 55); and (f) a CDR-L3 comprising QNX$_1$YX$_2$YPLT (SEQ ID NO: 125), wherein $X_1$ is G or D; and $X_2$ is S or F. In some embodiments according to (or as applied to) any of the embodiments above, the anti-CLDN18.2 antibody or antigen binding fragment thereof binds claudin 18.1 (CLDN18.1).

In some embodiments according to (or as applied to) any of the embodiments above, the anti-CLDN18.2 antibody or antigen binding fragment thereof comprises a VH domain comprising (a) a CDR-H1 comprising an amino acid sequence set forth in any one of SEQ ID NOs: 2, 6, and 7, (b) a CDR-H2 comprising an amino acid sequence forth in any one of SEQ ID NOs: 17, 22, and 29, and (c) a CDR-H3 comprising an amino acid sequence forth in SEQ ID NO: 31 or SEQ ID NO: 37 and/or a VL domain comprising (d) a CDR-L1 comprising an amino acid sequence set forth in any one of SEQ ID NOs: 44, 48, and 53, (e) a CDR-L2 comprising an amino acid sequence set forth in SEQ ID NO: 55, and (f) a CDR-L3 comprising an amino acid sequence set forth in any one of SEQ ID NOs: 59, 60, and 64. In some embodiments according to (or as applied to) any of the embodiments above, the anti-CLDN18.2 antibody or antigen binding fragment thereof binds claudin 18.1 (CLDN18.1).

In some embodiments according to (or as applied to) any of the embodiments above, the anti-CLDN18.2 antibody or antigen binding fragment thereof comprises a VH domain comprising (a) a CDR-H1 comprising GFTFSDYGMH (SEQ ID NO: 2), (b) a CDR-H2 comprising YISSGSSSIYY-ADTVKG (SEQ ID NO: 17), and (c) a CDR-H3 comprising IARGNAMDY (SEQ ID NO: 31) and/or a VL domain comprising (d) a CDR-L1 comprising KSSQSLLNSGNQR-NYLA (SEQ ID NO: 48), (e) a CDR-L2 comprising WAST-RES (SEQ ID NO: 55), and (f) a CDR-L3 comprising QNDYSYPLT (SEQ ID NO: 64). In some embodiments according to (or as applied to) any of the embodiments above, the anti-CLDN18.2 antibody or antigen binding fragment thereof comprises a VH domain comprising (a) a CDR-H1 comprising GFSFSDYGMH (SEQ ID NO: 7), (b) a CDR-H2 comprising HISSGSSTIYYADTMKG (SEQ ID NO: 22), and (c) a CDR-H3 comprising FARGNTMDY (SEQ ID NO: 37) and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNGYSYPLT (SEQ ID NO: 60). In some embodiments according to (or as applied to) any of the embodiments above, the anti-CLDN18.2 antibody or antigen binding fragment thereof comprises a VH domain comprising (a) a CDR-H1 comprising GFTFSDYGMY (SEQ ID NO: 6), (b) a CDR-H2 comprising FISSGSSTIYCADTVKG (SEQ ID NO: 29), and (c) a CDR-H3 comprising IARGNAMDY (SEQ ID NO: 31) and/or a VL domain comprising (d) a CDR-L1 comprising KSSQSLLNSGNLKNYLT (SEQ ID NO: 53), (e) a CDR-L2 comprising WASTRES (SEQ ID NO: 55), and (f) a CDR-L3 comprising QNDYFYPLT (SEQ ID NO: 59). In some embodiments according to (or as applied to) any of the embodiments above, the anti-CLDN18.2 antibody or antigen binding fragment thereof binds claudin 18.1 (CLDN18.1).

In some embodiments according to (or as applied to) any of the embodiments above, the anti-CLDN18.2 antibody or antigen binding fragment thereof comprises a VH domain comprising an amino acid sequence set forth in any one of SEQ ID NOs: 77, 86, and 93 and/or a VL domain comprising an amino acid sequence set forth in any one of SEQ ID NOs: 99, 108, and 115. In some embodiments according to (or as applied to) any of the embodiments above, the anti-CLDN18.2 antibody or antigen binding fragment thereof comprises a VH domain comprising SEQ ID NO: 77 and/or a VL domain comprising SEQ ID NO: 99. In some embodiments according to (or as applied to) any of the embodiments above, the anti-CLDN18.2 antibody or antigen binding fragment thereof comprises a VH domain comprising SEQ ID NO: 86 and/or a VL domain comprising SEQ ID NO: 108. In some embodiments according to (or as applied to) any of the embodiments above, the anti-CLDN18.2 antibody or antigen binding fragment thereof comprises a VH domain comprising SEQ ID NO: 93 and/or a VL domain comprising SEQ ID NO: 115. In some embodiments according to (or as applied to) any of the embodiments above, the anti-CLDN18.2 antibody or antigen binding fragment thereof binds claudin 18.1 (CLDN18.1).

Provided is an anti-CLDN18.2 antibody or antigen binding fragment thereof comprising a CDR-H3 that consists of 4 amino acids, less than 4 amino acids, or three amino acids. Also provided is an anti-CLDN18.2 antibody or antigen binding fragment thereof comprising: (a) a CDR-H1 comprising CDR-H1 comprising GYTFX$_1$X$_2$YX$_3$X$_4$H (SEQ ID NO: 139), wherein: $X_1$ is T or I; $X_2$ is S or N; $X_3$ is L or V; and $X_4$ is I or M; (b) a CDR-H2 comprising a CDR-H2 comprising YINPX$_1$X$_2$DGTKYNEKFKG (SEQ ID NO: 140), wherein: $X_1$ is Y or F; and $X_2$ is N or D; (c) a CDR-H3 comprises GDX$_1$, wherein X is F or Y; (d) a CDR-L1 comprising KSSQSLLNSGNQKNYLT (SEQ ID NO: 44); (e) a CDR-L2 comprising WASX$_1$RX$_2$S (SEQ ID NO: 141), wherein $X_1$ is T or I; and $X_2$ is A or D; and (f) a CDR-L3 comprising LNDYSFPLT (SEQ ID NO: 131). In some embodiments according to (or as applied to) any of the embodiments above, the anti-CLDN18.2 antibody or antigen binding fragment thereof specifically binds claudin 18.1 (CLDN18.1).

In some embodiments according to (or as applied to) any of the embodiments above, the anti-CLDN18.2 antibody or antigen binding fragment thereof comprises (a) a CDR-H1 comprising an amino acid sequence set forth in SEQ ID NO: 128 or 132; (b) a CDR-H2 comprising an amino acid sequence set forth in SEQ ID NO: 129 or 133; (c) a CDR-H3 comprising GDF or GDY; (d) a CDR-L1 comprising an amino acid sequence set forth in SEQ ID NO: 44; (e) a CDR-L2 comprising an amino acid sequence set forth in SEQ ID NO: 130 or 134; and (f) a CDR-L3 comprising an amino acid sequence set forth in SEQ ID NO: 131. In some embodiments according to (or as applied to) any of the embodiments above, the anti-CLDN18.2 antibody or antigen binding fragment thereof comprises (i) a VH domain comprising (a) a CDR-H1 comprising GYTFISYLIH (SEQ ID NO: 128), (b) a CDR-H2 comprising YINPYNDGT-KYNEKFKG (SEQ ID NO: 129), (c) a CDR-H3 comprising GDF and/or a VL domain comprising (d) a CDR-L1 comprising KSSQSLLNSGNQKNYLT (SEQ ID NO: 44), (e) a CDR-L2 comprising WASIRAS (SEQ ID NO: 130), and (f) a CDR-L3 comprising LNDYSFPLT (SEQ ID NO: 131). In some embodiments according to (or as applied to) any of the embodiments above, the anti-CLDN18.2 antibody or antigen binding fragment thereof comprises a VH domain comprising (a) a CDR-H1 comprising GYTFTNYVMH (SEQ ID NO: 132), (b) a CDR-H2 comprising YINPFDDGTKYNEKFKG (SEQ ID NO: 133), (c) a CDR-H3 comprising GDY and/or a VL domain comprising (d) a CDR-L1 comprising KSSQSLLNSGNQKNYLT (SEQ ID NO: 44), (e) a CDR-L2 comprising WASTRDS (SEQ ID NO: 134), and (f) a CDR-L3 comprising LNDYSFPLT (SEQ ID NO: 131). In some embodiments according to (or as applied to) any of the embodiments above, the anti- CLDN18.2 antibody or antigen binding fragment thereof specifically binds claudin 18.1 (CLDN18.1).

In some embodiments according to (or as applied to) any of the embodiments above, the anti-CLDN18.2 antibody or antigen binding fragment thereof comprises a VH domain comprising an amino acid sequence set forth in any one of SEQ ID NOs: 135 and 136; and/or a VL domain comprising an amino acid sequence set forth in any one of SEQ ID NOs: 137 and 138. In some embodiments according to (or as applied to) any of the embodiments above, the anti-CLDN18.2 antibody or antigen binding fragment thereof comprises a VH domain comprising SEQ ID NO: 135; and/or a VL domain comprising SEQ ID NO: 137. In some embodiments according to (or as applied to) any of the embodiments above, the anti-CLDN18.2 antibody or antigen binding fragment thereof comprises a VH domain comprising SEQ ID NO: 136; and/or a VL domain comprising SEQ ID NO: 138. In some embodiments according to (or as applied to) any of the embodiments above, the anti-CLDN18.2 antibody or antigen binding fragment thereof specifically binds claudin 18.1 (CLDN18.1).

In some embodiments according to (or as applied to) any of the embodiments above, the anti-CLDN18.2 antibody or antigen binding fragment thereof comprises an Fc sequence of a human IgG. In some embodiments according to (or as applied to) any of the embodiments above, the human IgG is IgG1, IgG2, IgG3 or IgG4. In some embodiments according to (or as applied to) any of the embodiments above, the anti-CLDN18.2 antibody or antigen binding fragment thereof is a chimeric, humanized, or human antibody. In some embodiments according to (or as applied to) any of the embodiments above, the antigen binding fragment is selected from the group consisting of: a Fab, a Fab', a F(ab)'2, a single-chain Fv (scFv), an Fv fragment, a diabody, and a linear antibody. In some embodiments according to (or as applied to) any of the embodiments above, the antibody is a multispecific antibody. In some embodiments according to (or as applied to) any of the embodiments above, the CLDN18.2 is human CLDN18.2. In some embodiments according to (or as applied to) any of the embodiments above, the CLDN18.1 is human CLDN18.1.

In some embodiments according to (or as applied to) any of the embodiments above, the anti-CLDN18.2 antibody or antigen binding fragment thereof is conjugated to a therapeutic agent. In some embodiments according to (or as applied to) any of the embodiments above, the anti-CLDN18.2 antibody or antigen binding fragment thereof is conjugated to a label. In some embodiments according to (or as applied to) any of the embodiments above, the label is selected from the group consisting of a radioisotope, a fluorescent dye, and an enzyme. In some embodiments according to (or as applied to) any of the embodiments above, the anti-CLDN18.2 antibody or antigen binding fragment thereof is part of an anti-CLDN18.2 construct, such as a chimeric antigen receptor (anti-CLDN18.2 CAR). In some embodiments, the anti-CLDN18.2 CAR comprises an extracellular domain comprising the anti-CLDN18.2 antibody or antigen binding fragment thereof, a transmembrane domain, and an intracellular signaling domain. In some embodiments, the intracellular signaling domain comprises a CD3ζ intracellular signaling sequence and a co-stimulatory signaling sequence or a combination of co-stimulatory signaling sequences. In some embodiments, the co-stimulatory signaling sequence is a CD28 intracellular signaling sequence. In some embodiments, the co-stimulatory signaling sequence is a 4-1-BB intracellular signaling sequence. In some embodiments, the co-stimulatory signaling sequence is a combination of CD28 and 4-1-BB or other co-stimulatory signaling sequences. In some embodiments, the intracellular signaling domain comprises a CD3ζ intracellular signaling sequence and a co-stimulatory signaling sequence or a combination of co-stimulatory signaling sequences are transfected along with a cytokine transgene, e.g., a CAR-inducible interleukin-12 (iIL-12) cassette.

Provided are isolated nucleic acid molecule(s) that encode the anti-CLDN18.2 antibody or antigen binding fragment thereof (or anti-CLDN18.2 constructs) according to (or as applied to) any of the embodiments above. Also provided are expression vectors encoding the nucleic acid molecule(s) according to (or as applied to) any of the embodiments above. Provided are host cells comprising the nucleic acid molecule(s) or the expression vectors according to (or as applied to) any of the embodiments above. Also provided are immune cells (such as T cells, NK Cells or macrophages) comprising any of the anti-CLDN18.2 CAR described above (such as anti-CLDN18.2 CART) and methods of making such immune cells.

Also provided is a method of producing an anti-CLDN18.2 antibody, comprising culturing the host cell according to (or as applied to) any of the embodiments above. In some embodiments according to (or as applied to) any of the embodiments above, the method further comprises recovering the antibody from the cell culture.

Provided is a method of detecting a CLDN18.2 protein in sample from a patient by contacting the anti-CLDN18.2 antibody or antigen binding fragment thereof according to (or as applied to) any of the embodiments above to the sample and detecting the anti-CLDN18.2 antibody bound to the CLDN18.2 protein. In some embodiments according to (or as applied to) any of the embodiments above, the anti-CLDN18.2 antibody or antigen binding fragment thereof is used an immunohistochemistry assay (IHC) or in an ELISA assay.

Also provided composition comprising the anti-CLDN18.2 antibody or antigen binding fragment thereof according to (or as applied to) any of the embodiments above and a pharmaceutically acceptable carrier. Provided is a method of treating cancer in a subject, comprising administering an effective amount of a pharmaceutical composition according to (or as applied to) any of the embodiments above to the subject. In some embodiments according to (or as applied to) any of the embodiments above, the cancer is selected from solid tumor, gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer. In some embodiments according to (or as applied to) any of the embodiments above, the subject is further administered a therapeutic agent selected from the group consisting of an anti-neoplastic agent, a chemotherapeutic agent, a growth inhibitory agent and a cytotoxic agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3C. provides the results of experiments that were performed to assess the binding of anti-CLDN18.2 antibodies 10-K12-A, 1-B13-A, 9-M7-A, and 10-P12-A as compared to reference anti-CLDN18.2 antibody IMAB362 to CLDN18.2 expressed on the surface of NUGC-4 human gastric adenocarcinoma cells.

FIG. 4A provides the results of ELISA experiments that were performed to determine whether anti-CLDN18.2 antibodies 10-K12-A, 1-B13-A, 6-C5-A, 7-A21-A, 7-G17-A, 9-B11-A, 9-M7-A, 9-N14-A, and 10-J10-B can bind to peptide 2C, a cyclized peptide that has previously been shown to bind anti-CLDN18.2 antibody IMAB362 with sub-nanomolar affinity.

FIG. 4B provides the results of ELISA experiments that were performed to determine whether anti-CLDN18.2 antibodies 10-K12-A, 1-B13-A, 6-C5-A, 7-A21-A, 7-G17-A, 9-B11-A, 9-M7-A, 9-N14-A, and 10-J10-B can bind to peptide 3C, a cyclized peptide that has previously been shown to bind anti-CLDN18.2 antibody IMAB362 with sub-nanomolar affinity.

FIG. 5 provides the results of a competition assay that was performed to determine whether peptide 2C or 3C inhibited the binding of anti-CLDN18.2 antibodies 10-K12-A, 1-B13-A, 1-M5-A, 2-D22-A, 4-N1-A, 5-22-A, 6-C5-A, 6-M11-A, 7-A21-A, 7-B15-A, 7-E20A, 7-G17-A, 9-B11-A, 9-C6-A, 9-M7-A, 9-N14-A, 10-J10-B, 10-P12-A, or reference antibody IMAB362 to HEK293-CLDN18.2 cells.

FIG. 6A shows the mean tumor volume as a function of time during treatment with each antibody (or vehicle control). FIG. 6B shows the % inhibition of tumor growth as a function of time during treatment with each antibody (or vehicle control).

DETAILED DESCRIPTION OF THE INVENTION

Definitions

Figure 1:
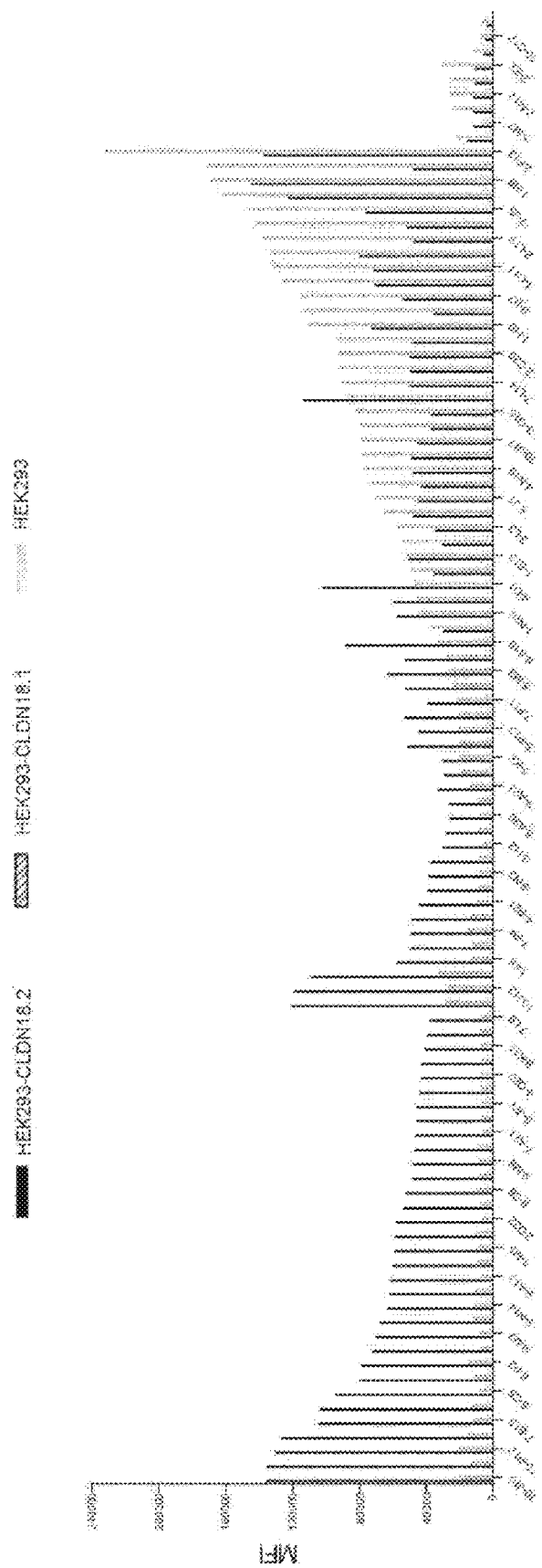
FIG. 1 shows the results of FACS analyses performed using supernatants from hybridomas in order assess antibody binding to HEK293-CLDN18.2 (red), HEK293-CLDN18.1 (blue) and parental HEK293 cells (gray).

Before describing the disclosed embodiments in detail, it is to be understood that the present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising," "consisting," and "consisting essentially of" aspects and embodiments.

The term "claudin 18" or "CLDN18" preferably refers to human CLDN18 and includes any splice variants such as CLDN18.1 and CLDN18.2 of CLDN 18. CLDN18.1 and CLDN18.2 differ in the N-terminal portion which comprises the first transmembrane (TM) region and loop 1, whereas the primary protein sequence of the C-terminus is identical.

The term "CLDN18.1" preferably relates to human CLDN18.1, and, in particular, to a protein comprising the amino acid sequence

```
                                      (SEQ ID NO: 126)
MSTTTCQVVA FLLSILGLAG CIAATGMDMW STQDLYDNPV

TSVFQYEGLW RSCVRQSSGF TECRPYFTIL GLPAMLQAVR

ALMIVGIVLG AIGLLVSIFA LKCIRIGSME DSAKANMTLT

SGIMFIVSGL CAIAGVSVFA NMLVTNFWMS TANMYTGMGG

MVQTVQTRYT FGAALFVGWV AGGLTLIGGV MMCIACRGLA

PEETNYKAVS YHASGHSVAY KPGGFKASTG FGSNTKNKKI

YDGGARTEDE VQSYPSKHDY V
``` or a variant of said amino acid sequence.

The term "CLDN18.2" preferably relates to human CLDN18.2, and, in particular, to a protein comprising the amino acid sequence

```
                                      (SEQ ID NO: 127)
MAVTACQGLG FVVSLIGIAG IIAATCMDQW STQDLYNNPV

TAVFNYQGLW RSCVRESSGF TECRGYFTLL GLPAMLQAVR

ALMIVGIVLG AIGLLVSIFA LKCIRIGSME DSAKANMTLT

SGIMFIVSGL CAIAGVSVFA NMLVTNFWMS TANMYTGMGG

MVQTVQTRYT FGAALFVGWV AGGLTLIGGV MMCIACRGLA

PEETNYKAVS YHASGHSVAY KPGGFKASTG FGSNTKNKKI

YDGGARTEDE VQSYPSKHDY V
``` of the or a variant of said amino acid sequence.

The terms "CLDN," "CLDN18," "CLDN18.1" and "CLDN18.2" refer to any posttranslationally modified variants and conformation variants.

As used herein, the term "antibody" may refer to intact (full length) antibodies; antibody fragments (including without limitation Fab, F(ab')2, Fab'-SH, Fv, diabodies, scFv, scFv-Fc, single domain antibodies, single heavy chain antibodies, and single light chain antibodies), provided that they exhibit the desired biological activity (e.g. epitope binding); monoclonal antibodies; polyclonal antibodies; monospecific antibodies; multi-specific antibodies (e.g., bispecific antibodies); and antibody-like proteins, including, but not limited to, e.g., fusion proteins, cysteine engineered antibodies, covalently modified antibodies, and antibody conjugates (such as antibody-drug conjugates or antibodies conjugated to detectable labels).

An "isolated" antibody may refer to an antibody that has been separated and/or recovered from a component of its natural environment, e.g., a host cell or organism. In some embodiments, an antibody is purified to a desired purity by weight (e.g., at least 95%); and/or homogeneity by SDS-PAGE using, for example, staining by silver, Coomassie, etc. In some embodiments, an isolated antibody is obtained following one or more purification steps.

As is known in the art, "native" antibodies refer to typically heterotetrameric complexes including two identical light (L) chains and two identical heavy (H) chains. Variable numbers of disulfide bonds connect the two heavy chains, and one connects each light chain to a heavy chain, in addition to intrachain disulfide bridges. The heavy chains include a variable domain (VH) followed (N-terminus to C-terminus) by three or four constant domains. The light chains include a variable domain (VL) followed by a constant domain (CL). Typically, mammalian light chains fall into one of two categories based on amino acid sequence: kappa and lambda.

A "constant domain" may refer to the more conserved portion of the antibody or fragment, e.g., outside the variable domains. The term may include the CL domain as well as heavy chain constant domains CH1, CH2, CH3 and optionally CH4.

Constant domains of the heavy chain can be assigned to one of 5 major types: IgA, IgD, IgE, IgG, and IgM. Several subtypes exist for many of these major types. The subunit structures and three-dimensional configurations of different classes of immunoglobulins are well known and described generally in, for example, Abbas et al. Cellular and Mol. Immunology, 4th ed. (W.B. Saunders, Co., 2000).

As used herein, the term "antibody variable domain" refers to the portions of the light and heavy chains of an antibody that include the complementary determining regions (CDRs, e.g., CDR L1, CDR L2, CDR L3, CDR H1, CDR H2, and CDR H3) and framework regions (FRs).

The term "variable" refers to the fact that subsequences of the variable domains differ substantially in sequence between antibodies and are critical to the binding specificity of a particular antibody for its antigen. Variability is concentrated in three "hypervariable regions" (HVRs) or "complementarity determining regions" (CDRs) in both VH and VL domains. (The terms "HVR" and "CDR" are used interchangeably herein.) The more conserved portions of variable domains are called the framework regions (FR) in which the CDRs are interspersed. The variable domains of native heavy and light chains each comprise four FR regions connected by three CDRs that form loops (see Kabat et al., Sequences of Proteins of Immunological Interest, Fifth Edition, National Institute of Health, Bethesda, Md. (1991)).

The term "hypervariable region (HVR)" or "complementarity determining region (CDR)" may refer to the subregions of the VH and VL domains characterized by enhanced sequence variability and/or formation of defined loops. These include three CDRs in the VH domain (H1, H2, and H3) and three CDRs in the VL domain (L1, L2, and L3). H3 is believed to be critical in imparting fine binding specificity, with L3 and H3 showing the highest level of diversity. See Johnson and Wu, in Methods in Molecular Biology 248:1-25 (Lo, ed., Human Press, Totowa, N.J., 2003).

A number of CDR/HVR delineations are known. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs/CDRs are noted below. "Framework" or "FR" residues are those variable domain residues other than the HVR/CDR residues.

| Loop | Kabat    | AbM      | Chothia  | Contact                  |
|------|----------|----------|----------|--------------------------|
| L1   | L24-L34  | L24-L34  | L26-L32  | L30-L36                  |
| L2   | L50-L56  | L50-L56  | L50-L52  | L46-L55                  |
| L3   | L89-L97  | L89-L97  | L91-L96  | L89-L96                  |
| H1   | H31-H35B | H26-H35B | H26-H32  | H30-H35B(Kabat Numbering) |
| H1   | H31-H35  | H26-H35  | H26-H32  | H30-H35 (Chothia Numbering) |
| H2   | H50-H65  | H50-H58  | H53-H55  | H47-H58                  |
| H3   | H95-H102 | H95-H102 | H96-H101 | H93-H101                 |

"Extended" HVRs are also known: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH (Kabat numbering).

"Numbering according to Kabat" may refer to the numbering system used for heavy chain variable domains or light chain variable domains of the compilation of antibodies in Kabat et al., supra. The actual linear amino acid sequence may contain fewer or additional amino acids corresponding to a shortening of, or insertion into, a FR or HVR of the variable domain. The Kabat numbering of residues may be determined for a given antibody by alignment at regions of homology of the sequence of the antibody with a "standard" Kabat numbered sequence. Typically, the Kabat numbering is used when referring to a residue in the variable domains (approximately residues 1-107 of the light chain and residues 1-113 of the heavy chain), whereas the EU numbering system or index (e.g., the EU index as in Kabat, numbering according to EU IgG1) is generally used when referring to a residue in the heavy chain constant region.

"Full length" or "intact" antibodies typically include heavy chains with an Fc region, e.g., as opposed to an antibody fragment. Antigen-binding "Fab" fragments with a single antigen binding site may be released from the residual Fc fragment by papain digestion. F(ab')2 fragments include two antigen-binding sites produced by pepsin treatment of an antibody. Antibody fragments will, however, include one or more antibody variable regions.

An "Fv" fragment contains a complete antigen-binding site. A single chain Fv (scFv) can include a VH and a VL domain linked by a peptide linker such that the VH and VL domains associate, e.g., as in an antibody or Fab fragment, such that the HVRs form an antigen binding site. See Pluckthün, in The Pharmacology of Monoclonal Antibodies, vol. 113, Rosenburg and Moore eds., (Springer-Verlag, New York, 1994), pp. 269-315. In some embodiments, the scFv is fused to an antibody Fc domain (e.g., scFv-Fc). While six HVRs typically comprise an antigen binding site, a single variable domain with three HVRs is still capable of binding an antigen, albeit at a lower affinity. See Hamers-Casterman et al., Nature 363:446-448 (1993); Sheriff et al., Nature Struct. Biol. 3:733-736 (1996). Single domain antibodies (e.g., camelid antibodies) typically include a single, monomeric variable domain for antigen binding. Single heavy chain (VHH) and single light chain antibodies are also known. A Fab' fragment typically includes a few more residues at the C-terminal end than a Fab fragment. A Fab'-SH includes cysteine residues with a free thiol. Various chemical couplings of antibody fragments are known in the art.

A "diabody" includes antibody fragments with two antigen-binding sites. These include a VH and VL domain connected by a linker, which is typically too short to facilitate pairing of domains in the same chain. Diabodies may be bivalent or bispecific. Tribodies and tetrabodies, or other numbers of VH/VL domains are known. See Hudson et al., Nat. Med. 9:129-134 (2003).

As used herein, a "monoclonal" antibody refers to an antibody obtained from a population of substantially homogeneous antibodies, e.g., substantially identical but allowing for minor levels of background mutations and/or modifications. "Monoclonal" denotes the substantially homogeneous character of antibodies, and does not require production of the antibody by any particular method. In some embodiments, a monoclonal antibody is selected by its HVR, VH, and/or VL sequences and/or binding properties, e.g., selected from a pool of clones (e.g., recombinant, hybridoma, or phage-derived). A monoclonal antibody may be engineered to include one or more mutations, e.g., to affect binding affinity or other properties of the antibody, create a humanized or chimeric antibody, improve antibody production and/or homogeneity, engineer a multispecific antibody, resultant antibodies of which are still considered to be monoclonal in nature. A population of monoclonal antibodies may be distinguished from polyclonal antibodies as the individual monoclonal antibodies of the population recognize the same antigenic site. A variety of techniques for production of monoclonal antibodies are known; see, e.g., the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

"Chimeric" antibodies may refer to an antibody with one portion of the heavy and/or light chain from a particular isotype, class, or organism and another portion from another isotype, class, or organism. In some embodiments, the variable region will be from one source or organism, and the constant region will be from another.

"Humanized antibodies" may refer to antibodies with predominantly human sequence and a minimal amount of non-human (e.g., mouse or chicken) sequence. In some embodiments, a humanized antibody has one or more HVR sequences (bearing a binding specificity of interest) from an antibody derived from a non-human (e.g., mouse or chicken) organism grafted onto a human recipient antibody framework (FR). In some embodiments, non-human residues are further grafted onto the human framework (not present in either source or recipient antibodies), e.g., to improve antibody properties. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See Jones et al., Nature 321:522-525 (1986); Riechmann et al., Nature 332:323-329 (1988); and Presta, Curr. Op. Struct. Biol. 2:593-596 (1992).

A "human" antibody may refer to an antibody having an amino acid sequence which corresponds to that of an antibody produced by a human and/or has been made using any of the techniques for making human antibodies as disclosed herein. Human antibodies can be produced using various techniques known in the art, including phage-display libraries. Hoogenboom and Winter, J. Mol. Biol., 227:381 (1991); Marks et al., J. Mol. Biol., 222:581 (1991); preparation of human monoclonal antibodies as described in Cole et al., Monoclonal Antibodies and Cancer Therapy, Alan R. Liss, p. 77 (1985); Boerner et al., J. Immunol., 147(1):86-95 (1991); and by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENO-MOUSE™ technology) or chickens with human immunoglobulin sequence(s) (see, e.g., WO2012162422, WO2011019844, and WO2013059159).

The term "cytotoxic agent" as used herein may refer to any agent that inhibits cellular proliferation or induces cell death. Cytotoxic agents include, but are not limited to, chemotherapeutic agents; radioactive isotopes; growth inhibitory agents; and toxins such as small molecule toxins or enzymatically active toxins, including fragments and/or variants thereof. Exemplary cytotoxic agents include without limitation metabolic inhibitors, anti-microtubule agents, platinum containing compounds, alkylating agents, proteasome inhibitors, topoisomerase II inhibitors, antimetabolites, topoisomerase I inhibitors, signal transduction pathway inhibitors, non-receptor tyrosine kinase angiogenesis inhibitors, hormones and hormonal analogues, proapoptotic agents, inhibitors of LDH-A, cell cycle inhibitors, HDAC inhibitors, and antibiotic agents.

As used herein, a "label" may include any moiety that serves as a detection agent, e.g., of binding between a labeled antibody of the present disclosure and a macromolecule or cell. Exemplary labels include without limitation fluorescent (e.g., compounds or proteins), radioactive, or enzymatic moieties, as well as affinity purification tags.

The term "detecting" is intended to include determining the presence or absence of a substance or quantifying the amount of a substance (such as CLDN18.2). The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of a CLDN18.2 gene product of a CLDN18.2 polypeptide; a change in the levels of a CLDN18.2 polypeptide or amount bound to a target; a change in biological function/activity of a CLDN18.2 polypeptide. In some embodiments, "detecting" may include detecting wild type CLDN18.2 levels (e.g., polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

As used herein, an antibody may be said to "bind" an antigen with an affinity sufficient to render the antibody useful for in vitro and/or in vivo manipulation of the antigen.

As used herein, the term "affinity" or "binding affinity" refers to the strength of the binding interaction between two molecules. Generally, binding affinity refers to the strength of the sum total of non-covalent interactions between a molecule and its binding partner, such as a high affinity SIRP-α D1 variant and CD47. Unless indicated otherwise, binding affinity refers to intrinsic binding affinity, which reflects a 1:1 interaction between members of a binding pair. The binding affinity between two molecules is commonly described by the dissociation constant ($K_d$) or the association constant (Ka). Two molecules that have low binding affinity for each other generally bind slowly, tend to dissociate easily, and exhibit a large $K_d$. Two molecules that have high affinity for each other generally bind readily, tend to remain bound longer, and exhibit a small $K_d$. In some embodiments, the $K_d$ of two interacting molecules is determined using known methods and techniques, e.g., surface plasmon resonance (SPR). $K_d$ can be calculated as the ratio of koff/kon.

As used herein, the term "$K_d$ less than" refers to a numerically smaller $K_d$ value and an increasing binding affinity relative to the recited $K_d$ value. As used herein, the term "$K_d$ greater than" refers to a numerically larger $K_d$ value and a decreasing binding affinity relative to the recited $K_d$ value.

As used herein, "treatment" may refer to therapeutic administration of a molecule, compound, formulation, composition, etc. to obtain beneficial or desired therapeutic results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, palliating a pathological symptom or disease state, increasing or improving the quality of life, preventing excessive weight loss, improving prognosis, achieving disease remission and/or prolonging survival. Also encompassed by "treatment" is a reduction of pathological consequence of cancer (such as, for example, tumor volume). The methods provided herein contemplate any one or more of these aspects of treatment.

As used herein, "delaying progression" of a disease may refer to slowing, retarding, deferring, postponing development of, stabilizing, or otherwise hindering the pathological course of the disease. In some embodiments, the term may refer to a delay sufficient to effectively encompass prevention, e.g., in preventing the individual from developing the disease. In some embodiments, e.g., an advanced cancer, delaying progression may include delaying metastasis. One of skill in the art will appreciate that the precise length of delay may depend, e.g., upon the specific disease, condition of the individual, and the like.

The terms "recurrence," "relapse" or "relapsed" refers to the return of a disease or disorder characterized by abnormal CLDN18.2 expression or abnormal CLDN18.2 activity, (e.g., a tumor or cancer, such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) resulting from after clinical assessment of the disappearance of disease.

The term "refractory" or "resistant" refers to a disease or disorder characterized by abnormal CLDN18.2 expression or abnormal CLDN18.2 activity, (e.g., cancer, such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) that has not responded to treatment with a particular agent or combination of agents.

As used herein, the term "effective amount" may refer to an amount of an antibody of the present disclosure or a pharmaceutical composition containing an antibody of the present disclosure that is sufficient and effective in achieving a desired therapeutic effect in treating or delaying progression of a patient having a disease, such as CLDN18.2-expressing tumor or a cancer characterized by abnormal CLDN18.2 expression or activity, e.g., gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc. In some embodiments, a therapeutically effective amount will avoid adverse side effects, and/or such side effects will be outweighed by beneficial effects. An effective amount may depend upon the individual being treated, e.g., age, weight, sex, disease state, as well as the ability of the agent to produce a desired response. An effective amount can be administered in one or more administrations. As in the clinical context, an effective amount of a drug, compound, or pharmaceutical composition may or may not be achieved in conjunction with another drug, compound, or pharmaceutical composition, such as another therapeutic agent. Thus, an "effective amount" may also be considered in the context of administering one or more additional therapeutic agents, and a single agent may be considered to be given in an effective amount if, in conjunction with one or more other agents, a desirable result may be or is achieved.

The term "therapeutically effective amount" refers to an amount of an anti-CLDN18.2 antibody (or fragment thereof) or composition as disclosed herein, effective to "treat" a disease or disorder in a mammal (aka patient or subject). In the case of cancer, the therapeutically effective amount of the anti-CLDN18.2 antibody (or fragment thereof) or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the CLDN18.2 antibody (or fragment thereof) or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

As used herein, the term "pharmaceutical composition" may refer to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with one or more antibodies of the present disclosure. In some embodiments, the pharmaceutical composition is in tablet or capsule form for oral administration or in aqueous form for intravenous or subcutaneous administration, for example by injection.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, the terms "subject," "individual," and "patient" are used interchangeably to refer to a vertebrate, for example, a mammal. Mammals include, but are not limited to, murines, simians, humans, farm animals, sport animals, and pets.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

All references cited herein, including patent applications and publications, are hereby incorporated by reference in their entirety.

Anti-Claudin 18.2 (CLDN18.2) Antibodies

The present disclosure is based on the identification of antibodies that bind claudin 18.2 (CLDN18.2). The anti-CLDN18.2 antibodies provided herein may be used in a variety of therapeutic and diagnostic methods. For example, the anti-CLDN18.2 antibodies may be used alone or in combination with other agents in treating a disease or disorder characterized by abnormal CLDN18.2 expression or abnormal CLDN18.2 activity, including, but not limited to solid tumor or cancer, e.g., gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc. The antibodies provided herein can also be used for detecting CLDN18.2 in patients or patient samples by, e.g., administering an anti-CLDN18.2 antibody to a patient and detecting the anti-CLDN18.2 antibody bound to CLDN18.2 (e.g., in vivo or ex vivo), or, e.g., by contacting a sample from a patient with an anti-CLDN18.2 antibody and qualitatively or quantitatively detecting the anti-CLDN18.2 antibody bound to the CLDN18.2 protein.

An anti-CLDN18.2 antibody is an antibody that binds to CLDN18.2 with sufficient affinity and specificity. For example, an anti-CLDN18.2 antibody provided herein (or a biologically active fragment thereof) may be used as a therapeutic agent in targeting and interfering with diseases or conditions associated with aberrant/abnormal CLDN18.2 expression and/or activity. In some, the anti-CLDN18.2 antibody is a chimeric monoclonal antibody. In some embodiments, the anti-CLDN18.2 antibody comprises at least one CDR, a heavy chain variable domain (VH), and/or a light chain variable domain (VL) of an antibody disclosed herein.

In certain embodiments, an anti-CLDN18.2 antibody provided herein (or antigen binding fragment thereof) comprises one, two, three, four, five, or six complementarity determining region (CDR) sequences selected from the group consisting of: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9X_{10}X_{11}X_{12}X_{13}X_{14}KG$ (SEQ ID NO: 30), wherein $X_1$ is Y, E, T, H, or N; $X_2$ is S, N, D, Y, or I; $X_3$ is S, P, or I; $X_4$ is G, N, K, R, or Y; $X_5$ is S, N, G, or Y; $X_6$ is S, G, T, N, or D; $X_7$ is N, T, V, Y, I, or P; $X_8$ is I, T, or F; $X_9$ is Y, H, or N; $X_{10}$ is Y, or S; $X_{11}$ is A, N, P, T, or V; $X_{12}$ is D, Q, or E; $X_{13}$ is T, K, S, or R; and $X_{14}$ is V, F, M, or L; (c) a CDR-H3 comprising $X_1X_2X_3GNX_4X_5X_6Y$ (SEQ ID NO: 43), wherein: $X_1$ is I, F, P, A, Q, or H; $X_2$ is A, Y, V, T; $X_3$ is R or Y; $X_4$ is A, V, S, or T; $X_5$ is M, L, or F; and $X_6$ is D or A; (d) a CDR-L1 comprising $X_1SX_2QX_3LX_4NX_5X_6NX_7X_8NYLX_9$ (SEQ ID NO: 54), wherein: $X_1$ is K or R; $X_2$ is S or R; $X_3$ is S or I; $X_4$ is L or F; $X_5$ is S or T; $X_6$ is G or E; $X_7$ is Q or L; $X_8$ is K or R; and $X_9$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QX_1X_2X_3X_4X_5PX_6X_7$ (SEQ ID NO: 71), wherein $X_1$ is N or D; $X_2$ is D, G, N, or A; $X_3$ is Y or F; $X_4$ is F, S, I, or Y; $X_5$ is Y or F; $X_6$ is L or F; and $X_7$ is T or P.

In certain embodiments, an anti-CLDN18.2 antibody provided herein (or antigen binding fragment thereof) comprises: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9X_{10}X_{11}X_{12}X_{13}X_{14}KG$ (SEQ ID NO: 30), wherein X is Y, E, T, H, or N; $X_2$ is S, N, D, Y, or I; $X_3$ is S, P, or I; $X_4$ is G, N, K, R, or Y; $X_5$ is S, N, G, or Y; $X_6$ is S, G, T, N, or D; $X_7$ is N, T, V, Y, I, or P; $X_8$ is I, T, or F; $X_9$ is Y, H, or N; $X_{10}$ is Y, or S; $X_{11}$ is A, N, P, T, or V; $X_{12}$ is D, Q, or E; $X_{13}$ is T, K, S, or R; and $X_{14}$ is V, F, M, or L; (c) a CDR-H3 comprising $X_1X_2X_3GNX_4X_5X_6Y$ (SEQ ID NO: 43), wherein: $X_1$ is I, F, P, A, Q, or H; $X_2$ is A, Y, V, T; $X_3$ is R or Y; $X_4$ is A, V, S, or T; $X_5$ is M, L, or F; and $X_6$ is D or A; (d) a CDR-L1 comprising $X_1SX_2QX_3LX_4NX_5X_6NX_7X_8NYLX_9$ (SEQ ID NO: 54), wherein: $X_1$ is K or R; $X_2$ is S or R; $X_3$ is S or I; $X_4$ is L or F; $X_5$ is S or T; $X_6$ is G or E; $X_7$ is Q or L; $X_8$ is K or R; and $X_9$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QX_1X_2X_3X_4X_5PX_6X_7$ (SEQ ID NO: 71), wherein $X_1$ is N or D; $X_2$ is D, G, N, or A; $X_3$ is Y or F; $X_4$ is F, S, I, or Y; $X_5$ is Y or F; $X_6$ is L or F; and $X_7$ is T or P.

In certain embodiments, an anti-CLDN18.2 antibody provided herein (or antigen binding fragment thereof) comprises one, two, three, four, five, or six complementarity determining region (CDR) sequences selected from the group consisting of: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9X_{10}X_{11}X_{12}X_{13}X_{14}KG$ (SEQ ID NO: 30) wherein: $X_1$ is Y, E, T, H, N, or F; $X_2$ is S, N, Y, or I; $X_3$ is S, P, or I; $X_4$ is G, K, R, or Y; $X_5$ is S, G, or Y; $X_6$ is S, G, T, N, or D; $X_7$ is N, T, Y, S, I, or P; $X_8$ is I, T, or F; $X_9$ is Y, H, or N; $X_{10}$ is Y or C; $X_{11}$ is A, N, P, T, or V; $X_{12}$ is D, Q, or E; $X_{13}$ is T, K, S, or R; and $X_{14}$ is V, F, M, or L; (c) a CDR-H3 comprising $X_1X_2X_3GNX_4X_5X_6Y$ (SEQ ID NO: 43), wherein: $X_1$ is I, F, P, A, Q, or H; $X_2$ is A, Y, V, T; $X_3$ is R or Y; $X_4$ is A, V, S, or T; $X_5$ is M, L, or F; and $X_6$ is D or A; (d) a CDR-L1 comprising $KSX_1QX_2LX_3NX_4X_5NX_6X_7NYLX_8$ (SEQ ID NO: 116), wherein $X_1$ is S or R; $X_2$ is S or I; $X_3$ is L or F; $X_4$ is S or T; $X_5$ is G or E; $X_6$ is Q or L; $X_7$ is K or R; and $X_8$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QNX_2X_3X_4X_5PX_6T$ (SEQ ID NO: 117), wherein: $X_2$ is D, G, N, or A; $X_3$ is Y or F; $X_4$ is F, S, I, or Y; $X_5$ is Y or F; and $X_6$ is L or F.

In certain embodiments, an anti-CLDN18.2 antibody provided herein (or antigen binding fragment thereof) comprises: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9X_{10}X_{11}X_{12}X_{13}X_{14}KG$ (SEQ ID NO: 30), wherein X is Y, E, T, H, or N; $X_2$ is S, N, D, Y, or I; $X_3$ is S, P, or I; $X_4$ is G, N, K, R, or Y; $X_5$ is S, N, G, or Y; $X_6$ is S, G, T, N, or D; $X_7$ is N, T, V, Y, I, or P; $X_8$ is I, T, or F; $X_9$ is Y, H, or N; $X_{10}$ is Y, or S; $X_{11}$ is A, N, P, T, or V; $X_{12}$ is D, Q, or E; $X_{13}$ is T, K, S, or R; and $X_{14}$ is V, F, M, or L; (c) a CDR-H3 comprising $X_1X_2X_3GNX_4X_5X_6Y$ (SEQ ID NO: 43), wherein: $X_1$ is I, F, P, A, Q, or H; $X_2$ is A, Y, V, T; $X_3$ is R or Y; $X_4$ is A, V, S, or T; $X_5$ is M, L, or F; and $X_6$ is D or A; (d) a CDR-L1 comprising $X_1SX_2QX_3LX_4NX_5X_6NX_7X_8NYLX_9$ (SEQ ID NO: 54), wherein $X_1$ is K or R; $X_2$ is S or R; $X_3$ is S or I; $X_4$ is L or F; $X_5$ is S or T; $X_6$ is G or E; $X_7$ is Q or L; $X_8$ is K or R; and $X_9$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QX_1X_2X_3X_4X_5PX_6X_7$ (SEQ ID NO: 71), wherein $X_1$ is N or D; $X_2$ is D, G, N, or A; $X_3$ is Y or F; $X_4$ is F, S, I, or Y; $X_5$ is Y or F; $X_6$ is L or F; and $X_7$ is T or P.

In certain embodiments, an anti-CLDN18.2 antibody provided herein (or antigen binding fragment thereof) comprises: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9X_{10}X_{11}X_{12}X_{13}X_{14}KG$ (SEQ ID NO: 30), wherein X is Y, E, T, H, or N; $X_2$ is S, N, D, Y, or I; $X_3$ is S, P, or I; $X_4$ is G, N, K, R, or Y; $X_5$ is S, N, G, or Y; $X_6$ is S, G, T, N, or D; $X_7$ is N, T, V, Y, I, or P; $X_8$ is I, T, or F; $X_9$ is Y, H, or N; $X_{10}$ is Y, or S; $X_{11}$ is A, N, P, T, or V; $X_{12}$ is D, Q, or E; $X_{13}$ is T, K, S, or R; and $X_{14}$ is V, F, M, or L; (c) a CDR-H3 comprising $X_1X_2X_3GNX_4X_5X_6Y$ (SEQ ID NO: 43), wherein: $X_1$ is I, F, P, A, Q, or H; $X_2$ is A, Y, V, T; $X_3$ is R or Y; $X_4$ is A, V, S, or T; $X_5$ is M, L, or F; and $X_6$ is D or A; (d) a CDR-L1 comprising $X_1SX_2QX_3LX_4NX_5X_6NX_7X_8NYLX_9$ (SEQ ID NO: 54), wherein $X_1$ is K or R; $X_2$ is S or R; $X_3$ is S or I; $X_4$ is L or F; $X_5$ is S or T; $X_6$ is G or E; $X_7$ is Q or L; $X_8$ is K or R; and $X_9$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QX_1X_2X_3X_4X_5PX_6X_7$ (SEQ ID NO: 71), wherein $X_1$ is N or D; $X_2$ is D, G, N, or A; $X_3$ is Y or F; $X_4$ is F, S, I, or Y; $X_5$ is Y or F; $X_6$ is L or F; and $X_7$ is T or P.

In certain embodiments, an anti-CLDN18.2 antibody provided herein (or antigen binding fragment thereof) comprises one, two, three, four, five, or six complementarity determining region (CDR) sequences selected from the group consisting of: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9YX_{10}X_{11}X_{12}X_{13}KG$ (SEQ ID NO: 118), wherein $X_1$ is Y, E, T, H, or N; $X_2$ is S, N, Y, or I; $X_3$ is S, P, or I; $X_4$ is G, K, R, or Y; $X_5$ is S, G, or Y; $X_6$ is S, G, T, N, or D; $X_7$ is N, T, Y, I, or P; $X_8$ is I, T, or F; $X_9$ is Y, H, or N; $X_{10}$ is A, N, P, T, or V; $X_{11}$ is D, Q, or E; $X_{12}$ is T, K, S, or R; and $X_{13}$ is V, F, M, or L; (c) a CDR-H3 comprising $X_1X_2X_3GNX_4X_5X_6Y$ (SEQ ID NO: 43), wherein $X_1$ is I, F, A, Q, or H; $X_2$ is A, Y, V, T; $X_3$ is R or Y; $X_4$ is A, S, or T; $X_5$ is M, L, or F; and $X_6$ is D or A; (d) a CDR-L1 comprising $KSX_1QX_2LX_3NX_4X_5NQX_6NYLX_7$ (SEQ ID NO: 119), wherein $X_1$ is S or R; $X_2$ is S or I; $X_3$ is L or F; $X_4$ is S or T; $X_5$ is G or E; $X_6$ is K or R; and $X_7$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QNX_1X_2X_3X_4PX_5T$ (SEQ ID NO: 120), wherein $X_1$ is D, G, N, or A; $X_2$ is Y or F; $X_3$ is F, S, I, or Y; $X_4$ is Y or F; and $X_5$ is L or F.

In certain embodiments, an anti-CLDN18.2 antibody provided herein (or antigen binding fragment thereof) comprises: (a) a CDR-H1 comprising $GX_1X_2FX_3X_4X_5X_6X_7X_8$ (SEQ ID NO: 11), wherein $X_1$ is F or Y; $X_2$ is T or S; $X_3$ is T or S; $X_4$ is D, G, V, N, or S; $X_5$ is Y, W, or N; $X_6$ is G, N, S, or A; $X_7$ is M or I; and $X_8$ is F, H, S, Y, or N; (b) a CDR-H2 comprising $X_1IX_2X_3X_4X_5X_6X_7X_8X_9YX_{10}X_{11}X_{12}X_{13}KG$ (SEQ ID NO: 118), wherein $X_1$ is Y, E, T, H, or N; $X_2$ is S, N, Y, or I; $X_3$ is S, P, or I; $X_4$ is G, K, R, or Y; $X_5$ is S, G, or Y; $X_6$ is S, G, T, N, or D; $X_7$ is N, T, Y, I, or P; $X_8$ is I, T, or F; $X_9$ is Y, H, or N; $X_{10}$ is A, N, P, T, or V; $X_{11}$ is D, Q, or E; $X_{12}$ is T, K, S, or R; and $X_{13}$ is V, F, M, or L; (c) a CDR-H3 comprising $X_1X_2X_3GNX_4X_5X_6Y$ (SEQ ID NO: 43), wherein $X_1$ is I, F, A, Q, or H; $X_2$ is A, Y, V, T; $X_3$ is R or Y; $X_4$ is A, S, or T; $X_5$ is M, L, or F; and $X_6$ is D or A; (d) a CDR-L1 comprising $KSX_1QX_2LX_3NX_4X_5NQX_6NYLX_7$ (SEQ ID NO: 119), wherein $X_1$ is S or R; $X_2$ is S or I; $X_3$ is L or F; $X_4$ is S or T; $X_5$ is G or E; $X_6$ is K or R; and $X_7$ is T, A, or S; (e) a CDR-L2 comprising $WX_1STRX_2S$ (SEQ ID NO: 58), wherein $X_1$ is A or T; and $X_2$ is E or D; and (f) a CDR-L3 comprising $QNX_1X_2X_3X_4PX_5T$ (SEQ ID NO: 120), wherein $X_1$ is D, G, N, or A; $X_2$ is Y or F; $X_3$ is F, S, I, or Y; $X_4$ is Y or F; and $X_5$ is L or F.

In certain embodiments, provided is an anti-CLDN18.2 antibody (or antigen-binding fragment thereof) that specifically binds CLDN18.2 and competes for binding to CLDN18.2 with a second anti-CLDN18.2 antibody that comprises (a) a CDR-H1 comprising an amino acid sequence set forth in any one of SEQ ID NOs: 1-10; (b) a CDR-H2 comprising an amino acid sequence set forth in any one of SEQ ID NOs: 12-29 (c) a CDR-H3 comprising an amino acid sequence set forth in any one of SEQ ID NOs: 31-42; (d) a CDR-L1 comprising an amino acid sequence set forth in any one of SEQ ID NOs: 44-53; (e) a CDR-L2 comprising an amino acid sequence set forth in any one of SEQ ID NOs: 55-57; and (f) a CDR-L3 comprising an amino acid sequence set forth in any one of SEQ ID NOs: 59-70.

In certain embodiments, provided is an anti-CLDN18.2 antibody (or antigen-binding fragment thereof) that specifically binds to the same epitope of CLDN18.2 as a second anti-CLDN18.2 antibody that comprises (a) a CDR-H1 comprising an amino acid sequence set forth in anyone of SEQ ID NOs: 1-10; (b) a CDR-H2 comprising an amino acid sequence set forth in any one of SEQ ID NOs: 12-29 (c) a CDR-H3 comprising an amino acid sequence set forth in any one of SEQ ID NOs: 31-42; (d) a CDR-L1 comprising an amino acid sequence set forth in any one of SEQ ID NOs: 44-53; (e) a CDR-L2 comprising an amino acid sequence set forth in any one of SEQ ID NOs: 55-57; and (f) a CDR-L3 comprising an amino acid sequence set forth in any one of SEQ ID NOs: 59-70.

In certain embodiments, the anti-CLDN18.2 antibody (or antigen binding fragment thereof) comprises one, two, three, four, five, or six complementarity determining region (CDR) sequences selected from the group consisting of: (a) a CDR-H1 comprising an amino acid sequence set forth in any one of SEQ ID NOs: 1-10 or a variant thereof comprising up to about 5 (such as about any of 1, 2, 3, 4, or 5) amino acid substitutions; (b) a CDR-H2 comprising an amino acid sequence set forth in any one of SEQ ID NOs: 12-29 or a variant thereof comprising up to about 5 (such as about any of 1, 2, 3, 4, or 5) amino acid substitutions (c) a CDR-H3 comprising an amino acid sequence set forth in any one of SEQ ID NOs: 31-42 or a variant thereof comprising up to about 5 (such as about any of 1, 2, 3, 4, or 5) amino acid substitutions; (d) a CDR-L1 comprising an amino acid sequence set forth in any one of SEQ ID NOs: 44-53 or a variant thereof comprising up to about 5 (such as about any of 1, 2, 3, 4, or 5) amino acid substitutions; (e) a CDR-L2 comprising an amino acid sequence set forth in any one of SEQ ID NOs: 55-57 or a variant thereof comprising up to about 5 (such as about any of 1, 2, 3, 4, or 5) amino acid substitutions; and (f) a CDR-L3 comprising an amino acid sequence set forth in any one of SEQ ID NOs: 59-70 or a variant thereof comprising up to about 5 (such as about any of 1, 2, 3, 4, or 5) amino acid substitutions.

In certain embodiments, the anti-CLDN18.2 antibody (or antigen binding fragment thereof) comprises (a) a CDR-H1 comprising an amino acid sequence set forth in any one of SEQ ID NOs: 1-10 or a variant thereof comprising up to about 5 (such as about any of 1, 2, 3, 4, or 5) amino acid substitutions; (b) a CDR-H2 comprising an amino acid sequence set forth in any one of SEQ ID NOs: 12-29 or a variant thereof comprising up to about 5 (such as about any of 1, 2, 3, 4, or 5) amino acid substitutions (c) a CDR-H3 comprising an amino acid sequence set forth in any one of SEQ ID NOs: 31-42 or a variant thereof comprising up to about 5 (such as about any of 1, 2, 3, 4, or 5) amino acid substitutions; (d) a CDR-L1 comprising an amino acid sequence set forth in any one of SEQ ID NOs: 44-53 or a variant thereof comprising up to about 5 (such as about any of 1, 2, 3, 4, or 5) amino acid substitutions; (e) a CDR-L2 comprising an amino acid sequence set forth in any one of SEQ ID NOs: 55-57 or a variant thereof comprising up to about 5 (such as about any of 1, 2, 3, 4, or 5) amino acid substitutions; and (f) a CDR-L3 comprising an amino acid sequence set forth in any one of SEQ ID NOs: 59-70 or a variant thereof comprising up to about 5 (such as about any of 1, 2, 3, 4, or 5) amino acid substitutions.

In certain embodiments, the anti-CLDN18.2 antibody (or antigen binding fragment thereof) comprises a CDR-H3 comprising an amino acid sequence set forth in any one of SEQ ID NOs: 31-42 and/or a CDR-L3 comprising an amino acid sequence set forth in any one of SEQ ID NOs: 59-70.

In certain embodiments, the anti-CLDN18.2 antibody (or antigen binding fragment thereof) comprises one, two, three, four, five, or six complementarity determining region (CDR) sequences selected from the group consisting of: (a) a CDR-H1 comprising an amino acid sequence set forth in any one of SEQ ID NOs: 1-10; (b) a CDR-H2 comprising an amino acid sequence set forth in any one of SEQ ID NOs: 12-29 (c) a CDR-H3 comprising an amino acid sequence set forth in any one of SEQ ID NOs: 31-42; (d) a CDR-L1 comprising an amino acid sequence set forth in any one of SEQ ID NOs: 44-53; (e) a CDR-L2 comprising an amino acid sequence set forth in any one of SEQ ID NOs: 55-57; and (f) a CDR-L3 comprising an amino acid sequence set forth in any one of SEQ ID NOs: 59-70.

In certain embodiments, the anti-CLDN18.2 antibody (or antigen binding fragment thereof) comprises: (a) a CDR-H1 comprising an amino acid sequence set forth in any one of SEQ ID NOs: 1-10; (b) a CDR-H2 comprising an amino acid sequence set forth in any one of SEQ ID NOs: 12-29 (c) a CDR-H3 comprising an amino acid sequence set forth in any one of SEQ ID NOs: 31-42; (d) a CDR-L1 comprising an amino acid sequence set forth in any one of SEQ ID NOs: 44-53; (e) a CDR-L2 comprising an amino acid sequence set forth in any one of SEQ ID NOs: 55-57; and (f) a CDR-L3 comprising an amino acid sequence set forth in any one of SEQ ID NOs:59-70.

In certain embodiments, an anti-CLDN18.2 antibody provided herein (or antigen binding fragment thereof) comprises one, two, three, four, five, or six complementarity determining region (CDR) sequences selected from the group consisting of: (a) a CDR-H1 comprising GFX$_1$FSDYGMX$_2$(SEQ ID NO: 121), wherein X$_1$ is T or S; and X$_2$ is H or Y; (b) a CDR-H2 comprising X$_1$ISSGSSX$_2$IYX$_3$ADTX$_4$KG (SEQ ID NO: 122), wherein X$_1$ is Y, H, or F; X$_2$ is S or T; X$_3$ is Y or C; and X$_4$ is V or M; (c) a CDR-H3 comprising X$_1$ARGNX$_4$MDY (SEQ ID NO: 123), wherein X$_1$ is I or F; and X$_4$ is T or A; (d) a CDR-L1 comprising KSSQSLLNSGNX$_1$X$_2$NYLX$_3$ (SEQ ID NO: 124), wherein X$_1$ is Q or L; X$_2$ is R or K; and X$_3$ is T or A; (e) a CDR-L2 comprising WASTRES (SEQ ID NO: 55); and (f) a CDR-L3 comprising QNX$_1$YX$_2$YPLT (SEQ ID NO: 125) wherein: X$_1$ is G or D; and X$_2$ is S or F.

In certain embodiments, an anti-CLDN18.2 antibody provided herein (or antigen binding fragment thereof) comprises (a) a CDR-H1 comprising GFX$_1$FSDYGMX$_2$(SEQ ID NO: 121), wherein X$_1$ is T or S; and X$_2$ is H or Y; (b) a CDR-H2 comprising X$_1$ISSGSSX$_2$IYX$_3$ADTX$_4$KG (SEQ ID NO: 122), wherein X$_1$ is Y, H, or F; X$_2$ is S or T; X$_3$ is Y or C; and X$_4$ is V or M; (c) a CDR-H3 comprising X$_1$ARGNX$_4$MDY (SEQ ID NO: 123), wherein X$_1$ is I or F; and X$_4$ is T or A; (d) a CDR-L1 comprising KSSQSLLNSGNX$_1$X$_2$NYLX$_3$ (SEQ ID NO: 124), wherein X$_1$ is Q or L; X$_2$ is R or K; and X$_3$ is T or A; (e) a CDR-L2 comprising WASTRES (SEQ ID NO: 55); and (f) a CDR-L3 comprising QNX$_1$YX$_2$YPLT (SEQ ID NO: 125) wherein: X$_1$ is G or D; and X$_2$ is S or F.

In certain embodiments, provided is an anti-CLDN18.2 antibody (or antigen-binding fragment thereof) that specifically binds CLDN18.2 and competes for binding to CLDN18.2 with a second anti-CLDN18.2 antibody that comprises (a) a CDR-H1 comprising an amino acid sequence set forth in any one of SEQ ID NOs: 2, 7, and 6; (b) a CDR-H2 comprising an amino acid sequence set forth in any one of SEQ ID NOs:17, 22, and 29; (c) a CDR-H3 comprising an amino acid sequence set forth in SEQ ID NO: 31 or 37; (d) a CDR-L1 comprising an amino acid sequence set forth in any one of SEQ ID NOs: 44, 48, and 53; (e) a CDR-L2 comprising an amino acid sequence set forth in SEQ ID NO: 55; and (f) a CDR-L3 comprising an amino acid sequence set forth in any one of SEQ ID NOs: 59, 60, and 64.

In certain embodiments, provided is an anti-CLDN18.2 antibody (or antigen-binding fragment thereof) that specifically binds to the same epitope of CLDN18.2 as a second anti-CLDN18.2 antibody that comprises (a) a CDR-H1 comprising an amino acid sequence set forth in anyone of SEQ ID NOs:2, 7, and 6; (b) a CDR-H2 comprising an amino acid sequence set forth in any one of SEQ ID NOs: 17, 22, and 29; (c) a CDR-H3 comprising an amino acid sequence set forth in SEQ ID NO: 31 or 37; (d) a CDR-L1 comprising an amino acid sequence set forth in any one of SEQ ID NOs: 44, 48, and 53; (e) a CDR-L2 comprising an amino acid sequence set forth in SEQ ID NO: 55; and (f) a CDR-L3 comprising an amino acid sequence set forth in any one of SEQ ID NOs: 59, 60, and 64.

In certain embodiments, the anti-CLDN18.2 antibody (or antigen binding fragment thereof) comprises one, two, three, four, five, or six complementarity determining region (CDR) sequences selected from the group consisting of: (a) a CDR-H1 comprising an amino acid sequence set forth in any one of SEQ ID NOs: 2, 7, and 6 or a variant thereof comprising up to about 5 (such as about any of 1, 2, 3, 4, or 5) amino acid substitutions; (b) a CDR-H2 comprising an amino acid sequence set forth in any one of SEQ ID NOs: 17, 22, and 29 or a variant thereof comprising up to about 5 (such as about any of 1, 2, 3, 4, or 5) amino acid substitutions (c) a CDR-H3 comprising an amino acid sequence set forth in SEQ ID NO: 31 or 37 or a variant thereof comprising up to about 5 (such as about any of 1, 2, 3, 4, or 5) amino acid substitutions; (d) a CDR-L1 comprising an amino acid sequence set forth in any one of SEQ ID NOs: 44, 48, and 53 or a variant thereof comprising up to about 5 (such as about any of 1, 2, 3, 4, or 5) amino acid substitutions; (e) a CDR-L2 comprising an amino acid sequence set forth in SEQ ID NO: 55 or a variant thereof comprising up to about 5 (such as about any of 1, 2, 3, 4, or 5) amino acid substitutions; and (f) a CDR-L3 comprising an amino acid sequence set forth in any one of SEQ ID NOs: 59, 60, and 64 or a variant thereof comprising up to about 5 (such as about any of 1, 2, 3, 4, or 5) amino acid substitutions.

In certain embodiments, the anti-CLDN18.2 antibody (or antigen binding fragment thereof) comprises (a) a CDR-H1 comprising an amino acid sequence set forth in any one of SEQ ID NOs: 2, 7, and 6 or a variant thereof comprising up to about 5 (such as about any of 1, 2, 3, 4, or 5) amino acid substitutions; (b) a CDR-H2 comprising an amino acid sequence set forth in any one of SEQ ID NOs: 17, 22, and 29 or a variant thereof comprising up to about 5 (such as about any of 1, 2, 3, 4, or 5) amino acid substitutions (c) a CDR-H3 comprising an amino acid sequence set forth in SEQ ID NO: 31 or 37 or a variant thereof comprising up to about 5 (such as about any of 1, 2, 3, 4, or 5) amino acid substitutions; (d) a CDR-L1 comprising an amino acid sequence set forth in any one of SEQ ID NOs: 44, 48, and 53 or a variant thereof comprising up to about 5 (such as about any of 1, 2, 3, 4, or 5) amino acid substitutions; (e) a CDR-L2 comprising an amino acid sequence set forth in SEQ ID NO: 55 or a variant thereof comprising up to about 5 (such as about any of 1, 2, 3, 4, or 5) amino acid substitutions; and (f) a CDR-L3 comprising an amino acid sequence set forth in any one of SEQ ID NOs: 59, 60, and 64 or a variant thereof comprising up to about 5 (such as about any of 1, 2, 3, 4, or 5) amino acid substitutions.

In certain embodiments, the anti-CLDN18.2 antibody (or antigen binding fragment thereof) comprises a CDR-H3 comprising an amino acid sequence set forth in SEQ ID NO: 31 or 37 and/or a CDR-L3 comprising an amino acid sequence set forth in any one of SEQ ID NOs: 59, 60, and 64.

In certain embodiments, the anti-CLDN18.2 antibody (or antigen binding fragment thereof) comprises one, two, three, four, five, or six complementarity determining region (CDR) sequences selected from the group consisting of: (a) a CDR-H1 comprising an amino acid sequence set forth in any one of SEQ ID NOs: 2, 7, and 6; (b) a CDR-H2 comprising an amino acid sequence set forth in any one of SEQ ID NOs: 17, 22, and 29; (c) a CDR-H3 comprising an amino acid sequence set forth in SEQ ID NO: 31 or 37; (d) a CDR-L1 comprising an amino acid sequence set forth in any one of SEQ ID NOs: 44, 48, and 53; (e) a CDR-L2 comprising an amino acid sequence set forth in SEQ ID NO: 55; and (f) a CDR-L3 comprising an amino acid sequence set forth in any one of SEQ ID NOs: 59, 60, and 64.

In certain embodiments, the anti-CLDN18.2 antibody (or antigen binding fragment thereof) comprises: (a) a CDR-H1 comprising an amino acid sequence set forth in any one of SEQ ID NOs: 2, 7, and 6; (b) a CDR-H2 comprising an amino acid sequence set forth in any one of SEQ ID NOs: 17, 22, and 29; (c) a CDR-H3 comprising an amino acid sequence set forth in SEQ ID NO: 31 or 37; (d) a CDR-L1 comprising an amino acid sequence set forth in any one of SEQ ID NOs: 44, 48, and 53; (e) a CDR-L2 comprising an amino acid sequence set forth in SEQ ID NO: 55; and (f) a CDR-L3 comprising an amino acid sequence set forth in any one of SEQ ID NOs: 59, 60, and 64.

In certain embodiments, an anti-CLDN18.2 antibody provided herein comprises a CDR-H3 that comprises (such as consists of) 4 amino acids, less than 4 amino acids, or 3 amino acids. In some embodiments, an anti-CLDN18.2 antibody comprising a CDR-H3 that comprises (such as consists of) 4 amino acids, less than 4 amino acids, or 3 amino acids specifically binds CLDN18.1 and CLDN18.2.

In certain embodiments, an anti-CLDN18.2 antibody provided herein (or antigen binding fragment thereof) comprises one, two, three, four, five, or six complementarity determining region (CDR) sequences selected from the group consisting of: (a) a CDR-H1 comprising GYTFX$_1$X$_2$YX$_3$X$_4$H (SEQ ID NO: 139), wherein: X$_1$ is T or I; X$_2$ is S or N; X$_3$ is L or V; and X$_4$ is I or M; (b) a CDR-H2 comprising YINPX$_1$X$_2$DGTKYNEKFKG (SEQ ID NO: 140), wherein: X$_1$ is Y or F; and X$_2$ is N or D; (c) a CDR-H3 comprising (such as consisting of) 4 amino acids, less than 4 amino acids, or three amino acids; (d) a CDR-L1 comprising KSSQSLLNSGNQKNYLT (SEQ ID NO: 44); (e) a CDR-L2 comprising WASX$_1$RX$_2$S (SEQ ID NO: 141), wherein X$_1$ is T or I; and X$_2$ is A or D; and (f) a CDR-L3 comprising LNDYSFPLT (SEQ ID NO: 131). In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, an anti-CLDN antibody provided herein (or antigen binding fragment thereof) comprises (a) a CDR-H1 comprising GYTFX$_1$X$_2$YX$_3$X$_4$H (SEQ ID NO: 139), wherein: X$_1$ is T or I; X$_2$ is S or N; X$_3$ is L or V; and X$_4$ is I or M; (b) a CDR-H2 comprising YINPX$_1$X$_2$DGTKYNEKFKG (SEQ ID NO: 140), wherein: X$_1$ is Y or F; and X$_2$ is N or D; (c) a CDR-H3 comprising (such as consisting of) 4 amino acids, less than 4 amino acids, or three amino acids; (d) a CDR-L1 comprising KSSQSLLNSGNQKNYLT (SEQ ID NO: 44); (e) a CDR-L2 comprising WASX$_1$RX$_2$S (SEQ ID NO: 141), wherein X$_1$ is T or I; and X$_2$ is A or D; and (f) a CDR-L3 comprising LNDYSFPLT (SEQ ID NO: 131). In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, provided is an anti-CLDN18.2 antibody (or antigen-binding fragment thereof) that specifically binds CLDN18.2 and competes for binding to CLDN18.2 with a second anti-CLDN18.2 antibody that comprises (a) a CDR-H1 comprising an amino acid sequence set forth in SEQ ID NO: 128 or 132; (b) a CDR-H2 comprising an amino acid sequence set forth in SEQ ID NO: 129 or 133 (c) a CDR-H3 comprising (such as consisting of) 4 amino acids, less than 4 amino acids, or three amino acids; (d) a CDR-L1 comprising an amino acid sequence set forth in SEQ ID NO: 44; (e) a CDR-L2 comprising an amino acid sequence set forth in SEQ ID NO: 130 or 134; and (f) a CDR-L3 comprising an amino acid sequence set forth in SEQ ID NO: 131. In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, provided is an anti-CLDN18.2 antibody (or antigen-binding fragment thereof) that specifically binds to the same epitope of CLDN18.2 as a second anti-CLDN18.2 antibody that comprises (a) a CDR-H1 comprising an amino acid sequence set forth in SEQ ID NO: 128 or 132; (b) a CDR-H2 comprising an amino acid sequence set forth in SEQ ID NO: 129 or 133 (c) a CDR-H3 comprising (such as consisting of) 4 amino acids, less than 4 amino acids, or three amino acids; (d) a CDR-L1 comprising an amino acid sequence set forth in SEQ ID NO: 44; (e) a CDR-L2 comprising an amino acid sequence set forth in SEQ ID NO: 130 or 134; and (f) a CDR-L3 comprising an amino acid sequence set forth in SEQ ID NO: 131. In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, the anti-CLDN18.2 antibody (or antigen binding fragment thereof) comprises one, two, three, four, five, or six complementarity determining region (CDR) sequences selected from the group consisting of: (a) a CDR-H1 comprising an amino acid sequence set forth in SEQ ID NO: 128 or 132 or a variant thereof comprising up to about 5 (such as about any of 1, 2, 3, 4, or 5) amino acid substitutions; (b) a CDR-H2 comprising an amino acid sequence set forth in SEQ ID NO: 129 or 133 or a variant thereof comprising up to about 5 (such as about any of 1, 2, 3, 4, or 5) amino acid substitutions (c) a CDR-H3 comprising (such as consisting of) 4 amino acids, less than 4 amino acids, or three amino acids; (d) a CDR-L1 comprising an amino acid sequence set forth in SEQ ID NO: 44 or a variant thereof comprising up to about 5 (such as about any of 1, 2, 3, 4, or 5) amino acid substitutions; (e) a CDR-L2 comprising an amino acid sequence set forth in SEQ ID NO: 130 or 134 or a variant thereof comprising up to about 5 (such as about any of 1, 2, 3, 4, or 5) amino acid substitutions; and (f) a CDR-L3 comprising an amino acid sequence set forth in SEQ ID NO: 131 or a variant thereof comprising up to about 5 (such as about any of 1, 2, 3, 4, or 5) amino acid substitutions. In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, the anti-CLDN18.2 antibody (or antigen binding fragment thereof) comprises (a) a CDR-H1 comprising an amino acid sequence set forth in SEQ ID NO: 128 or 132 or a variant thereof comprising up to about 5 (such as about any of 1, 2, 3, 4, or 5) amino acid substitutions; (b) a CDR-H2 comprising an amino acid sequence set forth in SEQ ID NO: 129 or 133 or a variant thereof comprising up to about 5 (such as about any of 1, 2, 3, 4, or 5) amino acid substitutions (c) a CDR-H3 comprising (such as consisting of) 4 amino acids, less than 4 amino acids, or three amino acids; (d) a CDR-L1 comprising an amino acid sequence set forth in SEQ ID NO: 44 or a variant thereof comprising up to about 5 (such as about any of 1, 2, 3, 4, or 5) amino acid substitutions; (e) a CDR-L2 comprising an amino acid sequence set forth in SEQ ID NO: 130 or 134 or a variant thereof comprising up to about 5 (such as about any of 1, 2, 3, 4, or 5) amino acid substitutions; and (f) a CDR-L3 comprising an amino acid sequence set forth in SEQ ID NO: 131 or a variant thereof comprising up to about 5 (such as about any of 1, 2, 3, 4, or 5) amino acid substitutions. In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, the anti-CLDN18.2 antibody (or antigen binding fragment thereof) comprises a CDR-H3 comprising (such as consisting of) 4 amino acids, less than 4 amino acids, or three amino acids; and/or a CDR-L3 comprising an amino acid sequence set forth in any one of 59-70. In some embodiments, the CDR-H3 comprises (such as consists of) GDX$_1$, wherein X$_1$ is F or Y. In certain embodiments, the anti-CLDN18.2 antibody specifically binds CLDN18.1.

In certain embodiments, the anti-CLDN18.2 antibody (or antigen binding fragment thereof) comprises one, two, three, four, five, or six complementarity determining region (CDR) sequences selected from the group consisting of: (a) a CDR-H1 comprising an amino acid sequence set forth in SEQ ID NO: 128 or 132; (b) a CDR-H2 comprising an amino acid sequence set forth in SEQ ID NO: 129 or 133; (c) a CDR-H3 comprising the amino acid sequence GDF or GDY; (d) a CDR-L1 comprising an amino acid sequence set forth in SEQ ID NO: 44; (e) a CDR-L2 comprising an amino acid sequence set forth in SEQ ID NO: 130 or 134; and (f) a CDR-L3 comprising an amino acid sequence set forth in SEQ ID NO: 131. In certain embodiments, the anti-CLDN18.2 antibody specifically binds CLDN18.1.

In certain embodiments, the anti-CLDN18.2 antibody (or antigen binding fragment thereof comprises: (a) CDR-H1 comprising an amino acid sequence set forth in SEQ ID NO: 128 or 132; (b) a CDR-H2 comprising an amino acid sequence set forth in SEQ ID NO: 129 or 133; (c) a CDR-H3 comprising the amino acid sequence GDF or GDY; (d) a CDR-L1 comprising an amino acid sequence set forth in SEQ ID NO: 44; (e) a CDR-L2 comprising an amino acid sequence set forth in SEQ ID NO: 130 or 134; and (f) a CDR-L3 comprising an amino acid sequence set forth in SEQ ID NO: 131. In certain embodiments, the anti-CLDN18.2 antibody specifically binds CLDN18.1.

The amino acid sequences of SEQ ID NOs: 1-10, 11-29, 31-42, 44-53, 55-57, 59-70, and 128-134 are provided in Table 1 below.

TABLE 1

| | | | |
|---|---|---|---|
| GFTFSDYGMF (SEQ ID NO: 1) | HISSGSNIIHYADTLKG (SEQ ID NO: 19) | FARGNTMDY (SEQ ID NO: 37) | WASTRDS (SEQ ID NO: 56) |
| GFTFSDYGMH (SEQ ID NO: 2) | YISSGSNTFYYTDTVKG (SEQ ID NO: 20) | FTRGNALDY (SEQ ID NO: 38) | TSTRES (SEQ ID NO: 57) |
| GYSFTGYNIH (SEQ ID NO: 3) | YISSGSNTIYYADTVKG (SEQ ID NO: 21) | FVRGNALDY (SEQ ID NO: 39) | QNDYFYPLT (SEQ ID NO: 59) |
| GYTFTVWSMS (SEQ ID NO: 4) | HISSGSSTIYYADTMKG (SEQ ID NO: 22) | FARGNTLDY (SEQ ID NO: 40) | QNGYSYPLT (SEQ ID NO: 60) |
| GFTFSNNAMS (SEQ ID NO: 5) | YISSGSSTIHYVDTMKG (SEQ ID NO: 23) | FARGNAMDY (SEQ ID NO: 41) | QDGYFYPFP (SEQ ID NO: 61) |
| GFTFSDYGMY (SEQ ID NO: 6) | YISSGSSTIYYADTVKG (SEQ ID NO: 24) | HVRGNSFDY (SEQ ID NO: 42) | QNDFIYPFT (SEQ ID NO: 62) |
| GFSFSDYGMH (SEQ ID NO: 7) | YISSGSSPIYYADTVKG (SEQ ID NO: 25) | KSSQSLLNSGNQKNYLT (SEQ ID NO: 44) | QNNYFYPFT (SEQ ID NO: 63) |
| GFT FSNYAMS (SEQ ID NO: 8) | YISSGSNNIYYADTVKG (SEQ ID NO: 26) | RSSQSLLNSGNQRNYLT (SEQ ID NO: 45) | QNDYSYPLT (SEQ ID NO: 64) |
| GYTFTSWSIS (SEQ ID NO: 9) | EIYPRSDNIHYNEKFKG (SEQ ID NO: 27) | KSSQSLLNSGNLRNYLT (SEQ ID NO: 46) | QNAYSYPLT (SEQ ID NO: 65) |
| GYSFTGYNMN (SEQ ID NO: 10) | NINPYYSNTNYNQRFKG (SEQ ID NO: 28) | KSSQSLLNSGNQRNYLT (SEQ ID NO: 47) | QNAYSFPLT (SEQ ID NO: 66) |
| YISSGSSNIYYADTVKG (SEQ ID NO: 12) | FISSGSSTIYCADTVKG (SEQ ID NO: 29) | KSSQSLLNSGNQRNYLA (SEQ ID NO: 48) | QNDYIYPLT (SEQ ID NO: 67) |
| YINSGSSTIYYADTVKG (SEQ ID NO: 13) | IARGNAMDY (SEQ ID NO: 31) | KSSQSLFNTGNQKNYLT (SEQ ID NO: 49) | QNNYYYPLT (SEQ ID NO: 68) |
| YIDPNNGVTYSNQKFKG (SEQ ID NO: 14) | FARGNVLDY (SEQ ID NO: 32) | KSSQSLFNSGNQRNYLA (SEQ ID NO: 50) | QNNYIYPFT (SEQ ID NO: 69) |
| EIYPKSGNTHYNEKFKG (SEQ ID NO: 15) | PYYGNSFDY (SEQ ID NO: 33) | KSSQILLNSGNQKNYLT (SEQ ID NO: 51) | QNDYYYPFT (SEQ ID NO: 70) |
| TIIIGGTYTYYPDSVKG (SEQ ID NO: 16) | AYYGNSFAY (SEQ ID NO: 34) | KSRQSLFNSENQKNYLS (SEQ ID NO: 52) | GYTFISYLIH (SEQ ID NO: 128) |
| YISSGSSSIYYADTVKG (SEQ ID NO: 17) | QVYGNSFAY (SEQ ID NO: 35) | KSSQSLLNSGNLKNYLT (SEQ ID NO: 53) | YINPYNDGTKYNEKFKG (SEQ ID NO: 129) |

TABLE 1-continued

| | | | |
|---|---|---|---|
| YISSGSSTIYYADTMKG (SEQ ID NO: 18) | FVRGNSMDY (SEQ ID NO: 36) | WASTRES (SEQ ID NO: 55) | WASIRAS (SEQ ID NO: 130) |
| LNDYSFPLT (SEQ ID NO: 131) | GYTFTNYVMH (SEQ ID NO: 132) | YINPFDDGTKYNEKFKG (SEQ ID NO: 133) | WASTRDS (SEQ ID NO: 134) |

In some embodiments, the anti-CLDN18.2 antibody (or antigen binding fragment thereof) comprises a heavy chain variable domain (VH) comprising an amino acid sequence that is at least about 95%, 96%, 97%, 98%, 99%, or 100% identical to an amino acid sequence set forth in any one of SEQ ID NOs: 72-93 and 135-136 and/or a light chain variable domain (VL) comprising an amino acid sequence that is at least about 95, 96, 97%, 98%, 99%, or 100% identical to an amino acid sequence set forth in any one of SEQ ID NOs: 94-115 and 137-138. In some embodiments, the anti-CLDN18.2 antibody (or antigen binding fragment thereof) comprises a heavy chain variable domain (VH) comprising an amino acid sequence that is at least about 95, 96, 97%, 98%, 99%, or 100% identical to an amino acid sequence set forth in any one of SEQ ID NOs: 72-93 and 135-136 and alight chain variable domain (VL) comprising an amino acid sequence that is at least about 95%, 96%, 97%, 98%, 99% or 100% identical to an amino acid sequence set forth in any one of SEQ ID NOs: 94-115 and 137-138. The amino acid sequences of SEQ ID NOs: 72-115 are provided in Table 2 below:

TABLE 2

EVQLVESGGGLVKPGGSRKLSCAASGFTFSDYGMFWVRQAPEKGLEWVG
YISSGSSNIYYADTVKGRFTISRDNAKNTLFLQMISLRSEDTAMYYCAR
IARGNAMDYWGQGTSVTVSS
(SEQ ID NO: 72)

EVQLVESGGGLVKPGGSRKLSCAASGFTFSDYGMHWVRQAPEKGLEWIA
YINSGSSTIYYADTVKGRFTISRDNAKNTLFLQMISLRSEDTAMFYCAR
FARGNVLDYWGQGTSVTVSS
(SEQ ID NO: 73)

EVQLQQSGPALVKPGASVKMSCKASGYSFIGYNIHWVKQSHGKSLEWIG
YIDPNNGVTYSNQKFKGKATLTVDKSSSTAYMQLNSLTSEDSAVYYCAR
PYYGNSFDYWGQGTTLTVSS
(SEQ ID NO: 74)

QVQLQQSGAELARPGASVKLSCKASGYTFTVWSMSWVKQRTGQGLQWIG
EIYPKSGNTHYNEKFKGKATLTADKSSSTVYMQLSSLTSEDSAVYFCAR
AYYGNSFAYWGQGTLVTVPA
(SEQ ID NO: 75)

EVQLVESGGALVKSGGSLRLSCAASGFTFSNNAMSWIRQTPEKRLEWVA
TIIIGGTYTYYPDSVKGRFTISRDNAKNTLYLQMSSLRSEDTAFYYCAR
QVYGNSFAYWGQGTLVSVSA
(SEQ ID NO: 76)

EVQLVESGGGLVKPGGSRKLSCAASGFTFSDYGMHWVRQAPEKGLEWIA
YISSGSSSIYYADTVKGRFTMSRDNAKKTLFLQTTSLRSEDTAMYYCAR
IARGNAMDYWGQGTSVIVIS
(SEQ ID NO: 77)

EVQLVNSGGGLVKPGGSRKLSCAASGFTFSDYGMHWVRQAPEKGLEWVA
YISSGSSTIYYADTMKGRFTISRDNAKNTLFLQMISLRSEDTAMYYCAR
EVRGNSMDYWGQGTSVTVSS
(SEQ ID NO: 78)

EVQLVESGGGLVKPGGSRKLSCAASGFTFSDYGMHWVRQAPEKGLEWVA
HISSGSNIIHYADTLKGRFTISRDNAKNTLFLQMTSLRSEDTAMYYCAR
FARGNTMDYWGQGTSVTVSS
(SEQ ID NO: 79)

TABLE 2-continued

EVQLVESGGGLVKPGGSRKLSCAASGFTFSDYGMHWVRQAPEKGLEWVA
YISSGSSTIYYADTMKGRFTISRDNAKNTLFLQMTSLRSEDTAMYYCTR
FARGNTMDYWGQGTSVTVSS
(SEQ ID NO: 80)

EVQLVESGGGSVKPGGSRKLSCAASGFTFSDYGMHWVRQAPEKGLEWVA
YISSGSNTFYYTDTVKGRFTISRDNAKNTLFLQMTGLRSEDTAMYYCAR
FTRGNALDYWGQGTSVTVSS
(SEQ ID NO: 81)

EVQLVESGGGLVKPGGSRKLSCAASGFTFSDYGMYWVRQAPEKGLEWLA
YISSGSNTIYYADTVKGRFTISRDNAKNTLFLQMISLRSEDTAMYYCAR
IARGNAMDYWGQGTSVTVSS
(SEQ ID NO: 82)

EVQLVESGGGLVKPGGSRKLSCAASGFTFSDYGMHWVRQAPEKGLEWIA
HISSGSSTIYYADTMKGRFTISRDNAKNTLFLQMISLRSEDTAMYYCAR
EVRGNALDYWGQGTSVTVSS
(SEQ ID NO: 83)

EVQLVESGGGLVKPGGSRKLSCAASGFTFSDYGMHWVRQAPEKGLEWVA
YISSGSSTIHYVDTMKGRFTISRDNAKNTLFLQMISLRSEDTAMYYCAR
FARGNTLDYWGQGTSVTVSS
(SEQ ID NO: 84)

EVQLVESGGGLVKPGGSRKLSCAVSGFTFSDYGMYWVRQAPEKGLEWVA
YISSGSSTIYYADTVKGRFTMSRDNAKNTLFLQMISLRSEDTAMYYCAR
IARGNAMDYWGQGTSVTVSS
(SEQ ID NO: 85)

EVQLVESGGGLVKPGGSRKLSCAASGESFSDYGMHWVRQAPEKGLEWVA
HISSGSSTIYYADTMKGRFTISRDNAKNTLFLQMISLRSEDTAMYYCAR
FARGNTMDYWGQGTSVTVSS
(SEQ ID NO: 86)

EVQLVESGGGLVKPGGSRKLSCAASGFTFSDYGMHWVRQAPEKGLEWVA
YISSGSSPIYYADTVKGRFTISRDNAKNTLFLQMISLRSEDTAMYYCAR
FARGNAMDYWGQGTSVTVSS
(SEQ ID NO: 87)

EVQLVESGGGLVKPGGSRKLSCAASGFTFSDYGMHWVRQAPEKGLEWVA
YISSGSSTIYYADTMKGRFTISRDNAKNTLFLQMTSLRSEDTAMYYCAR
EVRGNSMDYWGQGTSVTVSS
(SEQ ID NO: 88)

EVQLVESGGALVKPGGSLKLSCAASGFIFSNYAMSWIRQTPEKRLEWVA
TIIIGGTYTYYPDSVKGRFTISRDNAKNTLYLQMSSLRSEDTALYYCAR
QVYGNSFAYWGQGTLVIVSA
(SEQ ID NO: 89)

EVQLVESGGGLVKPGGSRKLSCAASGFTFSDYGMYWVRQAPEKGLEWLA
YISSGSNNIYYADTVKGRFTISRDNAKNTLFLQMTSLRSEDTAMYYCAR
IARGNAMDYWGQGTSVTVSS
(SEQ ID NO: 90)

QVQLQQSGAELARPGASVKLSCKASGYTFTSWSISWVKQRTGQGLEWIG
EIYPRSDNIHYNEKFKGKATLTADKSSSTVYMQLSSLTSEDSAVYFCAR
AYYGNSFAYWGQGTLVTVSA
(SEQ ID NO: 91)

EIQLQQSGAELVKPGTSVKISCKASGYSFTGYNMNWVKQSHGKSLEWIG
NINPYYSNINYNQRFKGKATLIVDKSSSTAYMQLNSLTSEDSAVYYCAR
HVRGNSFDYWGQGTTLTVSS
(SEQ ID NO: 92)

EVQLVESGGGLVKPGGSRKLSCAASGFTFSDYGMYWVRQAPEKGLEWVA
FISSGSSTIYCADTVKGRFTISRDNAKNTLFLQMISLRSEDTAMYYCAR
IARGNAMDYWGQGTSVTVSS
(SEQ ID NO: 93)

TABLE 2-continued

DIVMTQSPSSLTVTAGEKVTMSCKSSQSLLNSGNQKNYLTWYQQKPGQP
PKLLIYWASTRESGVPDRFTGSGSGTDFTLTISSVQAEDLAIYYCQNDY
FYPLTFGAGTKLELK
(SEQ ID NO: 94)

DIVMTQSPSSLTVTAGEKVTMSCRSSQSLLNSGNQRNYLTWYQQKPGHP
PKLLIYWASTRESGVPDRFTGSGSGTDFTLTISGVQAEDLAVYYCQNGY
SYPLTFGAGTKLEVK
(SEQ ID NO: 95)

DIVMTQSPSSLTVTAGEKVTMSCKSSQSLLNSGNLRNYLTWYQQKPGQP
PKLLIYWASTRESGVPDRFTGSGSGTDFTLTINSVQAEDLALYFCQDGY
FYPFPFGSGTKLVIK
(SEQ ID NO: 96)

DIVMTQSPSPLTVTAGEKATMSCKSSQSLLNSGNQRNYLTWYQQKPGQP
PKLLIYWASTRESGVPDRFTGSGSGTDFSLTISSVQAEDLAVYYCQNDF
IYPFTEGSGTKLEIK
(SEQ ID NO: 97)

DIVMTQSPSSLTVTAGEKVTMSCKSSQSLLNSGNQKNYLTWYQQKPGQP
PKLLIYWASTRESGVPDRFTGSGSGTDFTLTISSVQAEDLAVYYCQNNY
FYPFTEGSGTKLEIK
(SEQ ID NO: 98)

DIVMTQSPSSLTVTAGEKVTMSCKSSQSLLNSGNQRNYLAWYQQKPGQP
PKLLIYWASTRESGVPDRFTGSGSGTDFTLTISSVQAEDLAVYYCQNDY
SYPLTFGAGTKLELK
(SEQ ID NO: 99)

DIVMTQSPSSLTVTAGEKVTMSCKSSQSLLNSGNQKNYLTWYQQKPGQP
PKLLIYWASTRESGVPDRFTGSGSGTDFTLTISSVQAEDLTVYYCQNAY
SYPLTFGAGTKLELK
(SEQ ID NO: 100)

DIVMTQSPSSLTVTAGEKVTMSCKSSQSLLNSGNQKNYLTWYQQKPGQP
PKLLIYWASTRESGVPDRFTGSGSGTDFTLTISSVQAEDLTVYYCQNAY
SFPLTFGAGTKLELK
(SEQ ID NO: 101)

DIVMTQSPSSLTVTAGEKVTMSCKSSQSLLNSGNQRNYLTWYQRKPGQP
PKLLIYWASTRESGVPDRFTGSGSGTDFTLTISSVQAEDLTFYYCQNGY
SYPLTFGAGTKLELK
(SEQ ID NO: 102)

DIVMTQSPSSLTVTAGEKVTMSCKSSQSLLNSGNQKNYLTWYQQKPGQP
PKLLLYWASTRESGVPDRFTGSGSGTDFTLTISSVQAEDLTVYYCQNAY
SYPLTFGAGTKLELK
(SEQ ID NO: 103)

DIVMTQSPSSLTVTAGEKVTMSCKSSQSLLNSGNQKNYLTWYQQKPGQP
PKLLIYWASTRESGVPDRFTGSGSGTDFTLTISSVQAEDLAVYYCQNDY
IYPLTFGAGTKLGLK
(SEQ ID NO: 104)

DIVMTQSPSSLTVTAGEKVTMNCKSSQSLLNSGNQKNYLTWYQQKPGQP
PKLLIYWASTRESGVPDRFTGSGSGTDFTLTISSVQAEDLTVYYCQNGY
SYPLTFGAGTKLELK
(SEQ ID NO: 105)

DIVMTQSPSSLTVTAGEKVTMSCKSSQSLFNTGNQKNYLTWYQQKPGQP
PKLLIYWASTRESGVPDRFTGSGSGTDFTLTISSVQAEDLTVYYCQNGY
SYPLTFGAGTKLELK
(SEQ ID NO: 106)

DIVMTQSPSSLTVTPGEKVTMSCKSSQSLFNSGNQRNYLAWYQQKPGQP
PKLLIYWASTRESGVPDRFTGSGSGTDFTLTISSVQAEDLAVYYCQNDY
FYPLTFGAGTKLELK
(SEQ ID NO: 107)

DIVMTQSPSSLTVTAGEKVTMSCKSSQSLLNSGNQKNYLTWYQQKPGQP
PKLLIYWASTRESGVPDRFTGSGSGTDFTLTISSVQAEDLTVYYCQNGY
SYPLTFGAGTKLELK
(SEQ ID NO: 108)

DIVMTQSPSSLTVTAGEKVTMSCKSSQSLLNSGNQKNYLTWYQQKPGQP
PKLLIYWASTRDSGVPDRFTGSGSGTDFTLTISSVQAEDLAVYYCQNNY
YYPLTFGAGTNLELK
(SEQ ID NO: 109)

TABLE 2-continued

DIVMTQSPSSLTVTAGEKVTLSCKSSQSLLNSGNQKNYLTWYQQKPRQP
PKLLIYWASTRESGVPDRFTGSGSGTDFTLTISNVQAEDLTVYYCQNAY
SYPLTFGAGTKLELK
(SEQ ID NO: 110)

DIVMTQSPSSLTVTAGEKVTMSCKSSQSLLNSGNQKNYLTWYQQKPGQP
PKLLIYWASTRESGVPDRFTGSGSGTDFTLTISSVQAEDLAVYYCQNNY
IYPFTEGSGTKLEIK
(SEQ ID NO: 111)

DIVMTQSPSSLTVTAGEKVTMSCKSSQSLLNSGNQKNYLTWYQQKPGQP
PKLLIYWASTRESGVPDRFTGSGSGTDFTLTISSVQAEDLAVYYCQNDY
IYPLTFGAGTKLGLK
(SEQ ID NO: 112)

DIVMTQSPSSLTVTAGEKVTMTCKSSQILLNSGNQKNYLTWYQQKPGQP
PKLLIYWASTRESGVPDRFTGSGSGTDFSLTISSVQAEDLAIYYCQNDY
YYPFTEGSGTKLEIK
(SEQ ID NO: 113)

DIVMTQSPSSLTVTAGERVTVGCKSRQSLFNSENQKNYLSWYQQKPGQP
PKLLLYWISTRESGVPERFTGSGSGTDFTLTISSVQAEDLAVYYCQNNY
IYPFTEGSGTKLEIK
(SEQ ID NO: 114)

DIVMTQSPSSLTVTAGERVTMSCKSSQSLLNSGNLKNYLTWYQQKPGQP
PKLLIYWASTRESGVPDRFTGSGSGTDFTLTISTVQAEDLAVYYCQNDY
FYPLTFGAGTKLELK
(SEQ ID NO: 115)

EVQLQQSGPELVKPGASVKMSCKASGYTFISYLIHWVKQKPGQGLEWIG
YINPYNDGTKYNEKFKGKATLTSDKSSSTASMEFSSLTSEDSAVYYCTR
GDFWGQGTTLTVSS
(SEQ ID NO: 135)

EVQLQQSGPELVKPGASVKMSCKASGYTFTNYVMHWVKQKPGQGLEWIG
YINPPDDGTKYNEKFKGKATLISDKSSSTAYMELSSLTSEDSAVYYCTR
GDYWGQGTTLTVSS
(SEQ ID NO: 136)

DIVMTQSPSSLTVTAGEKVTMSCKSSQSLLNSGNQKNYLTWYQQKPGQP
PKLLIYWASIRASGVPDRFTGSGSGTDFTLTISSVQAEDLALYYCLNDY
SFPLTFGAGTKLELK
(SEQ ID NO: 137)

DIVMTQSPSSLTVTAGEKVTMTCKSSQSLLNSGNQKNYLTWYQQKPGQP
PKLLIYWASTRDSGVPDRFRGSGSGTDFTLTISSVQAEDLAVYYCLNDY
SFPLTFGAGTKLELK
(SEQ ID NO: 138)

In some embodiments, the anti-CLDN18.2 antibody (or antigen binding fragment thereof) comprises one, two, or three CDRs of a heavy chain variable domain (VH) comprising an amino acid sequence that is at least about 95%, 96%, 97%, 98%, 99%, or 100% identical to an amino acid sequence set forth in any one of SEQ ID NOs: 72-93 and 135-136 or one, two, or three CDRs of a light chain variable domain (VL) comprising an amino acid sequence that is at least about 95%, 96%, 97%, 98%, 99%, or 100% identical to an amino acid sequence set forth in any one of SEQ ID NOs: 94-115 and 137-138. In some embodiments, the anti-CLDN18.2 antibody (or antigen binding fragment thereof) comprises one, two, three, four five, or six CDRs of a heavy chain variable domain (VH) comprising an amino acid sequence that is at least about 95%, 96%, 97%, 98%, 99%, or 100% identical to an amino acid sequence set forth in any one of SEQ ID NOs: 72-93 and 135-136 and a light chain variable domain (VL) comprising an amino acid sequence that is at least about 95%, 96%, 97%, 98%, 99%, or 100% identical to an amino acid sequence set forth in any one of SEQ ID NOs: 94-115 and 137-138. In some embodiments, the anti-CLDN18.2 antibody (or antigen binding fragment thereof) comprises six CDRs of a heavy chain variable domain (VH) comprising an amino acid sequence that is at least about 95%, 96%, 97%, 98%, 99%, or 100% identical to an amino acid sequence set forth in any one of SEQ ID NOs: 72-93 and a light chain variable domain (VL) comprising an amino acid sequence that is at least about 95%, 96%, 97%, 98%, 99%, or 100% identical to an amino acid sequence set forth in any one of SEQ ID NOs: 94-115.

In certain embodiments, the anti-CLDN18.2 antibody (or antigen binding fragment thereof) comprises: (a) a CDR-H1 comprising GFTFSDYGMF (SEQ ID NO: 1) or a variant thereof comprising up to about 5 (such as about any of 1, 2, 3, 4, or 5) amino acid substitutions, (b) a CDR-H2 comprising YISSGSSNIYYADTVKG (SEQ ID NO: 12) or a variant thereof comprising up to about 5 (such as about any of 1, 2, 3, 4, or 5) amino acid substitutions, (c) a CDR-H3 comprising IARGNAMDY (SEQ ID NO: 31) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYFYPLT (SEQ ID NO: 59) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising IARGNAMDY (SEQ ID NO: 31) and/or a CDR-L3 comprising QNDYFYPLT (SEQ ID NO: 59). In certain embodiments, the anti-CLDN18.2 antibody (or antigen binding fragment thereof) comprises: (a) a CDR-H1 comprising GFTFSDYGMF (SEQ ID NO: 1), (b) a CDR-H2 comprising YISSGSSNIYYADTVKG (SEQ ID NO: 12), (c) a CDR-H3 comprising IARGNAMDY (SEQ ID NO: 31); (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYFYPLT (SEQ ID NO: 59). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 72 and/or a VL domain comprising an amino acid sequence that is at least about 95%, 96%, 97%, 98%, 99% or 100% identical to SEQ ID NO: 94. In some embodiments, the anti-CLDN18.2 antibody (or antigen binding fragment thereof) comprises 3 CDRs of a VH domain comprising SEQ ID NO: 72 and/or 3 CDRs of a VL domain comprising SEQ ID NO: 94. In some embodiments, the anti-CLDN18.2 antibody (or antigen binding fragment thereof) comprises a VH domain comprising SEQ ID NO: 72 and a VL domain comprising SEQ ID NO: 94.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YINSGSSTYYADTVKG (SEQ ID NO: 13) or a variant thereof comprising up to about 5 (such as about any of 1, 2, 3, 4, or 5) amino acid substitutions, (c) a CDR-H3 comprising FARGNVLDY (SEQ ID NO: 32) or a variant thereof comprising up to about 5 (such as about any of 1, 2, 3, 4, or 5) amino acid substitutions, (d) a CDR-L1 comprising RSSQSLLNSGNQRNYLT (SEQ ID NO: 45) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprisingQNGYSYPLT (SEQ ID NO: 60). In certain embodiments or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FARGNVLDY (SEQ ID NO: 32) and/or a CDR-L3 comprisingQNGYSYPLT (SEQ ID NO: 60). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YINSGSSTYYADTVKG (SEQ ID NO: 13), (c) a CDR-H3 comprising FARGNVLDY (SEQ ID NO: 32); (d) a CDR-L1 comprising RSSQSLLNSGNQRNYLT (SEQ ID NO: 45), (e) a CDR-L2 comprising WASTRES (SEQ ID NO: 55), and (f) a CDR-L3 comprisingQNGYSYPLT (SEQ ID NO: 60). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 73 and/or a VL domain comprising an amino acid sequence that is at least about 95%, 96%, 97%, 98%, 99% or 100% identical to SEQ ID NO: 95. In some embodiments, the anti-CLDN18.2 antibody (or antigen binding fragment thereof) comprises 3 CDRs of a VH domain comprising SEQ ID NO: 73 and/or 3 CDRs of a VL domain comprising SEQ ID NO: 95. In some embodiments, the anti-CLDN18.2 antibody (or antigen binding fragment thereof) comprises a VH domain comprising SEQ ID NO: 73 and a VL domain comprising SEQ ID NO: 95.

In certain embodiments, the anti-CLDN18.2 antibody (or antigen binding fragment thereof) comprises: (a) a CDR-H1 comprising GYSFTGYNIH (SEQ ID NO: 3) or a variant thereof comprising up to about 5 (such as about any of 1, 2, 3, 4, or 5) amino acid substitutions, (b) a CDR-H2 comprising YIDPNNGVTYSNQKFKG (SEQ ID NO: 14) or a variant thereof comprising up to about 5 (such as about any of 1, 2, 3, 4, or 5) amino acid substitutions, (c) a CDR-H3 comprising PYYGNSFDY (SEQ ID NO: 33) or a variant thereof comprising up to about 5 (such as about any of 1, 2, 3, 4, or 5) amino acid substitutions, (d) a CDR-L1 comprising KSSQSLLNSGNLRNYLT (SEQ ID NO: 46) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QDGYFYPFP (SEQ ID NO: 61) or a variant thereof comprising up to about 5 (such as about any of 1, 2, 3, 4, or 5) amino acid substitutions. In certain embodiments, the anti-CLDN18.2 antibody (or antigen binding fragment thereof) comprises: a CDR-H3 comprising PYYGNSFDY (SEQ ID NO: 33); and/or a CDR-L3 comprising QDGYFYPFP (SEQ ID NO: 61). In certain embodiments, the anti-CLDN18.2 antibody (or antigen binding fragment thereof) comprises: (a) a CDR-H1 comprising GYSFTGYNIH (SEQ ID NO: 3), (b) a CDR-H2 comprising YIDPNNGVTYSNQKFKG (SEQ ID NO: 14), a CDR-H3 comprising PYYGNSFDY (SEQ ID NO: 33), (d) a CDR-L1 comprising KSSQSLLNSGNLRNYLT (SEQ ID NO: 46), (e) a CDR-L2 comprising WASTRES (SEQ ID NO: 55), and (f) a CDR-L3 comprising QDGYFYPFP (SEQ ID NO: 61). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 74 and/or a VL domain comprising an amino acid sequence that is at least about 95%, 96%, 97%, 98%, 99% or 100% identical to SEQ ID NO: 96. In some embodiments, the anti-CLDN18.2 antibody (or antigen binding fragment thereof) comprises 3 CDRs of a VH domain comprising SEQ ID NO: 74 and/or 3 CDRs of a VL domain comprising SEQ ID NO: 96. In some embodiments, the anti-CLDN18.2 antibody (or antigen binding fragment thereof) comprises a VH domain comprising SEQ ID NO: 74 and aVL domain comprising SEQ ID NO: 96.

In certain embodiments, the anti-CLDN18.2 antibody (or antigen binding fragment thereof) comprises: (a) a CDR-H1 comprising GYTFTVWSMS (SEQ ID NO: 4) or a variant thereof comprising up to about 5 (such as about any of 1, 2, 3, 4, or 5) amino acid substitutions, (b) a CDR-H2 comprising EIYPKSGNTHYNEKFKG (SEQ ID NO: 15) or a variant thereof comprising up to about 5 (such as about any of 1, 2, 3, 4, or 5) amino acid substitutions, (c) a CDR-H3 comprising AYYGNSFAY (SEQ ID NO: 34) or a variant thereof comprising up to about 5 (such as about any of 1, 2, 3, 4, or 5) amino acid substitutions, (d) a CDR-L1 comprising KSSQSLLNSGNQRNYLT (SEQ ID NO: 47) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDFIYPFT (SEQ ID NO: 62) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising AYYGNSFAY (SEQ ID NO: 34); and/or a CDR-L3 comprising QND-FIYPFT (SEQ ID NO: 62). In certain embodiments, the anti-CLDN18.2 antibody (or antigen binding fragment thereof) comprises: (a) a CDR-H1 comprising GYTFTVWSMS (SEQ ID NO: 4), (b) a CDR-H2 comprising EIYPKSGNTHYNEKFKG (SEQ ID NO: 15), (c) a CDR-H3 comprising AYYGNSFAY (SEQ ID NO: 34), (d) a CDR-L1 comprising KSSQSLLNSGNQRNYLT (SEQ ID NO: 47), (e) a CDR-L2 comprising WASTRES (SEQ ID NO: 55), and (f) a CDR-L3 comprising QNDFIYPFT (SEQ ID NO: 62). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 75 and/or a VL domain comprising an amino acid sequence that is at least about 95%, 96%, 97%, 98%, 99% or 100% identical to SEQ ID NO: 97. In some embodiments, the anti-CLDN18.2 antibody (or antigen binding fragment thereof) comprises 3 CDRs of a VH domain comprising SEQ ID NO: 75 and/or 3 CDRs of a VL domain comprising SEQ ID NO: 97. In some embodiments, the anti-CLDN18.2 antibody (or antigen binding fragment thereof) comprises a VH domain comprising SEQ ID NO: 75 and a VL domain comprising SEQ ID NO: 97.

In certain embodiments, the anti-CLDN18.2 antibody (or antigen binding fragment thereof) comprises: (a) a CDR-H1 comprising GFTFSNNAMS (SEQ ID NO: 5) or a variant thereof comprising up to about 5 (such as about any of 1, 2, 3, 4, or 5) amino acid substitutions, (b) a CDR-H2 comprising TIIIGGTYTYYPDSVKG (SEQ ID NO: 16) or a variant thereof comprising up to about 5 (such as about any of 1, 2, 3, 4, or 5) amino acid substitutions, (c) a CDR-H3 comprising QVYGNSFAY (SEQ ID NO: 35) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNNYFYPFT (SEQ ID NO: 63) or a variant thereof comprising up to about 5 (such as about any of 1, 2, 3, 4, or 5) amino acid substitutions. In certain embodiments, the anti-CLDN18.2 antibody (or antigen binding fragment thereof) comprises: a CDR-H3 comprising QVYGNSFAY (SEQ ID NO: 35); and/or a CDR-L3 comprising QNNYFYPFT (SEQ ID NO: 63). In certain embodiments, the anti-CLDN18.2 antibody (or antigen binding fragment thereof) comprises: (a) a CDR-H1 comprising GFTFSN-NAMS (SEQ ID NO: 5), (b) a CDR-H2 comprising TIIIGGTYTYYPDSVKG (SEQ ID NO: 16), (c) a CDR-H3 comprising QVYGNSFAY (SEQ ID NO: 35), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNNYFYPFT (SEQ ID NO: 63). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 76 and/or a VL domain comprising an amino acid sequence that is at least about 95%, 96%, 97%, 98%, 99% or 100% identical to SEQ ID NO: 98. In some embodiments, the anti-CLDN18.2 antibody (or antigen binding fragment thereof) comprises 3 CDRs of a VH domain comprising SEQ ID NO: 76 and/or 3 CDRs of a VL domain comprising SEQ ID NO: 98. In some embodiments, the anti-CLDN18.2 antibody (or antigen binding fragment thereof) comprises a VH domain comprising SEQ ID NO: 76 and a VL domain comprising SEQ ID NO: 98.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YISSGSSTIYYADTMKG (SEQ ID NO: 18) or a variant thereof comprising up to about 5 (such as about any of 1, 2, 3, 4, or 5) amino acid substitutions, (c) a CDR-H3 comprising FVRGNSMDY (SEQ ID NO: 36) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNAYSYPLT (SEQ ID NO: 65) or a variant thereof comprising up to about 5 (such as about any of 1, 2, 3, 4, or 5) amino acid substitutions. In certain embodiments, the anti-CLDN18.2 antibody (or antigen binding fragment thereof) comprises (c) a CDR-H3 comprising FVRGNSMDY (SEQ ID NO: 36); and/or a CDR-L3 comprising QNAYSYPLT (SEQ ID NO: 65). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSSTIYYADTMKG (SEQ ID NO: 18), (c) a CDR-H3 comprising FVRGNSMDY (SEQ ID NO: 36), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 78 and/or a VL domain comprising an amino acid sequence that is at least about 95%, 96%, 97%, 98%, 99% or 100% identical to SEQ ID NO: 100. In some embodiments, the anti-CLDN18.2 antibody (or antigen binding fragment thereof) comprises 3 CDRs of a VH domain comprising SEQ ID NO: 78 and/or 3 CDRs of a VL domain comprising SEQ ID NO: 100. In some embodiments, the anti-CLDN18.2 antibody (or antigen binding fragment thereof) comprises a VH domain comprising SEQ ID NO: 78 and a VL domain comprising SEQ ID NO: 100.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising HISSGSNIIHYADTLKG (SEQ ID NO: 19) or a variant thereof comprising up to about 5 (such as about any of 1, 2, 3, 4, or 5) amino acid substitutions, (c) a CDR-H3 comprising FARGNTMDY (SEQ ID NO: 37) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNAYSFPLT (SEQ ID NO: 66) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FARGNTMDY (SEQ ID NO: 37); and/or a CDR-L3 comprising QNAYSFPLT (SEQ ID NO: 66). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising HISSGSNIIHYADTLKG (SEQ ID NO: 19), (c) a CDR-H3 comprising FARGNTMDY (SEQ ID NO: 37), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSFPLT (SEQ ID NO: 66). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 79 and/or a VL domain comprising an amino acid sequence that is at least about 95%, 96%, 97%, 98%, 99% or 100% identical to SEQ ID NO: 101. In some embodiments, the anti-CLDN18.2 antibody (or antigen binding fragment thereof) comprises 3 CDRs of a VH domain comprising SEQ ID NO: 79 and/or 3 CDRs of a VL domain comprising SEQ ID NO: 101. In some embodiments, the anti-CLDN18.2 antibody (or antigen binding fragment thereof) comprises a VH domain comprising SEQ ID NO: 79 and a VL domain comprising SEQ ID NO: 101.

In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSSTIYYADTMKG (SEQ ID NO: 18), (c) a CDR-H3 comprising FARGNTMDY (SEQ ID NO: 37) or a variant thereof comprising up to about 5 (such as about any of 1, 2, 3, 4, or 5) amino acid substitutions, (d) a CDR-L1 comprising KSSQSLLNSGNQRNYLT (SEQ ID NO: 47) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNGYSYPLT (SEQ ID NO: 60) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FARGNTMDY (SEQ ID NO: 37); and/or a CDR-L3 comprising QNGYSYPLT (SEQ ID NO: 60). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSSTIYYADTMKG (SEQ ID NO: 18), (c) a CDR-H3 comprising FARGNTMDY (SEQ ID NO: 37), (d) a CDR-L1 comprising KSSQSLLNSGNQRNYLT (SEQ ID NO: 47), (e) a CDR-L2 comprising WASTRES (SEQ ID NO: 55), and (f) a CDR-L3 comprising QNGYSYPLT (SEQ ID NO: 60). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 80 and/or a VL domain comprising an amino acid sequence that is at least about 95%, 96%, 97%, 98%, 99% or 100% identical to SEQ ID NO: 102. In some embodiments, the anti-CLDN18.2 antibody (or antigen binding fragment thereof) comprises 3 CDRs of a VH domain comprising SEQ ID NO: 80 and/or 3 CDRs of a VL domain comprising SEQ ID NO: 101. In some embodiments, the anti-CLDN18.2 antibody (or antigen binding fragment thereof) comprises a VH domain comprising SEQ ID NO: 80 and a VL domain comprising SEQ ID NO: 102.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YISSGSNTFYYTDTVKG (SEQ ID NO: 20) or a variant thereof comprising up to about 5 (such as about any of 1, 2, 3, 4, or 5) amino acid substitutions, (c) a CDR-H3 comprising FTRGNALDY (SEQ ID NO: 38) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNAYSYPLT (SEQ ID NO: 65) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FTRGNALDY (SEQ ID NO: 38); and/or a CDR-L3 comprising QNAYSYPLT (SEQ ID NO: 65). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSNTFYYTDTVKG (SEQ ID NO: 20), (c) a CDR-H3 comprising FTRGNALDY (SEQ ID NO: 38), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65).

In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 81 and/or a VL domain comprising an amino acid sequence that is at least about 95%, 96%, 97%, 98%, 99% or 100% identical to SEQ ID NO: 103. In some embodiments, the anti-CLDN18.2 antibody (or antigen binding fragment thereof) comprises 3 CDRs of a VH domain comprising SEQ ID NO: 81 and/or 3 CDRs of a VL domain comprising SEQ ID NO: 103. In some embodiments, the anti-CLDN18.2 antibody (or antigen binding fragment thereof) comprises a VH domain comprising SEQ ID NO: 81 and a VL domain comprising SEQ ID NO: 103.

In certain embodiments, the anti-CLDN18.2 antibody (or antigen binding fragment thereof) comprises: a) a CDR-H1 comprising GFTFSDYGMY (SEQ ID NO: 6) or a variant thereof comprising up to about 5 (such as about any of 1, 2, 3, 4, or 5) amino acid substitutions, (b) a CDR-H2 comprising YISSGSNTIYYADTVKG (SEQ ID NO: 21) or a variant thereof comprising up to about 5 (such as about any of 1, 2, 3, 4, or 5) amino acid substitutions, a CDR-H3 comprising IARGNAMDY (SEQ ID NO: 31) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYIYPLT (SEQ ID NO: 67) or a variant thereof comprising up to about 5 (such as about any of 1, 2, 3, 4, or 5) amino acid substitutions. In certain embodiments, the anti-CLDN18.2 antibody (or antigen binding fragment thereof) comprises: a CDR-H3 comprising IARGNAMDY (SEQ ID NO: 31); and/or a CDR-L3 comprising QNDYIYPLT (SEQ ID NO: 67). In certain embodiments, the anti-CLDN18.2 antibody (or antigen binding fragment thereof) comprises: a) a CDR-H1 comprising GFTFSDYGMY (SEQ ID NO: 6), (b) a CDR-H2 comprising YISSGSNTIYYADTVKG (SEQ ID NO: 21), (c) a CDR-H3 comprising IARGNAMDY (SEQ ID NO: 31), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYIYPLT (SEQ ID NO: 67). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 82 and/or a VL domain comprising an amino acid sequence that is at least about 95%, 96%, 97%, 98%, 99% or 100% identical to SEQ ID NO: 104. In some embodiments, the anti-CLDN18.2 antibody (or antigen binding fragment thereof) comprises 3 CDRs of a VH domain comprising SEQ ID NO: 82 and/or 3 CDRs of a VL domain comprising SEQ ID NO: 104. In some embodiments, the anti-CLDN18.2 antibody (or antigen binding fragment thereof) comprises a VH domain comprising SEQ ID NO: 82 and a VL domain comprising SEQ ID NO: 104.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising HISSGSSTIYYADTMKG (SEQ ID NO: 22) or a variant thereof comprising up to about 5 (such as about any of 1, 2, 3, 4, or 5) amino acid substitutions, (c) a CDR-H3 comprising FVRGNALDY (SEQ ID NO: 39) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNGYSYPLT (SEQ ID NO: 60) or a variant thereof comprising up to about 5 (such as about any of 1, 2, 3, 4, or 5) amino acid substitutions. In certain embodiments, the anti-CLDN18.2 antibody (or antigen binding fragment thereof) comprises (c) a CDR-H3 comprising FVRGNALDY (SEQ ID NO: 39); and/or a CDR-L3 comprising QNGYSYPLT (SEQ ID NO: 60). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising HISSGSSTIYYADTMKG (SEQ ID NO: 22), (c) a CDR-H3 comprising FVRGNALDY (SEQ ID NO: 39), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNGYSYPLT (SEQ ID NO: 60). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 83 and/or a VL domain comprising an amino acid sequence that is at least about 95%, 96%, 97%, 98%, 99% or 100% identical to SEQ ID NO: 105. In some embodiments, the anti-CLDN18.2 antibody (or antigen binding fragment thereof) comprises 3 CDRs of a VH domain comprising SEQ ID NO: 83 and/or 3 CDRs of a VL domain comprising SEQ ID NO: 105. In some embodiments, the anti-CLDN18.2 antibody (or antigen binding fragment thereof) comprises a VH domain comprising SEQ ID NO: 83 and a VL domain comprising SEQ ID NO: 105.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YISSGSSTIHYVDTMKG (SEQ ID NO: 23) or a variant thereof comprising up to about 5 (such as about any of 1, 2, 3, 4, or 5) amino acid substitutions, (c) a CDR-H3 comprising FARGNTLDY (SEQ ID NO: 40) or a variant thereof comprising up to about 5 (such as about any of 1, 2, 3, 4, or 5) amino acid substitutions, (d) a CDR-L1 comprising KSSQSLFNTGNQKNYLT (SEQ ID NO: 49) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising NGYSYPLT (SEQ ID NO: 60) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FARGNTLDY (SEQ ID NO: 40); and/or a CDR-L3 comprising NGYSYPLT (SEQ ID NO: 60). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSSTIHYVDTMKG (SEQ ID NO: 23), (c) a CDR-H3 comprising FARGNTLDY (SEQ ID NO: 40), (d) a CDR-L1 comprising KSSQSLFNTGNQKNYLT (SEQ ID NO: 49), (e) a CDR-L2 comprising WASTRES (SEQ ID NO: 55), and (f) a CDR-L3 comprising NGYSYPLT (SEQ ID NO: 60). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 84 and/or a VL domain comprising an amino acid sequence that is at least about 95%, 96%, 97%, 98%, 99% or 100% identical to SEQ ID NO: 106. In some embodiments, the anti-CLDN18.2 antibody (or antigen binding fragment thereof) comprises 3 CDRs of a VH domain comprising SEQ ID NO: 84 and/or 3 CDRs of a VL domain comprising SEQ ID NO: 106. In some embodiments, the anti-CLDN18.2 antibody (or antigen binding fragment thereof) comprises a VH domain comprising SEQ ID NO: 84 and a VL domain comprising SEQ ID NO: 106.

In certain embodiments, the anti-CLDN18.2 antibody (or antigen binding fragment thereof) comprises: (a) a CDR-H1 comprising GFTFSDYGMY (SEQ ID NO: 6) or a variant thereof comprising up to about 5 (such as about any of 1, 2, 3, 4, or 5) amino acid substitutions, (b) a CDR-H2 comprising YISSGSSTIYYADTVKG (SEQ ID NO: 24) or a variant thereof comprising up to about 5 (such as about any of 1, 2, 3, 4, or 5) amino acid substitutions, (c) a CDR-H3 comprising IARGNAMDY (SEQ ID NO: 31) or a variant thereof comprising up to about 5 (such as about any of 1, 2, 3, 4, or 5) amino acid substitutions, (d) a CDR-L1 comprising KSSQSLFNSGNQRNYLA (SEQ ID NO: 50) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYFYPLT (SEQ ID NO: 59) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising IARGNAMDY (SEQ ID NO: 31); and/or a CDR-L3 comprising QNDYFYPLT (SEQ ID NO: 59). In certain embodiments, the anti-CLDN18.2 antibody (or antigen binding fragment thereof) comprises: (a) a CDR-H1 comprising GFTFSDYGMY (SEQ ID NO: 6), (b) a CDR-H2 comprising YISSGSSTIYYADTVKG (SEQ ID NO: 24), (c) a CDR-H3 comprising IARGNAMDY (SEQ ID NO: 31), (d) a CDR-L1 comprising KSSQSLFNSGNQRNYLA (SEQ ID NO: 50), (e) a CDR-L2 comprising WASTRES (SEQ ID NO: 55), and (f) a CDR-L3 comprising QNDYFYPLT (SEQ ID NO: 59). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 85 and/or a VL domain comprising an amino acid sequence that is at least about 95%, 96%, 97%, 98%, 99% or 100% identical to SEQ ID NO: 107. In some embodiments, the anti-CLDN18.2 antibody (or antigen binding fragment thereof) comprises 3 CDRs of a VH domain comprising SEQ ID NO: 85 and/or 3 CDRs of a VL domain comprising SEQ ID NO: 107. In some embodiments, the anti-CLDN18.2 antibody (or antigen binding fragment thereof) comprises a VH domain comprising SEQ ID NO: 85 and a VL domain comprising SEQ ID NO: 107.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YISSGSSPIYYADTVKG (SEQ ID NO: 25) or a variant thereof comprising up to about 5 (such as about any of 1, 2, 3, 4, or 5) amino acid substitutions, (c) a CDR-H3 comprising FARGNAMDY (SEQ ID NO: 41) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRDS (SEQ ID NO: 56) or a variant thereof comprising up to about 5 (such as about any of 1, 2, 3, 4, or 5) amino acid substitutions, and (f) a CDR-L3 comprising QNNYYYPLT (SEQ ID NO: 68) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FARGNAMDY (SEQ ID NO: 41); and/or a CDR-L3 comprising QNNYYYPLT (SEQ ID NO: 68). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSSPIYYADTVKG (SEQ ID NO: 25), (c) a CDR-H3 comprising FARGNAMDY (SEQ ID NO: 41), (d) a CDR-L1 comprising KSSQSLLNSGNQKNYLT (SEQ ID NO: 44), (e) a CDR-L2 comprising WASTRDS (SEQ ID NO: 56), and (f) a CDR-L3 comprising QNNYYYPLT (SEQ ID NO: 68). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 87 and/or a VL domain comprising an amino acid sequence that is at least about 95%, 96%, 97%, 98%, 99% or 100% identical to SEQ ID NO: 109. In some embodiments, the anti-CLDN18.2 antibody (or antigen binding fragment thereof) comprises 3 CDRs of a VH domain comprising SEQ ID NO: 87 and/or 3 CDRs of a VL domain comprising SEQ ID NO: 109. In some embodiments, the anti-CLDN18.2 antibody (or antigen binding fragment thereof) comprises a VH domain comprising SEQ ID NO: 87 and a VL domain comprising SEQ ID NO: 109.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YISSGSSTIYYADTMKG (SEQ ID NO: 18) or a variant thereof comprising up to about 5 (such as about any of 1, 2, 3, 4, or 5) amino acid substitutions, (c) a CDR-H3 comprising FVRGNSMDY (SEQ ID NO: 36) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNAYSYPLT (SEQ ID NO: 65) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FVRGNSMDY (SEQ ID NO: 36); and/or a CDR-L3 comprising QNAYSYPLT (SEQ ID NO: 65). In certain embodiments, the anti- CLDN18.2 antibody (or antigen binding fragment thereof) comprises: (a) a CDR-H1 comprising GFTFSDYGMH (SEQ ID NO: 2), (b) a CDR-H2 comprising YISSGSSTIYY-ADTMKG (SEQ ID NO: 18), (c) a CDR-H3 comprising FVRGNSMDY (SEQ ID NO: 36), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 88 and/or a VL domain comprising an amino acid sequence that is at least about 95%, 96%, 97%, 98%, 99% or 100% identical to SEQ ID NO: 110. In some embodiments, the anti-CLDN18.2 antibody (or antigen binding fragment thereof) comprises 3 CDRs of a VH domain comprising SEQ ID NO: 88 and/or 3 CDRs of a VL domain comprising SEQ ID NO: 110. In some embodiments, the anti-CLDN18.2 antibody (or antigen binding fragment thereof) comprises a VH domain comprising SEQ ID NO: 88 and a VL domain comprising SEQ ID NO: 110.

In certain embodiments, the anti-CLDN18.2 antibody (or antigen binding fragment thereof) comprises: (a) a CDR-H1 comprising GFTFSNYAMS (SEQ ID NO: 8) or a variant thereof comprising up to about 5 (such as about any of 1, 2, 3, 4, or 5) amino acid substitutions, (b) a CDR-H2 comprising TIIIGGTYTYYPDSVKG (SEQ ID NO: 16) or a variant thereof comprising up to about 5 (such as about any of 1, 2, 3, 4, or 5) amino acid substitutions, (c) a CDR-H3 comprising QVYGNSFAY (SEQ ID NO: 35) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNNYIYPFT (SEQ ID NO: 69) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising QVYGNSFAY (SEQ ID NO: 35); and/or a CDR-L3 comprising QNNYIYPFT (SEQ ID NO: 69). In certain embodiments, the anti-CLDN18.2 antibody (or antigen binding fragment thereof) comprises: (a) a CDR-H1 comprising GFTFSNYAMS (SEQ ID NO: 8), (b) a CDR-H2 comprising TIIIGGTYTYYPDSVKG (SEQ ID NO: 16), (c) a CDR-H3 comprising QVYGNSFAY (SEQ ID NO: 35), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNNYIYPFT (SEQ ID NO: 69). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 89 and/or a VL domain comprising an amino acid sequence that is at least about 95%, 96%, 97%, 98%, 99% or 100% identical to SEQ ID NO: 111. In some embodiments, the anti-CLDN18.2 antibody (or antigen binding fragment thereof) comprises 3 CDRs of a VH domain comprising SEQ ID NO: 89 and/or 3 CDRs of a VL domain comprising SEQ ID NO: 111. In some embodiments, the anti-CLDN18.2 antibody (or antigen binding fragment thereof) comprises a VH domain comprising SEQ ID NO: 89 and aVL domain comprising SEQ ID NO: 111.

In certain embodiments, the anti-CLDN18.2 antibody (or antigen binding fragment thereof) comprises: (a) a CDR-H1 comprising GFTFSDYGMY (SEQ ID NO: 6) or a variant thereof comprising up to about 5 (such as about any of 1, 2, 3, 4, or 5) amino acid substitutions, (b) a CDR-H2 comprising YISSGSNNIYYADTVKG (SEQ ID NO: 26) or a variant thereof comprising up to about 5 (such as about any of 1, 2, 3, 4, or 5) amino acid substitutions, (c) a CDR-H3 comprising IARGNAMDY (SEQ ID NO: 31) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYIYPLT (SEQ ID NO: 67) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising IARGNAMDY (SEQ ID NO: 31); and/or a CDR-L3 comprising QNDYIY-PLT (SEQ ID NO: 67). In certain embodiments, the anti-CLDN18.2 antibody (or antigen binding fragment thereof) comprises: (a) a CDR-H1 comprising GFTFSDYGMY (SEQ ID NO: 6), (b) a CDR-H2 comprising YISSGSN-NIYYADTVKG (SEQ ID NO: 26), (c) a CDR-H3 comprising IARGNAMDY (SEQ ID NO: 31), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYIYPLT (SEQ ID NO: 67). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 90 and/or a VL domain comprising an amino acid sequence that is at least about 95%, 96%, 97%, 98%, 99% or 100% identical to SEQ ID NO: 112. In some embodiments, the anti-CLDN18.2 antibody (or antigen binding fragment thereof) comprises 3 CDRs of a VH domain comprising SEQ ID NO: 90 and/or 3 CDRs of a VL domain comprising SEQ ID NO: 112. In some embodiments, the anti-CLDN18.2 antibody (or antigen binding fragment thereof) comprises a VH domain comprising SEQ ID NO: 90 and a VL domain comprising SEQ ID NO: 112.

In certain embodiments, the anti-CLDN18.2 antibody (or antigen binding fragment thereof) comprises: (a) a CDR-H1 comprising GYTFTSWSIS (SEQ ID NO: 9) or a variant thereof comprising up to about 5 (such as about any of 1, 2, 3, 4, or 5) amino acid substitutions, (b) a CDR-H2 comprising EIYPRSDNIHYNEKFKG (SEQ ID NO: 27) or a variant thereof comprising up to about 5 (such as about any of 1, 2, 3, 4, or 5) amino acid substitutions, (c) a CDR-H3 comprising AYYGNSFAY (SEQ ID NO: 34) or a variant thereof comprising up to about 5 (such as about any of 1, 2, 3, 4, or 5) amino acid substitutions, (d) a CDR-L1 comprising KSSQILLNSGNQKNYLT (SEQ ID NO: 51) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYYYPFT (SEQ ID NO: 70) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising AYYGNSFAY (SEQ ID NO: 34); and/or a CDR-L3 comprising QNDYYYPFT (SEQ ID NO: 70). In certain embodiments, the anti-CLDN18.2 antibody (or antigen binding fragment thereof) comprises: (a) a CDR-H1 comprising GYTFTSW-SIS (SEQ ID NO: 9), (b) a CDR-H2 comprising EIYPRSD-NIHYNEKFKG (SEQ ID NO: 27), (c) a CDR-H3 comprising AYYGNSFAY (SEQ ID NO: 34), (d) a CDR-L1 comprising KSSQILLNSGNQKNYLT (SEQ ID NO: 51), (e) a CDR-L2 comprising WASTRES (SEQ ID NO: 55), and (f) a CDR-L3 comprising QNDYYYPFT (SEQ ID NO: 70). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 91 and/or a VL domain comprising an amino acid sequence that is at least about 95%, 96%, 97%, 98%, 99% or 100% identical to SEQ ID NO: 113. In some embodiments, the anti-CLDN18.2 antibody (or antigen binding fragment thereof) comprises 3 CDRs of a VH domain comprising SEQ ID NO: 91 and/or 3 CDRs of a VL domain comprising SEQ ID NO: 113. In some embodiments, the anti-CLDN18.2 antibody (or antigen binding fragment thereof) comprises a VH domain comprising SEQ ID NO: 91 and a VL domain comprising SEQ ID NO: 113.

In certain embodiments, the anti-CLDN18.2 antibody (or antigen binding fragment thereof) comprises: (a) a CDR-H1 comprising GYSFTGYNMN (SEQ ID NO: 10) or a variant thereof comprising up to about 5 (such as about any of 1, 2, 3, 4, or 5) amino acid substitutions, (b) a CDR-H2 comprising NINPYYSNTNYNQRFKG (SEQ ID NO: 28) or a variant thereof comprising up to about 5 (such as about any of 1, 2, 3, 4, or 5) amino acid substitutions, (c) a CDR-H3 comprising CDRGNSFDY (SEQ ID NO: 42) or a variant thereof comprising up to about 5 (such as about any of 1, 2, 3, 4, or 5) amino acid substitutions, (d) a CDR-L1 comprising KSRQSLFNSENQKNYLS (SEQ ID NO: 52) or a variant thereof comprising up to about 5 (such as about any of 1, 2, 3, 4, or 5) amino acid substitutions, (e) a CDR-L2 comprising WTSTRES (SEQ ID NO: 57) or a variant thereof comprising up to about 5 (such as about any of 1, 2, 3, 4, or 5) amino acid substitutions, and (f) a CDR-L3 comprising QNNYIYPFT (SEQ ID NO: 69) or a variant thereof comprising up to about 5 (such as about any of 1, 2, 3, 4, or 5) amino acid substitutions. In certain embodiments, the anti-CLDN18.2 antibody (or antigen binding fragment thereof) comprises: a CDR-H3 comprising CDRGNSFDY (SEQ ID NO: 42); and/or a CDR-L3 comprising QNNYIYPFT (SEQ ID NO: 69). In certain embodiments, the anti-CLDN18.2 antibody (or antigen binding fragment thereof) comprises: (a) a CDR-H1 comprising GYSFTGY-NMN (SEQ ID NO: 10), (b) a CDR-H2 comprising NINPYYSNTNYNQRFKG (SEQ ID NO: 28), (c) a CDR-H3 comprising CDRGNSFDY (SEQ ID NO: 42), (d) a CDR-L1 comprising KSRQSLFNSENQKNYLS (SEQ ID NO: 52), (e) a CDR-L2 comprising WTSTRES (SEQ ID NO: 57), and (f) a CDR-L3 comprising QNNYIYPFT (SEQ ID NO: 69). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 92 and/or a VL domain comprising an amino acid sequence that is at least about 95%, 96%, 97%, 98%, 99% or 100% identical to SEQ ID NO: 114. In some embodiments, the anti-CLDN18.2 antibody (or antigen binding fragment thereof) comprises 3 CDRs of a VH domain comprising SEQ ID NO: 92 and/or 3 CDRs of a VL domain comprising SEQ ID NO: 114. In some embodiments, the anti-CLDN18.2 antibody (or antigen binding fragment thereof) comprises a VH domain comprising SEQ ID NO: 92 and a VL domain comprising SEQ ID NO: 114.

In certain embodiments, the anti-CLDN18.2 antibody (or antigen binding fragment thereof) comprises: (a) a CDR-H1 comprising GFTFSDYGMH (SEQ ID NO: 2) or a variant thereof comprising up to about 5 (such as about any of 1, 2, 3, 4, or 5) amino acid substitutions, (b) a CDR-H2 comprising YISSGSSSIYYADTVKG (SEQ ID NO: 17) or a variant thereof comprising up to about 5 (such as about any of 1, 2, 3, 4, or 5) amino acid substitutions, (c) a CDR-H3 comprising IARGNAMDY (SEQ ID NO: 31) or a variant thereof comprising up to about 5 (such as about any of 1, 2, 3, 4, or 5) amino acid substitutions, (d) a CDR-L1 comprising KSSQSLLNSGNQRNYLA (SEQ ID NO: 48) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYSYPLT (SEQ ID NO: 64) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising IARGNAMDY (SEQ ID NO: 31); and/or a VL domain comprising a CDR-L3 comprising QNDYSYPLT (SEQ ID NO: 64). In certain embodiments, the anti-CLDN18.2 antibody (or antigen binding fragment thereof) comprises: (a) a CDR-H1 comprising GFTFSDYGMH (SEQ ID NO: 2), (b) a CDR-H2 comprising YISSGSSSIYYADTVKG (SEQ ID NO: 17), (c) a CDR-H3 comprising IARGNAMDY (SEQ ID NO: 31), (d) a CDR-L1 comprising KSSQSLLNSGNQRNYLA (SEQ ID NO: 48), (e) a CDR-L2 comprising WASTRES (SEQ ID NO: 55), and (f) a CDR-L3 comprising QNDYSY-PLT (SEQ ID NO: 64). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 77 and/or a VL domain comprising an amino acid sequence that is at least about 95%, 96%, 97%, 98%, 99% or 100% identical to SEQ ID NO: 99. In some embodiments, the anti-CLDN18.2 antibody (or antigen binding fragment thereof) comprises 3 CDRs of a VH domain comprising SEQ ID NO: 77 and/or 3 CDRs of a VL domain comprising SEQ ID NO: 99. In some embodiments, the anti-CLDN18.2 antibody (or antigen binding fragment thereof) comprises a VH domain comprising SEQ ID NO: 77 and a VL domain comprising SEQ ID NO: 99.

In certain embodiments, the anti-CLDN18.2 antibody (or antigen binding fragment thereof) comprises: (a) a CDR-H1 comprising GFSFSDYGMH (SEQ ID NO: 7) or a variant thereof comprising up to about 5 (such as about any of 1, 2, 3, 4, or 5) amino acid substitutions, (b) a CDR-H2 comprising HISSGSSTIYYADTMKG (SEQ ID NO: 22) or a variant thereof comprising up to about 5 (such as about any of 1, 2, 3, 4, or 5) amino acid substitutions, (c) a CDR-H3 comprising FARGNTMDY (SEQ ID NO: 37) or a variant thereof comprising up to about 5 (such as about any of 1, 2, 3, 4, or 5) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNGYSYPLT (SEQ ID NO: 60) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising FARGNTMDY (SEQ ID NO: 37); and/or a CDR-L3 comprising QNGYSYPLT (SEQ ID NO: 60). In certain embodiments, the anti-CLDN18.2 antibody (or antigen binding fragment thereof) comprises: (a) a CDR-H1 comprising GFSFSDYGMH (SEQ ID NO: 7), (b) a CDR-H2 comprising HISSGSSTIYYADTMKG (SEQ ID NO: 22), (c) a CDR-H3 comprising FARGNTMDY (SEQ ID NO: 37), (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNGYSYPLT (SEQ ID NO: 60). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 86 and/or a VL domain comprising an amino acid sequence that is at least about 95%, 96%, 97%, 98%, 99% or 100% identical to SEQ ID NO: 108. In some embodiments, the anti-CLDN18.2 antibody (or antigen binding fragment thereof) comprises 3 CDRs of a VH domain comprising SEQ ID NO: 86 and/or 3 CDRs of a VL domain comprising SEQ ID NO: 108. In some embodiments, the anti-CLDN18.2 antibody (or antigen binding fragment thereof) comprises a VH domain comprising SEQ ID NO: 86 and aVL domain comprising SEQ ID NO: 108.

In certain embodiments, the anti-CLDN18.2 antibody (or antigen binding fragment thereof) comprises: (a) a CDR-H1 comprising GFTFSDYGMY (SEQ ID NO: 6) or a variant thereof comprising up to about 5 (such as about any of 1, 2, 3, 4, or 5) amino acid substitutions, (b) a CDR-H2 comprising FISSGSSTIYCADTVKG (SEQ ID NO: 29) or a variant thereof comprising up to about 5 (such as about any of 1, 2, 3, 4, or 5) amino acid substitutions, (c) a CDR-H3 comprising IARGNAMDY (SEQ ID NO: 31) or a variant thereof comprising up to about 5 (such as about any of 1, 2, 3, 4, or 5) amino acid substitutions, (d) a CDR-L1 comprising KSSQSLLNSGNLKNYLT (SEQ ID NO: 53) or a variant thereof comprising up to about 5 (such as about any of 1, 2, 3, 4, or 5) amino acid substitutions, (e) a CDR-L2 comprising WASTRES (SEQ ID NO: 55) or a variant thereof comprising up to about 5 (such as about any of 1, 2, 3, 4, or 5) amino acid substitutions, and (f) a CDR-L3 comprising QNDYFYPLT (SEQ ID NO: 59) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising IARGNAMDY (SEQ ID NO: 31); and/or a CDR-L3 comprising QNDYFYPLT (SEQ ID NO: 59). In certain embodiments, the anti-CLDN18.2 antibody (or antigen binding fragment thereof) comprises: (a) a CDR-H1 comprising GFTFSDYGMY (SEQ ID NO: 6), (b) a CDR-H2 comprising FISSGSSTIYCADTVKG (SEQ ID NO: 29), (c) a CDR-H3 comprising IARGNAMDY (SEQ ID NO: 31), (d) a CDR-L1 comprising KSSQSLLNSGNLKNYLT (SEQ ID NO: 53), (e) a CDR-L2 comprising WASTRES (SEQ ID NO: 55), and (f) a CDR-L3 comprising QNDYFYPLT (SEQ ID NO: 59). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 93 and/or a VL domain comprising an amino acid sequence that is at least about 95%, 96%, 97%, 98%, 99% or 100% identical to SEQ ID NO: 115. In some embodiments, the anti-CLDN18.2 antibody (or antigen binding fragment thereof) comprises 3 CDRs of a VH domain comprising SEQ ID NO: 93 and/or 3 CDRs of a VL domain comprising SEQ ID NO: 115. In some embodiments, the anti-CLDN18.2 antibody (or antigen binding fragment thereof) comprises a VH domain comprising SEQ ID NO: 93 and a VL domain comprising SEQ ID NO: 115.

In certain embodiments, the anti-CLDN18.2 antibody (or antigen binding fragment thereof) comprises: (a) a CDR-H1 comprising GYTFISYLIH(SEQ ID NO: 128) or a variant thereof comprising up to about 5 (such as about any of 1, 2, 3, 4, or 5) amino acid substitutions, (b) a CDR-H2 comprising amino acid sequence set forth in SEQ ID NO: YINPYNDGTKYNEKFKG (SEQ ID NO: 129) or a variant thereof comprising up to about 5 (such as about any of 1, 2, 3, 4, or 5) amino acid substitutions, (c) a CDR-H3 comprising (such as consisting of) GDF or a variant thereof comprising up to about 3 (such as about any of 1, 2, or 3) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASIRAS (SEQ ID NO: 130) or a variant thereof comprising up to about 5 (such as about any of 1, 2, 3, 4, or 5) amino acid substitutions, and (f) a CDR-L3 comprising LNDYSFPLT (SEQ ID NO: 131) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising (such as consisting of) GDF; and/or a CDR-L3 comprising LNDYSFPLT (SEQ ID NO: 131). In certain embodiments, the anti-CLDN18.2 antibody (or antigen binding fragment thereof) comprises: (a) a CDR-H1 comprising GYTFISYLIH (SEQ ID NO: 128), (b) a CDR-H2 comprising YINPYNDGTKYNEKFKG (SEQ ID NO: 129), (c) a CDR-H3 comprising (such as consisting of) GDF, (d) a CDR-L1 comprising KSSQSLLNSGNQKNYLT (SEQ ID NO: 44), (e) a CDR-L2 comprising WASIRAS (SEQ ID NO: 130), and (f) a CDR-L3 comprising LNDYSFPLT (SEQ ID NO: 131). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 135 and/or a VL domain comprising an amino acid sequence that is at least about 95%, 96%, 97%, 98%, 99% or 100% identical to SEQ ID NO: 137. In some embodiments, the anti-CLDN18.2 antibody (or antigen binding fragment thereof) comprises 3 CDRs of a VH domain comprising SEQ ID NO: 135 and/or 3 CDRs of a VL domain comprising SEQ ID NO: 135. In some embodiments, the anti-CLDN18.2 antibody (or antigen binding fragment thereof) comprises a VH domain comprising SEQ ID NO: 135 and a VL domain comprising SEQ ID NO: 137. In certain embodiments, the anti-CLDN18.2 antibody specifically binds CLDN18.1.

In certain embodiments, the anti-CLDN18.2 antibody (or antigen binding fragment thereof) comprises: (a) a CDR-H1 comprising GYTFTNYVMH (SEQ ID NO: 132) or a variant thereof comprising up to about 5 (such as about any of 1, 2, 3, 4, or 5) amino acid substitutions, (b) a CDR-H2 comprising YINPFDDGTKYNEKFKG (SEQ ID NO: 133) or a variant thereof comprising up to about 5 (such as about any of 1, 2, 3, 4, or 5) amino acid substitutions, (c) a CDR-H3 comprising (such as consisting of) GDY or a variant thereof comprising up to about 3 (such as about any of 1, 2, or 3) amino acid substitutions, (d) a CDR-L1 comprising KSSQSLLNSGNQKNYLT (SEQ ID NO: 44) or a variant thereof comprising up to about 5 (such as about any of 1, 2, 3, 4, or 5) amino acid substitutions, (e) a CDR-L2 comprising WASTRDS (SEQ ID NO: 134) or a variant thereof comprising up to about 5 (such as about any of 1, 2, 3, 4, or 5) amino acid substitutions, and (f) a CDR-L3 comprising LNDYSFPLT (SEQ ID NO: 131) or a variant thereof comprising up to about 5 (such as about any of 1, 2, 3, 4, or 5) amino acid substitutions. In certain embodiments, the anti-CLDN18.2 antibody (or antigen binding fragment thereof) comprises a CDR-H3 comprising (such as consisting of) GDY; and/or a CDR-L3 comprising LNDYSFPLT (SEQ ID NO: 131). In certain embodiments, the anti-CLDN18.2 antibody (or antigen binding fragment thereof) comprises: (a) a CDR-H1 comprising GYTFTNYVMH (SEQ ID NO: 132), (b) a CDR-H2 comprising YINPFDDGTKYNEKFKG (SEQ ID NO: 133), (c) a CDR-H3 comprising (such as consisting of) GDY, (d) a CDR-L1 comprising KSSQSLLNSGNQKNYLT (SEQ ID NO: 44), (e) a CDR-L2 comprising WASTRDS (SEQ ID NO: 134), and (f) a CDR-L3 comprising LNDYSFPLT (SEQ ID NO: 131). In some embodiments, the anti-CLDN18.2 antibody (or antigen binding fragment thereof) comprises a VH domain comprising an amino acid sequence that is at least about 95%, 96%, 97%, 98%, 99% or 100% identical to SEQ ID NO: 136 and/or a VL domain comprising an amino acid sequence that is at least about 95%, 96%, 97%, 98%, 99% or 100% identical to SEQ ID NO: 138. In some embodiments, the anti-CLDN18.2 antibody (or antigen binding fragment thereof) comprises 3 CDRs of a VH domain comprising SEQ ID NO: 136 and/or 3 CDRs of a VL domain comprising SEQ ID NO: 138. In some embodiments, the anti-CLDN18.2 antibody (or antigen binding fragment thereof) comprises a VH domain comprising SEQ ID NO: 136 and a VL domain comprising SEQ ID NO: 138. In certain embodiments, the anti-CLDN18.2 antibody specifically binds CLDN18.1.

In some embodiments, provided are amino acid sequence variants of the anti-CLDN18.2 antibodies described herein ("anti-CLDN18.2 antibody variants"). For example, it may be desirable to improve the binding affinity and/or other biological properties of an anti-CLDN18.2 antibody. Amino acid sequence variants of an anti-CLDN18.2 antibody may be prepared by introducing appropriate modifications into the nucleotide sequence encoding the antibody agent, or by peptide synthesis. Such modifications include, for example, deletions from, and/or insertions into and/or substitutions of residues within the amino acid sequences of the antibody agent. Any combination of deletion, insertion, and substitution can be made to arrive at the final construct, provided that the final construct possesses the desired characteristics, e.g., antigen-binding.

In some embodiments, an anti-CLDN18.2 antibody variants having one or more amino acid substitutions are provided. Sites of interest for substitutional mutagenesis include the HVRs and FRs. Amino acid substitutions may be introduced into an antibody agent of interest and the products screened for a desired activity, e.g., retained/improved antigen binding, decreased immunogenicity, or improved ADCC or CDC.

An exemplary substitutional variant is an affinity matured antibody agent, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody agent variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody agent to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of an antibody agent that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody agent with antigen is affected. Further substitutions may be introduced at the amino acid locations demonstrating functional sensitivity to the initial substitutions. Alternatively, or additionally, a crystal structure of an antigen-antibody agent complex can be determined to identify contact points between the antibody agent and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody agent with an N-terminal methionyl residue. Other insertional variants of the antibody agent molecule include the fusion to the N- or C-terminus of the antibody agent to an enzyme (e.g. for ADEPT) or a polypeptide which increases the serum half-life of the antibody agent.

In certain embodiments, the amino acid substitution(s) in an anti-CLDN antibody variant are conservative amino acid substitution(s). In certain embodiments, the amino acid substitution(s) in an anti-CLDN antibody variant are non-conservative amino acid substitution(s). In certain embodiments, the amino acid substitutions do not substantially reduce the ability of the antibody to bind antigen. For example, conservative alterations (e.g., conservative substitutions as provided herein) that do not substantially reduce CLDN18.2 binding affinity may be made. The binding affinity of anti-CLDN18.2 antibodies to CLDN18.2 may be assessed using methods described in the Examples below.

Conservative substitutions are shown in Table 3 under the heading of "conservative substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved CLDN18.2 binding.

TABLE 3

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions entail exchanging a member of one of these classes for another class. An exemplary substitutional variant is an affinity matured antibody, which may be conveniently generated, e.g., using phage display based affinity maturation techniques such as those described herein. Briefly, one or more CDR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments, the anti-CLDN18.2 antibody cross-reacts with at least one allelic variant of the CLDN18.2 protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring CLDN18.2 (or fragments thereof). In some embodiments, the anti-CLDN18.2 antibody does not cross-react with any allelic variant of the CLDN18.2 protein (or fragments thereof).

In some embodiments, the anti-CLDN18.2 antibody (or antibody variant) binds to (e.g., cross-reacts with) CLDN18.2 proteins from at least two different species. In some embodiments, for example, the anti-CLDN18.2 antibody (or antibody variant) binds to a human CLDN18.2 protein (or fragments thereof) and a CLDN18.2 protein (or fragments thereof) from a mouse, rat, or non-human primate (such as a cynomolgous or rhesus monkey). In some embodiments, the anti-CLDN18.2 antibody may be completely specific for human CLDN18.2 and may not exhibit species or other types of non-human cross-reactivity.

In some embodiments, the anti-CLDN18.2 antibody agent specifically recognizes CLDN18.2 expressed on the cell surface of a cancer cell (such as solid tumor). In some embodiments, the anti-CLDN18.2 antibody agent specifically recognizes CLDN18.2 expressed on the surface tumor cells or on cancerous tissue (e.g., gastric cancer cells, esophageal cancer cells, gastroesophageal junction cancer cells, bile duct cancer cells, pancreatic cancer cells, ovarian cancer cells, hepatic cancer cells, head and neck cancer cells, gallbladder cancer cells, colon cancer cells, and lung cancer cells). In some embodiments, the anti-CLDN18.2 antibody agent specifically recognizes CLDN18.2 expressed on the cell surface of one or more of cancer cell lines, including, but not limited to, e.g., KATO III (ATCC HTB-103) and NUGC-4 (JCRB0834).

In certain embodiments, the anti-CLDN18.2 antibody binds CLDN18.2 but not CLDN 18.1. In certain embodiments, the anti-CLDN18.2 antibody binds to both CLDN18.2 and CLDN18.1. In certain embodiments, the antibody has a stronger binding affinity for CLDN18.2 than it has for CLDN18.1. In some embodiments, the antibody has comparable affinities for CLDN18.2 and CLDN18.1, e.g., wherein the EC50 and/or $K_d$ values of the antibody binding to CLDN18.2 and the antibody binding to CLDN18.1 are within less than any one of about 10-fold, 9-fold, 8-fold, 7-fold, 6-fold, 5-fold, 4-fold, 3-fold, 2-fold, or 1.5-fold, as measured by a method well known in the art (such as described elsewhere herein). In some embodiments, the anti-CLDN18.2 antibody (any format) specifically binds to CLDN18.2 with a $K_d$ of about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M).

In some embodiments, the $K_d$ of the binding between the CLDN18.2 antibody and a non-target protein is greater than the $K_d$ of the binding between the anti-CLDN18.2 antibody and CLDN18.2. In some embodiments, the non-target protein is not CLDN18.2. In some embodiments, the non-target protein is CLDN18.1. In some embodiments, the non-target protein is not CLDN18.1. In some embodiments, the $K_d$ of the binding of the anti-CLDN18.2 antibody to a non-target protein can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times greater than the $K_d$ of the binding between the anti-CLDN18.2 antibody and a target CLDN18.2.

In some embodiments, the CLDN18.2 antibody provided herein that binds specifically to CLDN18.2 binds to an epitope on CLDN18.2 (e.g., human CLDN18.2) that is distinct from the epitope of CLDN18.2 bound by IMAB362. In some embodiments, the CLDN18.2 antibody provided herein that binds specifically to CLDN18.2 binds to an epitope on CLDN18.2 (e.g., human CLDN18.2) that does not overlap with the epitope of CLDN18.2 bound by IMAB362. IMAB362 (also known as zolbetuximab or claudiximab) is a chimeric monoclonal antibody that binds CLDN18.2.

The CLDN18.2 antibody that binds specifically to CLDN18.2 can be of any of the various types of antibodies as defined above, but preferably is a human, humanized, chimeric antibody. Non-human anti-CLDN18.2 antibodies are also contemplated. In some embodiments, non-human anti-CLDN18.2 antibodies comprise human CDR sequences from an anti-CLDN18.2 antibody as described herein and non-human framework sequences. Non-human framework sequences include, in some embodiments, any sequence that can be used for generating synthetic heavy and/or light chain variable regions using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-CLDN18.2 antibody includes an anti-CLDN18.2 antibody generated by grafting one or more human CDR sequences as described herein onto a non-human framework sequence (e.g., a mouse or chicken framework sequence).

In certain embodiments, the antibody comprises an Fc sequence of a human IgG, e.g., human IgG1, human IgG2, human IgG3 or human IgG4. In certain embodiments, the Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function, including, but not limited to those described elsewhere herein. For example, WO 00/42072 and Shields et al. J Biol. Chem. 9(2): 6591-6604 (2001) describes antibody variants with improved or diminished binding to FcRs. The contents of those publications are specifically incorporated herein by reference. The antibody can be in the form of a Fab, Fab', a F(ab)'2, single-chain Fv (scFv), an Fv fragment; a diabody and a linear antibody. Also, the antibody can be a multispecific antibody that binds to CLDN18.2, but also binds one or more other targets and inhibits their function. The antibody can be conjugated to a therapeutic agent (e.g., cytotoxic agent, a radioisotope and a chemotherapeutic agent) or a label for detecting CLDN18.2 in patient samples or in vivo by imaging (e.g., radioisotope, fluorescent dye and enzyme). Other modifications include the conjugation of toxins to anti-CLDN18.2 antibodies provided herein.

Nucleic Acids Encoding Anti-Claudin 18.2 Antibodies

Nucleic acid molecules encoding the anti-CLDN18.2 antibodies described herein are also contemplated. In some embodiments, there is provided a nucleic acid (or a set of nucleic acids) encoding an anti-CLDN18.2 antibody, including any of the anti-CLDN18.2 antibodies described herein. In some embodiments, the nucleic acid (or a set of nucleic acids) encoding the anti-CLDN18.2 antibody described herein may further comprises a nucleic acid sequence encoding a peptide tag (such as protein purification tag, e.g., His-tag, HA tag).

Also contemplated here are isolated host cells comprising an anti-CLDN18.2 antibody, an isolated nucleic acid encoding the polypeptide components of the anti-CLDN18.2 antibody, and a vector comprising nucleic acid(s) encoding the polypeptide components of the anti-CLDN18.2 antibody described herein.

The present application also includes variants to these nucleic acid sequences. For example, the variants include nucleotide sequences that hybridize to the nucleic acid sequences encoding an anti-CLDN18.2 antibody described herein under at least moderately stringent hybridization conditions.

The present invention also provides vectors in which a nucleic acid of the present invention is inserted.

In brief summary, the expression of an anti-CLDN18.2 antibody by a natural or synthetic nucleic acid encoding the anti-CLDN18.2 antibody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-CLDN18.2 antibody agent is inducible. In some embodiments, a nucleic acid sequence encoding the anti-CLDN18.2 antibody agent is operably linked to an inducible promoter, including any inducible promoter described herein.

Methods of Antibody Production

An antibody of the present disclosure may be produced by any means known in the art. Exemplary techniques for antibody production are described below; however these exemplary techniques are provided for illustrative purposes only and are not intended to be limiting. In addition, exemplary antibody properties contemplated for use with the antibodies described herein are further described.

To prepare an antigen, the antigen may be purified or otherwise obtained from a natural source, or it may be expressed using recombinant techniques. In some embodiments, the antigen may be used as a soluble protein. In some embodiments, the antigen may be conjugate to another polypeptide or other moiety, e.g., to increase its immunogenicity. For example, an antigen described herein may be coupled with an Fc region. In some embodiments, a cell expressing the antigen on its cell surface may be used as the antigen.

Polyclonal antibodies can be raised in an animal by multiple subcutaneous (sc) or intraperitoneal (ip) injections of the antigen and an adjuvant. For example, descriptions of chicken immunization are described herein. In some embodiments, the antigen is conjugated with an immunogenic protein, e.g., keyhole limpet hemocyanin, serum albumin, bovine thyroglobulin, or soybean trypsin inhibitor using a bifunctional or derivatizing agent. Exemplary methods for immunization of chickens are provided herein. Relevant methods suitable for a variety of other organisms, such as mammals, are well known in the art.

As described supra, monoclonal antibodies may be produced by a variety of methods. In some embodiments, a monoclonal antibody of the present disclosure is made using the hybridoma method first described by Kohler et al., *Nature,* 256:495 (1975), and further described in Hongo et al., *Hybridoma,* 14 (3): 253-260 (1995); Harlow et al., *Antibodies: A Laboratory Manual,* (Cold Spring Harbor Laboratory Press, 2nd ed. 1988); and Hammerling et al., in: *Monoclonal Antibodies and T-Cell Hybridomas* 563-681 (Elsevier, N.Y., 1981). Human hybridoma technology (Trioma technology) is described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005). A culture medium in which hybridoma cells are grown may be screened for the presence of an antibody of interest, e.g., by in vitro binding assay, immunoprecipitation, ELISA, RIA, etc.; and the binding affinity may be determined, e.g., by Scatchard analysis. A hybridoma that produces an antibody with desired binding properties can be subcloned and grown using known culture techniques, grown in vivo as ascites tumors in an animal, and the like.

In some embodiments, a monoclonal antibody is made using a library method, such as a phage display library. See, e.g., Hoogenboom et al. in *Methods in Molecular Biology* 178:1-37 (O'Brien et al., ed., Human Press, Totowa, N.J., 2001). In some embodiments, repertoires of VH and VL genes are cloned by polymerase chain reaction (PCR) and recombined randomly in phage libraries, which are then screened for antigen-binding phage, e.g., as described in Winter et al., *Ann. Rev. Immunol.,* 12: 433-455 (1994). Phage typically display antibody fragments, either as single-chain Fv (scFv) fragments or as Fab fragments. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992).

In some embodiments, an antibody of the present disclosure is a chicken antibody. Chicken antibodies can be produced using various techniques known in the art; see, e.g., U.S. Pat. Nos. 6,143,559; 8,592,644; and 9,380,769.

In some embodiments, an antibody of the present disclosure is a chimeric antibody. See, e.g., U.S. Pat. No. 4,816,567 and Morrison et al., *Proc. Nat. Acad. Sci. USA,* 81:6851-6855 (1984). In some embodiments, a chimeric antibody comprises a non-human variable region (e.g., a variable region derived from a chicken, mouse, rat, hamster, rabbit, or non-human primate, such as a monkey) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. A non-human antibody can be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody (e.g., a chicken antibody), and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR or CDR residues are derived), e.g., to restore or improve antibody specificity or affinity. Humanized antibodies and methods of making them are reviewed, e.g., in Almagro and Fransson, *Front. Biosci.* 13:1619-1633 (2008). Methods of humanizing a chicken antibody have also been described, e.g., in WO2005014653.

Human framework regions useful for humanization include but are not limited to: framework regions selected using the "best-fit" method; framework regions derived from the consensus sequence of human antibodies of a particular subgroup of light or heavy chain variable regions; human somatically mutated framework regions or human germline framework regions; and framework regions derived from screening FR libraries. See, e.g., Sims et al. *J. Immunol.* 151:2296 (1993); Carter et al. *Proc. Natl. Acad. Sci. USA*, 89:4285 (1992); Presta et al. *J. Immunol.*, 151:2623 (1993); Almagro and Fransson, *Front. Biosci.* 13:1619-1633 (2008); and Baca et al., *J. Biol. Chem.* 272:10678-10684 (1997).

In some embodiments, an antibody of the present disclosure is a human antibody. Human antibodies can be produced using various techniques known in the art. In some embodiments, the human antibody is produced by a non-human animal, such as the genetically engineered chickens (see, e.g., U.S. Pat. Nos. 8,592,644; and 9,380,769) and/or mice described herein. Human antibodies are described generally in Lonberg, *Curr. Opin. Immunol.* 20:450-459 (2008).

In some embodiments, an antibody of the present disclosure is an antibody fragment, including without limitation a Fab, F(ab')2, Fab'-SH, Fv, or scFv fragment, or a single domain, single heavy chain, or single light chain antibody. Antibody fragments can be generated, e.g., by enzymatic digestion or by recombinant techniques. In some embodiments, Proteolytic digestion of an intact antibody is used to generate an antibody fragment, e.g., as described in Morimoto et al., *Journal of Biochemical and Biophysical Methods* 24:107-117 (1992) and Brennan et al., *Science*, 229:81 (1985). In some embodiments, an antibody fragment is produced by a recombinant host cell. For example, Fab, Fv and ScFv antibody fragments are expressed by and secreted from *E. coli*. Antibody fragments can alternatively be isolated from an antibody phage library.

Fab'-SH fragments can be directly recovered from *E. coli* and chemically coupled to form F(ab')$_2$ fragments. See Carter et al., *Bio/Technology* 10:163-167 (1992). F(ab')$_2$ fragments can also be isolated directly from a recombinant host cell culture. Fab and F(ab')$_2$ fragment with increased in vivo half-life comprising salvage receptor binding epitope residues are described in U.S. Pat. No. 5,869,046.

In some embodiments, an antibody is a single chain Fv fragment (scFv). See WO 93/16185 and U.S. Pat. Nos. 5,571,894 and 5,587,458. scFv fusion proteins can be constructed to produce a fusion of an effector protein at either the amino or the carboxy terminus of an scFv. The antibody fragment may also be a "linear antibody", e.g., as described in U.S. Pat. No. 5,641,870, for example. Such linear antibodies may be monospecific or bispecific.

In some embodiments, an antibody of the present disclosure is a multispecific antibody. Multispecific antibodies possess binding specificities against more than one antigen (e.g., having two, three, or more binding specificities). In some embodiments, the antibody is a bispecific antibody. In some embodiments, a bispecific antibody comprises two different binding specificities for the same antigen (e.g., having different binding affinity and/or specific epitope of the same antigen). In some embodiments, a bispecific antibody comprises binding specificities for two distinct antigens. In some embodiments, the bispecific antibody is a full-length or intact antibody. In some embodiments, the bispecific antibody is an antibody fragment of the present disclosure.

Various methods are known in the art for generating and purifying a bispecific antibody. Numerous approaches have been described. One approach is the "knobs-into-holes" or "protuberance-into-cavity" approach (see, e.g., U.S. Pat. No. 5,731,168). In some embodiments, heterodimerization of Fc domain monomers is promoted by introducing different, but compatible, substitutions in the two Fc domain monomers, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain monomer and involved in the dimerization of two Fc domain monomers. In some embodiments, a hole in one CH3 antibody constant domain is created to accommodate a knob in another CH3 antibody constant domain, such that the knob and hole amino acids act to promote or favor the heterodimerization of the two Fc domain monomers. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain monomer includes the knob mutation T366W and the other Fc domain monomer includes hole mutations T366S, L358A, and Y407V. Examples of knob-into-hole amino acid pairs include, but are not limited to, those shown in Table 4.

TABLE 4

| Knob-into-Hole Amino Acid Mutations | | | | | | | | |
|---|---|---|---|---|---|---|---|---|
| Fc domain monomer 1 | Y407T | Y407A | F405A | T394S | T366S L358A Y407V | T394W Y407T | T394S Y407A | T366W T394S |
| Fc domain monomer 2 | T366Y | T366W | T394W | F405W | T366W | T366Y F405A | T366W F405W | F405W Y407A |

Another approach uses antibody variable domains with the desired binding specificities (antibody-antigen combining sites) fused to immunoglobulin constant domain sequences, e.g., with an immunoglobulin heavy chain constant domain, comprising at least part of the hinge, CH2, and CH3 regions. In some embodiments, the bispecific antibody has a hybrid immunoglobulin heavy chain with a first binding specificity in one arm and a hybrid immunoglobulin heavy chain-light chain pair (providing a second binding specificity) in the other arm. See WO 94/04690. Another approach uses cross-linking (see, e.g., U.S. Pat. No. 4,676,980) to produce a heteroconjugate antibody. In some embodiments, bispecific antibodies can be prepared using chemical linkage (see, e.g., Brennan et al., *Science*, 229: 81 (1985)) to proteolytically cleave an intact antibody into F(ab')$_2$ fragments that are reduced in the presence of a dithiol complexing agent and converted to thionitrobenzoate (TNB) derivatives, one of which is reconverted to the Fab'-thiol by reduction and mixed with the other Fab'-TNB derivative to form the bispecific antibody. In some embodiments, Fab'-SH fragments are chemically coupled. In some embodiments, bispecific antibody fragments are produced in cell culture using leucine zippers, as in Kostelny et al., *J Immunol.*, 148(5):1547-1553 (1992). For other bispecific antibody formats, see, e.g., Spiess, C. et al. (2015) *Mol. Immunol.* 67:95-106.

In some embodiments, an antibody of the present disclosure is a diabody. See, e.g., Hollinger et al., *Proc. Nat. Acad. Sci. USA*, 90:6444-6448 (1993). In a diabody, the V$_H$ and V$_L$ domains of one fragment pair with complementary V$_L$ and V$_H$ domains of another fragment, thus forming two antigen-binding sites. Another strategy for making bispecific antibody fragments by the use of single-chain Fv (sFv) dimers has also been reported. See Gruber et al, *J. Immunol,* 152:5368 (1994).

In some embodiments, an antibody of the present disclosure is a single-domain antibody. A single-domain antibody refers to a single polypeptide chain comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1). In one embodiment, a single-domain antibody includes all or a portion of the heavy chain variable domain of an antibody. Camelid antibodies are also known.

Antibodies can be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An antibody of the present disclosure can be produced recombinantly as a fusion polypeptide with a heterologous polypeptide, e.g., a signal sequence or other polypeptide having a specific cleavage site at the N-terminus of the mature protein or polypeptide. The heterologous signal sequence selected can be one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, etc. In mammalian cell expression, mammalian signal sequences as well as viral secretory leaders, for example, the herpes simplex gD signal, are available.

Both expression and cloning vectors contain a nucleic acid sequence that enables the vector to replicate in one or more selected host cells, e.g., to allow the vector to replicate independently of the host chromosomal DNA. This sequence can include origins of replication or autonomously replicating sequences. Such sequences are well known for a variety of bacteria, yeast, and viruses. Generally, the origin of replication component is not needed for mammalian expression vectors (the SV40 origin may be used because it contains the early promoter).

Expression and cloning vectors can contain a selection gene or selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media. Examples of dominant selection use the drugs neomycin, mycophenolic acid and hygromycin. Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, and the like. For example, a Chinese hamster ovary (CHO) cell line deficient in endogenous DHFR activity transformed with the DHFR gene is identified by culturing the transformants in a culture medium containing methotrexate (Mtx), a competitive antagonist of DHFR.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

Expression and cloning vectors generally contain a promoter that is recognized by the host organism and is operably linked to nucleic acid encoding an antibody. Promoters suitable for use with prokaryotic hosts include the phoA promoter, 3-lactamase and lactose promoter systems, alkaline phosphatase promoter, a tryptophan (trp) promoter system, and hybrid promoters such as the tac promoter. However, other known bacterial promoters are suitable. Promoter sequences are known for eukaryotes. Yeast promoters are well known in the art and can include inducible promoters/enhancers regulated by growth conditions. Virtually all eukaryotic genes have an AT-rich region located approximately 25 to 30 bases upstream from the site where transcription is initiated. Examples include without limitation the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Antibody transcription from vectors in mammalian host cells can be controlled, for example, by promoters obtained from the genomes of viruses. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Alternatively, the Rous Sarcoma Virus long terminal repeat can be used as the promoter.

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus.

Expression vectors used in eukaryotic host cells (yeast, fungi, insect, plant, animal, human, or nucleated cells from other multicellular organisms) will also contain sequences necessary for the termination of transcription and for stabilizing the mRNA.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, etc. In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006).

Plant cell cultures of cotton, corn, potato, soybean, petunia, tomato, duckweed (Leninaceae), alfalfa (*M. truncatula*), and tobacco can also be utilized as hosts.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified.

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

The host cells of the present disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of skill in the art.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps.

Glycosylation Variants

In some embodiments, an anti-CLDN18.2 antibody provided herein is altered to increase or decrease the extent to which the anti-CLDN18.2 antibody is glycosylated. Addition or deletion of glycosylation sites to an anti-CLDN18.2 antibody may be conveniently accomplished by altering the amino acid sequence of the anti-CLDN18.2 antibody or polypeptide portion thereof such that one or more glycosylation sites is created or removed.

Where the a anti-CLDN18.2 antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-CLDN18.2 antibody of the invention may be made in order to create anti-CLDN18.2 antibody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody agent therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-CLDN18.2 antibody variants are provided comprising an Fc region wherein a carbohydrate structure attached to the Fc region has reduced fucose or lacks fucose, which may improve ADCC function. Specifically, anti-CLDN18.2 antibodies are contemplated herein that have reduced fucose relative to the amount of fucose on the same anti-CLDN18.2 antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-CLDN18.2 antibody is one wherein less than about 50%, 40%, 30%, 20%, 10%, or 5% of the N-linked glycans thereon comprise fucose. For example, the amount of fucose in such an anti-CLDN18.2 antibody may be from 1% to 80%, from 1% to 65%, from 5% to 65% or from 20% to 40%. In some embodiments, the anti-CLDN18.2 antibody is one wherein none of the N-linked glycans thereon comprise fucose, i.e., wherein the anti-CLDN18.2 antibody is completely without fucose, or has no fucose or is afucosylated. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about 3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody agent variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-CLDN18.2 antibody variants are further provided with bisected oligosaccharides, e.g., in which a biantennary oligosaccharide attached to the Fc region of the anti-CLDN18.2 antibody is bisected by GlcNAc. Such anti-CLDN18.2 antibody variants may have reduced fucosylation and/or improved ADCC function. Examples of such antibody agent variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93(5): 851-861 (2006). anti-CLDN18.2 antibody variants with at least one galactose residue in the oligosaccharide attached to the Fc region are also provided. Such anti-CLDN18.2 antibody variants may have improved CDC function. Such antibody agent variants are described, e.g., in WO 1997/30087 (Patel et al.); WO 1998/58964 (Raju, S.); and WO 1999/22764 (Raju, S.).

In some embodiments, the anti-CLDN18.2 antibody variants comprising an Fc region are capable of binding to an FcγRIII. In some embodiments, the anti-CLDN18.2 antibody variants comprising an Fc region have ADCC activity in the presence of human effector cells (e.g., T cell) or have increased ADCC activity in the presence of human effector cells compared to the otherwise same anti-CLDN18.2 antibody comprising a human wild-type IgG1Fc region.

Cysteine Engineered Variants

In some embodiments, it may be desirable to create cysteine engineered anti-CLDN18.2 antibodies in which one or more amino acid residues are substituted with cysteine residues. In some embodiments, the substituted residues occur at accessible sites of the anti-CLDN18.2 antibody. By substituting those residues with cysteine, reactive thiol groups are thereby positioned at accessible sites of the anti-CLDN18.2 antibody and may be used to conjugate the anti-CLDN18.2 antibody to other moieties, such as drug moieties or linker-drug moieties, to create an anti-CLDN18.2 immunoconjugate, as described further herein. Cysteine engineered anti-CLDN18.2 antibodies may be generated as described, e.g., in U.S. Pat. No. 7,521,541.

Effector Function Engineering

It may be desirable to modify an anti-CLDN18.2 antibody provided herein with respect to effector function, so as to enhance, e.g., the effectiveness of the antibody in treating cancer. For example, cysteine residue(s) can be introduced into the Fc region, thereby allowing inter-chain disulfide bond formation in this region. The homodimeric antibody thus generated can have improved internalization capability and/or increased complement-mediated cell killing and antibody-dependent cellular cytotoxicity (ADCC). See, Caron et al., *J. Exp. Med.*, 176: 1191-1195 (1992) and Shapes, *J. Immunol.*, 148: 2918-2922 (1992). Homodimeric antibodies with enhanced anti-tumor activity can also be prepared using heterobifunctional cross-linkers as described in Wolff et al., *Cancer Research*, 53: 2560-2565 (1993). Alternatively, an antibody can be engineered to comprise usual Fc regions and can thereby have enhanced complement lysis and ADCC capabilities. See, Stevenson et al., *Anti-Cancer Drug Design* 3: 219-230 (1989).

Mutations or alterations in the Fc region sequences can be made to improve FcR binding (e.g., binding to FcγR, FcRn). In some embodiments, an anti-CLDN18.2 antibody provided herein comprises at least one altered effector function, e.g., altered ADCC, CDC, and/or FcRn binding compared to a native IgG or a parent antibody. In some embodiments, the effector function of the antibody comprising the mutation or alteration is increased relative to the parent antibody. In some embodiments, the effector function of the antibody comprising the mutation or alteration is decreased relative to the parent antibody. Examples of several useful specific mutations are described in, e.g., Shields, R L et al. (2001) *JBC* 276(6)$_{6591}$-6604; Presta, L. G., (2002) *Biochemical Society Transactions* 30(4):487-490; and WO 00/42072.

In some embodiments, an anti-CLDN18.2 antibody provided herein comprises an Fc receptor mutation, e.g., a substitution mutation at least one position of the Fc region. Such substitution mutation(s) may be made to amino acid positions in the Fc domain that include, but are not limited to, e.g., 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439, wherein the numbering of the residues in the Fc region is according to the EU numbering system. In some embodiments, the Fc receptor mutation is a D265A substitution. In some embodiments, the Fc receptor mutation is a N297A substitution. Additional suitable mutations are well known in the art. Exemplary mutations are set forth in, e.g., U.S. Pat. No. 7,332,581.

Immunoconjugates and Covalent Modifications

The invention also pertains to immunoconjugates comprising an antibody conjugated to second moiety. In some embodiments, the second moiety is a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Exemplary chemotherapeutic agents useful in the generation of such immunoconjugates are described elsewhere herein.

In certain embodiments, an anti-CLDN18.2 antibody provided herein (or an antigen-binding fragment thereof) is conjugated to maytansine, a maytansinoid, or calicheamicin. In certain embodiments, an anti-CLDN18.2 antibody provided herein (or an antigen-binding fragment thereof) is conjugated to the maytansinoid DM1.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Also provided are heteroconjugate antibodies comprising an anti-CLDN18.2 antibody described herein covalently joined to at least one other antibody. Heteroconjugate antibodies have, for example, been proposed to target immune-system cells to unwanted cells (U.S. Pat. No. 4,676,980), and for treatment of HIV infection. Heteroconjugate antibodies comprising an anti-CLDN18.2 antibody described herein can be prepared in vitro using known methods in synthetic protein chemistry, including those involving cross-linking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Also provided is an anti-CLDN18.2 antibody comprising at least one covalent modification. One type of covalent modification includes reacting targeted amino acid residues of an anti-CLDN18.2 with an organic derivatizing agent that is capable of reacting with selected side chains or the N- or C-terminal residues of the antibody. Commonly used cross-linking agents include, but are not limited to, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N- maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification comprises linking ananti-CLDN18.2 antibody provided herein (or an antigen-binding fragment thereof) to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

Chimeric Molecules

An anti-CLDN18.2 antibody provided herein (or an antigen-binding fragment thereof) may also be modified form achimeric molecule comprising the antibody fused to another, heterologous polypeptide or amino acid sequence.

In one embodiment, such a chimeric molecule comprises a fusion of an anti-CLDN18.2 antibody provided herein (or an antigen-binding fragment thereof) with a protein transduction domain which targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of an anti-CLDN18.2 antibody provided herein (or an antigen-binding fragment thereof) with a tag polypeptide which provides an epitope to which an anti-tag antibody can selectively bind. The epitope tag is generally placed at the amino- or carboxyl-terminus of a polypeptide. The presence of such epitope-tagged forms of an anti-CLDN18.2 antibody provided herein (or an antigen-binding fragment thereof) can be detected using an antibody against the tag polypeptide. Various tag polypeptides and their respective antibodies are known in the art. Examples include poly-histidine (poly-His) or poly-histidine-glycine (poly-His-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA* 87:6393-6397 (1990)].

Chimeric Antigen Receptor (CAR) and CAR Effector Cells

The anti-CLDN18.2 antibody or fragment thereof (referred to as an "anti-CLDN18.2 moiety") in some embodiments is part of an anti-CLDN18.2 construct. The anti-CLDN18.2 construct in some embodiments is a chimeric antigen receptor (CAR) comprising an anti-CLDN18.2 antibody moiety (also referred to herein as an "anti-CLDN18.2 CAR"). Also provided is a CAR effector cell (e.g., T cell, NK cell or macrophage) comprising a CAR comprising an anti-CLDN18.2 antibody moiety. Such cell is also referred to herein as an "anti-CLDN18.2 CAR effector cell", e.g., an "anti-CLDN18.2 CAR T cell," an "anti-CLDN18.2 CAR NK cell," or an "anti-CLDN18.2 CAR macrophage".

The anti-CLDN18.2 CAR in some embodiments comprises a) an extracellular domain comprising an anti-CLDN18.2 antibody moiety that specifically binds to CLDN18.2, and b) an intracellular signaling domain. A transmembrane domain may be present between the extracellular domain and the intracellular domain.

Between the extracellular domain and the transmembrane domain of the anti-CLDN18.2 CAR, or between the intracellular domain and the transmembrane domain of the anti-CLDN18.2 CAR, there may be a spacer domain. The spacer domain can be any oligopeptide or polypeptide that functions to link the transmembrane domain to the extracellular domain or the intracellular domain in the polypeptide chain. A spacer domain may comprise up to about 300 amino acids, including for example about 10 to about 100, or about 25 to about 50 amino acids.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the α, β, δ, or γ chain of the T-cell receptors, CD28, CD3ε, CD3ζ, CD45, CD4, CD5, CD8, CD9, CD16, CD22, CD33, CD37, CD64, CD80, CD86, CD134, CD137, or CD154. In some embodiments, the transmembrane domain may be synthetic, in which case it may comprise predominantly hydrophobic residues such as leucine and valine. In some embodiments, a triplet of phenylalanine, tryptophan and valine may be found at each end of a synthetic transmembrane domain. In some embodiments, a short oligo-(?) or polypeptide linker, having a length of, for example, between about 2 and about 10 (such as about any of 2, 3, 4, 5, 6, 7, 8, 9, or 10) amino acids in length may form the linkage between the transmembrane domain and the intracellular signaling domain of the anti-CLDN18.2 CAR. In some embodiments, the linker is a glycine-serine doublet.

In some embodiments, the transmembrane domain that naturally is associated with one of the sequences in the intracellular domain of the anti-CLDN18.2 CAR is used (e.g., if an anti-CLDN18.2 CAR intracellular domain comprises a 4-1BB co-stimulatory sequence, the transmembrane domain of the anti-CLDN18.2 CAR is derived from the 4-1BB transmembrane domain).

The intracellular signaling domain of the anti-CLDN18.2 CAR is responsible for activation of at least one of the normal effector functions of the immune cell in which the anti-CLDN18.2 CAR has been placed in. Effector function of a T cell, NK cell, or macrophage for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term "intracellular signaling sequence" is thus meant to include any truncated portion of the intracellular signaling domain sufficient to transduce the effector function signal.

Examples of intracellular signaling domains for use in the anti-CLDN18.2 CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

T cell activation can be mediated by two distinct classes of intracellular signaling sequence: those that initiate antigen-dependent primary activation through the TCR (primary signaling sequences) and those that act in an antigen-independent manner to provide a secondary or co-stimulatory signal (co-stimulatory signaling sequences). The anti-CLDN18.2 CARs described herein can comprise one or both of the signaling sequences.

Primary signaling sequences regulate primary activation of the TCR complex either in a stimulatory way, or in an inhibitory way. Primary signaling sequences that act in a stimulatory manner may contain signaling motifs which are known as immunoreceptor tyrosine-based activation motifs or ITAMs. The anti-CLDN18.2 CAR constructs in some embodiments comprise one or more ITAMs. Examples of ITAM containing primary signaling sequences that are of particular use in the invention include those derived from TCRζ, FcRγ, FcRβ, CD3γ, CD3δ, CD3ε, CD5, CD22, CD79a, CD79b, and CD66d.

In some embodiments, the anti-CLDN18.2 CAR comprises a primary signaling sequence derived from CD3ζ. For example, the intracellular signaling domain of the CAR can comprise the CD3ζ intracellular signaling sequence by itself or combined with any other desired intracellular signaling sequence(s) useful in the context of the anti-CLDN18.2 CAR of the invention.

The costimulatory signaling sequence described herein can be a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the intracellular signaling domain of the anti-CLDN18.2 CAR comprises the intracellular signaling sequence of CD3ζ and the intracellular signaling sequence of CD28. In some embodiments, the intracellular signaling domain of the anti-CLDN18.2 CAR comprises the intracellular signaling sequence of CD3ζ and the intracellular signaling sequence of 4-1BB. In some embodiments, the intracellular signaling domain of the anti-CLDN18.2 CAR comprises the intracellular signaling sequence of CD3ζ and the intracellular signaling sequences of CD28 and 4-1BB or other costimulatory molecules.

Thus, for example, in some embodiments, there is provided an anti-CLDN18.2 CAR comprising a) an extracellular domain comprising an anti-CLDN18.2 antibody moiety that specifically binds to CLDN18.2 (such as any one of the anti-CLDN18.2 antibodies or fragments (e.g., scFv) thereof), b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 and/or 4-1BB intracellular signaling sequence. In some embodiments, the intracellular domain comprises a CD3ζ intracellular signaling sequence and a CD28 and/or −1BB intracellular signaling sequence. In some embodiments, the intracellular domain comprises a CD3ζ intracellular signaling sequence and a CD28 and/or −1BB intracellular signaling sequence and a separate cytokine transgene, like a CAR-inducible interleukin-12 (iIL-12) cassette.

Also provided herein are effector cells (such as, T cells, NK cells, and/or macrophages) expressing an anti-CLDN18.2 CAR.

Also provided are methods of producing an effector cell expressing an anti-CLDN18.2 CAR, the method comprising introducing a nucleic acid encoding the anti-CLDN18.2 CAR into the effector cell. In some embodiments, the method comprises introducing a vector comprising the nucleic acid encoding the anti-CLDN18.2 CAR into the effector cell, e.g., by transduction, transfection, or electroporation. In some embodiments, the method comprises introducing a vector comprising the nucleic acid sequence encoding the anti-CLDN18.2 CAR by viral transduction. In some embodiments, the method comprises introducing a vector comprising the nucleic acid encoding the anti-CLDN18.2 CAR by transposons. In some embodiments, the method comprises introducing a vector comprising the nucleic acid sequence encoding the anti-CLDN18.2 CAR by CRISPR/Cas9. In some embodiments, the method comprises introducing a vector comprising the nucleic acid sequence encoding the anti-CLDN18.2 CAR by non-viral transfer, e.g., electroporation of plasmid DNA or In Vitro Transcribed mRNA (IVT-mRNA). Transduction, transfection, or electroporation of the vectors or mRNAs into the effector cells can be carried out using any method known in the art.

Methods of Treatment

An anti-CLDN18.2 antibody described herein (or an antigen-binding fragment thereof) may be administered to subjects (e.g., mammals such as humans) to treat or delay progression of a disease or disorder involving abnormal CLDN18.2 activity or expression, including, for example, solid tumor or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.). In certain embodiments, provided is an anti-CLDN18.2 antibody described herein (or an antigen-binding fragment thereof) for use in the manufacture of a medicament for the treatment of solid tumor or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) in a subject (such as a mammal, e.g., a human). In certain embodiments, provided is an anti-CLDN18.2 antibody described herein (or an antigen-binding fragment thereof) for use in treating solid tumor or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) in a subject (such as a mammal, e.g., a human). In certain embodiments, provided is a pharmaceutical composition comprising an anti-CLDN18.2 antibody described herein (or an antigen-binding fragment thereof) for use in treating solid tumor or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) in a subject (such as a mammal, e.g., a human). In some embodiments, CDLN 18.2-expressing tumor are treated.

In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a CDLN 18.2-expressing tumor (such as solid tumor) or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.). In certain embodiments, the subject has been diagnosed with a CDLN 18.2-expressing tumor (such as solid tumor) or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) and/or a disease associated with abnormal CLDN18.2 expression or activity. In certain embodiments, the subject to whom an anti-CLDN18.2 antibody described herein (or an antigen-binding fragment thereof) is administered is resistant to claudiximab (IMAB362) or its biosimilar. In certain embodiments, the subject to whom an anti-CLDN18.2 antibody described herein (or an antigen-binding fragment thereof) is administered has progressed on claudiximab (IMAB362) or its biosimilar. In certain embodiments, the subject to whom an anti-CLDN18.2 antibody described herein (or an antigen-binding fragment thereof) is administered is refractory to claudiximab (IMAB362) or its biosimilar.

Many diagnostic methods for CDLN 18.2-expressing tumor (such as solid tumor) or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) or other disease associated with abnormal CLDN18.2 activity and the clinical delineation of those diseases are known in the art. Such methods include, but are not limited to, e.g., immunohistochemistry, PCR, fluorescent in situ hybridization (FISH). Additional details regarding such diagnostic methods for assessing abnormal CLDN18.2 activity or expression are described in, e.g., Gupta et al. (2009) *Mod Pathol.* 22(1): 128-133; Lopez-Rios et al. (2013) *J Clin Pathol.* 66(5): 381-385; Ellison et al. (2013) J Clin Pathol 66(2): 79-89; and Guha et al. (2013) *PLoS ONE* 8(6): e67782.

An anti-CLDN18.2 antibody described herein (or an antigen-binding fragment thereof) may be administered using any suitable route including, e.g., intravenous, intramuscular, or subcutaneous. In some embodiments, an anti-CLDN18.2 antibody (or an antigen-binding fragment thereof) provided herein is administered in combination with a second, third, or fourth agent (including, e.g., an antineoplastic agent, a growth inhibitory agent, a cytotoxic agent, or a chemotherapeutic agent) to treat the diseases or disorders associated with abnormal CLDN18.2 activity. Such agents include, but are not limited to, e.g., docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4 (infusional fluorouracil, leucovorin, and oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm. In some embodiments, an anti-CLDN18.2 antibody provided herein (or an antigen-binding fragment thereof) is conjugated to an antineoplastic agent, a growth inhibitory agent, a cytotoxic agent, or a chemotherapeutic agent.

In certain embodiments, an anti-CLDN18.2 antibody (or an antigen-binding fragment thereof) provided herein is administered in combination with one or more additional therapies, such as radiation therapy, surgery, chemotherapy, and/or targeted therapy. In certain embodiments, an anti-CLDN18.2 antibody (or an antigen-binding fragment thereof) provided herein are administered in combination with chemotherapy. In certain embodiments, the chemotherapy comprises EOX (i.e., epirubicin, oxaliplatin, and capecitabine). In certain embodiments, the chemotherapy comprises zoledronic acid and interleukin-2.

Depending on the indication to be treated and factors relevant to the dosing that a physician of skill in the field would be familiar with, the antibodies provided herein will be administered at a dosage that is efficacious for the treatment of that indication while minimizing toxicity and side effects. For the treatment of a CDLN 18.2-expressing tumor (such as solid tumor) or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.), a typical dose may be, for example, in the rage of 0.001 to 1000 µg; however, doses below or above this exemplary range are within the scope of the methods of treatment described herein. The dose may be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values, including any range between the foregoing values). In some embodiments, a typical dose may be, e.g., between 10 $mg/m^2$ and 1500 $mg/m^2$; however, doses below or above this exemplary range are within the scope of the methods of treatment described herein. A dose may be about 25 $mg/m^2$ to about 1000 $mg/m^2$ (e.g., about 25 $mg/m^2$, about 100 $mg/m^2$, about 250 $mg/m^2$, about 500 $mg/m^2$, about 750 $mg/m^2$, or a range defined by any two of the foregoing values, including any range between the foregoing values). In some embodiments, the dose is about any one of 300 $mg/m^2$, 600 $mg/m^2$, 800 $mg/m^2$, or 1000 $mg/m^2$.

An anti-CLDN18.2 antibody (or an antigen-binding fragment thereof) provided herein may be administered in a single daily dose, or the total daily dose may be administered in divided dosages of two, three, or four times daily. Alternatively, the anti-CLDN18.2 antibody (or an antigen-binding fragment thereof) may be administered less frequently than daily, for example, six times a week, five times a week, four times a week, three times a week, twice a week, once a week, once every two weeks, once every three weeks, once every four weeks, once a month, once every two months, once every three months, or once every six months.

In some embodiments, an anti-CLDN18.2 antibody (or an antigen-binding fragment thereof) provided herein is administered once at a dose of 800 $mg/m^2$ during a first cycle, followed by once at a dose of 600 $mg/m^2$ every three weeks or 21 days thereafter. In some embodiments, an anti-CLDN18.2 antibody (or an antigen-binding fragment thereof) provided herein is administered once every three weeks or 21 days at a dose of 1000 $mg/m^2$. In some embodiments, an anti-CLDN18.2 antibody (or an antigen-binding fragment thereof) provided herein is administered at a dose of 800 $mg/m^2$ on day 1 of cycle 1, followed by a dose of 600 $mg/m^2$ on day 1 of every other subsequent cycle.

Therapeutic or prophylactic efficacy can be monitored by periodic assessment of subjects receiving treatment. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of an anti-CLDN18.2 antibody (or an antigen-binding fragment thereof) provided herein, by multiple bolus administrations of an anti-CLDN18.2 antibody (or an antigen-binding fragment thereof) provided herein, or by continuous infusion administration of an anti-CLDN18.2 antibody (or an antigen-binding fragment thereof) provided herein.

Cancer treatments can be evaluated by, e.g., but not limited to, tumor regression, tumor weight or size shrinkage, time to progression, rate of remission, duration of survival, progression free survival, overall response rate, overall survival, duration of response, disease control rate, clinical benefit rate, quality of life, amount or level of CLDN18.2 expression, and/or level of CLDN18.2 activity. Approaches to determining efficacy of the therapy can be employed, including for example, measurement of response through, e.g., RECIST (Response Evaluation in Solid Tumors) criteria (see, e.g., Eisenhauer et al. (2009) "New response evaluation in solid tumors: Revised RECIST guideline (version 1.1)." *Eur J. Cancer.* 45: 228-247.

Anti-CLDN18.2 CAR Effector Cell Therapy

The present invention also provides a method of stimulating an effector cell-mediated response (such as a T cell-, NK cell- or macrophage-mediated immune response) to a target cell population or tissue comprising CLDN18.2-presenting cells in an individual, comprising the step of administering to the individual an effector cell (such as a T cell) that expresses an anti-CLDN18.2 CAR. In some embodiments, the individual is a human individual.

Anti-CLDN18.2 CAR effector cells (such as T cells, NK cells, and/or macrophages) expressing the anti-CLDN18.2 CAR can be infused to a recipient in need thereof. In some embodiments, anti-CLDN18.2 CAR effector cells (such as T cells, NK cells, and/or macrophages) are able to replicate in vivo resulting in long-term persistence that can lead to sustained tumor control. In some embodiments, the anti-CLDN18.2 CAR effector cells can undergo robust in vivo T cell expansion and persist for an extended amount of time. In some embodiments, the anti-CLDN18.2 CAR T cells of the invention develop into specific memory T cells that can be reactivated to inhibit any additional tumor formation or growth.

Ex vivo procedures are well known in the art. Briefly, cells are isolated from an individual (for example a human) and modified with a vector or mRNA expressing an anti-CLDN18.2 CAR disclosed herein. The anti-CLDN18.2 CAR cell can be administered to a mammalian recipient to provide a therapeutic benefit. The mammalian recipient may be a human and the anti-CLDN18.2 CAR cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art; therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

The anti-CLDN18.2 CAR effector cells (such as T cells) of the present invention may be administered either alone, or as a pharmaceutical composition in combination with diluents and/or with other components such as IL-2 or other cytokines or cell populations. Briefly, pharmaceutical compositions of the present invention may comprise anti-CLDN18.2 CAR effector cells (such as T cells), in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, anti-CLDN18.2 CAR effector cell (such as T cell) compositions are formulated for intravenous administration.

The precise amount of the anti-CLDN18.2 CAR effector cell (such as T cell) compositions of the present invention to be administered can be determined by a physician with consideration of individual differences in age, weight, tumor size, extent of infection or metastasis, and condition of the patient (subject). In some embodiments, a pharmaceutical composition comprising the anti-CLDN18.2 CAR effector cells (such as T cells) is administered at a dosage of about $10^4$ to about $10^9$ cells/kg body weight, such any of about $10^4$ to about $10^5$, about $10^5$ to about $10^6$, about $10^6$ to about $10^7$, about $10^7$ to about $10^8$, or about $10^8$ to about $10^9$ cells/kg body weight, including all integer values within those ranges. Anti-CLDN18.2 CAR effect cell (such as T cell) compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

The administration of the anti-CLDN18.2 CAR effector cells (such as T cells) may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the anti-CLDN18.2 CAR effector cell (such as T cell) compositions of the present invention are administered to a patient by intradermal or subcutaneous injection. In some embodiments, the anti-CLDN18.2 CAR effector cell (such as T cell) compositions of the present invention are administered by i.v. injection. The compositions of anti-CLDN18.2 CAR effector cells (such as T cells) may be injected directly into a tumor, lymph node, or site of infection.

Thus, for example, in some embodiments, there is provided a method of treating a disease (such as cancer) in an individual comprising administering to the individual an effective amount of a composition comprising an effector cell (such as a T cell) expressing an anti-CLDN18.2 CAR comprising a) an extracellular domain comprising an anti-CLDN18.2 antibody moiety that specifically binds to CLDN18.2, b) a transmembrane domain, and c) an intracellular signaling domain comprising a CD3ζ intracellular signaling sequence and a 4-1BB intracellular signaling sequence. In some embodiments, the individual is positive for CLDN18.2. In some embodiments, the individual expresses a high level of CLDN18.2 as compared to the medium level in a patient population. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of priming T cells in an individual comprising administering to the individual an effective amount of a composition comprising an effector cell (such as a T cell) expressing an anti-CLDN18.2 CAR according to any of the anti-CLDN18.2 CARs described above. In some embodiments, individual has cancer. In some embodiments, the administration is via intravenous, intraperitoneal, or intratumoral route. In some embodiments, the administration is via intravenous route. In some embodiments, the administration is via intratumoral route. In some embodiments, the individual is human.

Pharmaceutical Formulations

The anti-CLDN18.2 antibodies (or fragments thereof) provided herein can be formulated with pharmaceutically acceptable carriers or excipients so that they are suitable for administration to a subject in need thereof (e.g., a mammal such as a human). Suitable formulations of the antibodies are obtained by mixing an antibody (or fragment thereof) having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Pharmaceutically acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The antibodies disclosed herein can also be formulated as immunoliposomes. Liposomes containing the antibody are prepared by methods known in the art, such as described in Epstein et al., *PNAS USA,* 82: 3688 (1985); Hwang et al., *PNAS USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. An anti-neoplastic agent, a growth inhibitory agent, or a chemotherapeutic agent (such as doxorubicin) is optionally also contained within the liposome. See, Gabizon et al., J. National Cancer Inst., 81(19): 1484 (1989).

A pharmaceutical formulation comprising an anti-CLDN18.2 antibody described herein may also contain more than one active compound as necessary for the particular indication being treated, preferably those with complementary activities that do not adversely affect each other. For example, it may be desirable to provide an anti-neoplastic agent, a growth inhibitory agent, a cytotoxic agent, or a chemotherapeutic agent in addition to an anti-CLDN18.2 antibody described herein. Such molecules are suitably present in combination in amounts that are effective for the purpose intended. The effective amount of such other agents depends on the amount of antibody present in the formulation, the type of disease or disorder or treatment, and other factors discussed above. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

In some embodiments, an antibody of the present disclosure is lyophilized. Such lyophilized formulations may be reconstituted with a suitable diluent to a high protein concentration, and the reconstituted formulation may be administered to a mammal (such as a human).

In certain embodiments, the pharmaceutical formulations to be used for in vivo administration are sterile. This is readily accomplished by, e.g., filtering a solution comprising an anti-CLDN18.2 antibody described herein through sterile filtration membranes.

Methods of Diagnosis and Imaging Using Anti-Claudin 18.2 Antibodies

Labeled anti-CLDN18.2 antibodies, fragments thereof, and derivatives and analogs thereof, which specifically bind to a CLDN18.2 polypeptide can be used for diagnostic purposes to detect, diagnose, or monitor diseases and/or disorders associated with the expression, aberrant expression and/or activity of CLDN18.2. For example, the anti-CLDN18.2 antibodies (or fragments thereof) provided herein can be used in in situ, in vivo, ex vivo, and in vitro diagnostic assays or imaging assays. Methods for detecting expression of a CLDN18.2 polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression. Such assays can be performed in vivo or ex vivo, e.g., using a sample obtained from a patient.

Also provided herein are methods of diagnosing a disease or disorder associated with expression or aberrant expression of CLDN18.2 in an animal (e.g., a mammal such as a human). In some embodiments, the methods comprise detecting CLDN18.2 polypeptides in the mammal. In certain embodiments, diagnosis comprises: (a) administering an effective amount of a labeled anti-CLDN18.2 antibody (or fragment thereof) to a mammal (b) waiting for an interval of time following the administration step to permit the labeled anti-CLDN18.2 antibody (or fragment thereof) to preferentially concentrate at sites in the subject where CLDN18.2 is expressed (and/or for unbound labeled molecule to be cleared to background level); (d) detecting an amount or level of labeled anti-CLDN18.2 antibody in the subject, and (e) comparing the amount or level of labeled anti-CLDN18.2 antibody in the subject to a level or amount of anti-CLDN18.2 antibody in a healthy control subject. If the amount or level of the labeled anti-CLDN18.2 antibody in the subject exceeds the amount or level of anti-CLDN18.2 antibody in a healthy control subject, this may indicate that the subject has a disease or disorder associated with expression or aberrant expression of CLDN18.2.

Anti-CLDN18.2 antibodies (or fragments thereof) provided herein can be used to assay amounts or levels of CLDN18.2 in a biological sample using classical immunohistological methods known to those of skill in the art (e.g., see Jalkanen, et al., $J.$ $Cell.$ $Biol.$ 101:976-985 (1985); Jalkanen, et al., $J.$ $Cell.$ $Biol.$ 105:3087-3096 (1987)). Other antibody-based methods useful for detecting CLDN18.2 expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I) carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

In some embodiments, CLDN18.2 overexpression is measured by determining an amount of shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., $J.$ $Immunol.$ $Methods$ 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the can be evaluated, e.g., by external scanning for radioactivity or by analyzing a sample (e.g., a biopsy or other biological sample) taken from a mammal previously exposed to the antibody.

CAR Effector Cell Preparation

The present invention in one aspect provides effector cells (such as T cells, NK cells, and/or macrophages) expressing an anti-CLDN18.2 CAR. Exemplary methods of preparing effector cells (such as T cells, NK cells, and/or macrophages) expressing the anti-CLDN18.2 CARs (anti-CLDN18.2 CAR effector cells, such as anti-CLDN18.2 CAR T cells, anti-CLDN18.2 CAR NK cells, and/or anti-CLDN18.2 CAR macrophages) are provided herein.

In some embodiments, an anti-CLDN18.2 CAR effector cell (such as T cell, NK cell, or macrophage) can be generated by introducing a vector (including for example a lentiviral vector) comprising an anti-CLDN18.2 CAR (for example a CAR comprising an anti-CLDN18.2 antibody moiety, a 4-1BB co-stimulatory sequence, and CD3ζ primary signaling sequence or other sequences such as IL-2, IL15 that could prolong CAR cell survival or sequences that could eliminate CAR cells) into the effector cell (such as T cell, NK cell, or macrophage). In some embodiments, the anti-CLDN18.2 CAR effector cells (such as T cells, NK cells, and/or macrophages) of the invention are able to replicate in vivo. In some embodiments, the anti-CLDN18.2 CAR effector cell (such as T cell, NK cell, or macrophage) can be generated by introducing an mRNA encoding an anti-CLDN18.2 CAR (for example a CAR comprising an anti-CLDN18.2 antibody moiety, a 4-1BB co-stimulatory sequence, and CD3ζ primary signaling sequence) into the effector cell (such as T cell, NK cell, and/or macrophage).

The anti-CLDN18.2 CAR T cells of the invention can undergo robust in vivo T cell expansion and can establish CLDN18.2-specific memory cells that persist at high levels for an extended amount of time in blood and bone marrow. In some embodiments, the anti-CLDN18.2 CAR T cells of the invention infused into a patient can eliminate CLDN18.2-presenting cells, such as CLDN18.2-presenting cancer cells, in vivo in patients having the disease (for example a disease characterized by high CLDN18.2 expression).

Prior to expansion and genetic modification of the T cells, NK cells, or macrophages, a source of T cells, NK cells, or macrophages is obtained from a subject. For example, T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell, NK cell, and/or macrophage cell lines available in the art may be used. In some embodiments of the present invention, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ density gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. Multiple rounds of selection may be used.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected.

Articles of Manufacture and Kits

Provided is an article of manufacture comprising materials useful for the treatment of CDLN 18.2-expressing tumor (such as solid tumor) or cancer, such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.

In certain embodiments, the article of manufacture or kit comprises a container containing one or more of the anti-CLDN18.2 antibodies or the compositions described herein. In certain embodiments, the article of manufacture or kit comprises a container containing nucleic acids(s) encoding one (or more) of the anti-CLDN18.2 antibodies or the compositions described herein. In some embodiments, the kit includes a cell of cell line that produces an anti-CLDN18.2 antibody as described herein. In some embodiments, the kit includes one or more positive controls, for example CLDN18.2 (or fragments thereof) or CLDN18.2+ cells. In some embodiments, the kit includes negative controls, for example a surface or solution that is substantially free of CLDN18.2.

In certain embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing CDLN 18.2-expressing tumor (such as solid tumor) or cancer (e.g. gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.) and may have a sterile access port (for example the container may be an intravenous solution bag or a vial having a stopper pierceable by a hypodermic injection needle). At least one agent in the composition is an anti-CLDN18.2 antibody described herein. The label or package insert indicates that the composition is used for treating a CDLN 18.2-expressing tumor (such as solid tumor) or cancer (such as gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer, etc.).

Moreover, the article of manufacture or kit may comprise (a) a first container with a composition contained therein, wherein the composition comprises an anti-CLDN18.2 antibody described herein; and (b) a second container with a composition contained therein, wherein the composition comprises a further cytotoxic or otherwise therapeutic agent. In some embodiments, the therapeutic agent is an immunotherapeutic agent, as described herein. Additionally, the article of manufacture may further comprise an additional container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture or kits may include an immunoconjugate described herein in place of (or in addition to) an anti-CLDN18.2 antibody.

Kits are also provided that are useful for various purposes, e.g., for isolation or detection of CLDN18.2 inpatients, optionally in combination with the articles of manufacture. For isolation and purification of CLDN18.2, the kit can contain an anti-CLDN18.2 antibody (or fragment thereof) provided herein coupled to beads (e.g., sepharose beads). Kits can be provided which contain the antibodies (or fragments thereof) for detection and quantitation of CLDN18.2 in vitro, e.g., in an ELISA or a Western blot. As with the article of manufacture, the kit comprises a container and a label or package insert on or associated with the container. For example, the container holds a composition comprising at least one anti-CLDN18.2 antibody provided herein. Additional containers may be included that contain, e.g., diluents and buffers, control antibodies. The label or package insert may provide a description of the composition as well as instructions for the intended in vitro or diagnostic use.

EXAMPLES

Example 1. Generation and Characterization of Anti-Claudin 18.2 (CLIDN18.2) Antibodies Ubercells™ overexpressing CLDN18.2 tagged with two tolerance-breaking T-cell epitopes were used to immunize NZB/W F1 mice. Plasma titers were analyzed via FACS against HEK293-CLDN18.2 stable cells. Spleens were collected after the final titer measurement, pooled and fused to myeloma cells to generate hybridomas. Ten days after fusion, hybridoma supernatants were screened by FACS against HEK293-CLDN18.2, HEK293-CLDN18.1 and HEK293. Hybridomas showed diverse binding affinity and selectivity to CLDN18.2. Of the 102 hybridoma supernatants that were screened, 33 contained antibodies that selectively bound to CLDN18.2; 46 contained antibodies that bound with almost equal affinity to both CLDN18.2 and CLDN18.1; and 9 contained antibodies that demonstrated poor interaction with CLDN18.2. See FIG. 1 (MFI=mean fluorescence intensity). The data shown in FIG. 1 is also provided in Table 5 below.

TABLE 5

Mean Fluorescence Intensities of Antibody Binding to
HEK293-CLDN18.2, HEK293-CLDN18.1, and HEK293 Cells

| Antibody | MFI of binding to HEK293-CLDN18.2 | MFI of binding to HEK293-CLDN18.1 | MFI of binding to HEK293 |
|---|---|---|---|
| 10-J10 | 135912 | 20390 | 4644 |
| 7-G17 | 135729 | 12920 | 3690 |
| 10-P12 | 130747 | 20101 | 4489 |
| 10-L9 | 127207 | 14320 | 3656 |
| 7-B15 | 105051 | 11238 | 3694 |
| 9-C2 | 103897 | 12559 | 4209 |
| 6-C5 | 94682 | 8133 | 4226 |
| 4-N1 | 80146 | 12064 | 3896 |
| 6-P2 | 79668 | 14639 | 4076 |
| 7-E20 | 72565 | 7462 | 3738 |
| 9-M7 | 70304 | 7745 | 3322 |

TABLE 5-continued

Mean Fluorescence Intensities of Antibody Binding to
HEK293-CLDN18.2, HEK293-CLDN18.1, and HEK293 Cells

| Antibody | MFI of binding to HEK293-CLDN18.2 | MFI of binding to HEK293-CLDN18.1 | MFI of binding to HEK293 |
|---|---|---|---|
| 7-I14 | 67615 | 12342 | 3226 |
| 9-N14 | 64023 | 10553 | 4178 |
| 1-B13 | 61855 | 10208 | 3217 |
| 9-A13 | 61440 | 6926 | 4209 |
| 6-M11 | 60487 | 8969 | 3880 |
| 1-M5 | 59214 | 7948 | 2896 |
| 10-P2 | 58885 | 10887 | 3870 |
| 2-D22 | 58347 | 6308 | 4539 |
| 9-B11 | 54068 | 7633 | 3368 |
| 9-C6 | 52368 | 9700 | 4345 |
| 10-K12 | 48904 | 7911 | 4066 |
| 9-M6 | 48307 | 8584 | 3388 |
| 2-A9 | 47117 | 8876 | 3315 |
| 7-A21 | 46953 | 6454 | 3709 |
| 2-J15 | 46324 | 6943 | 4206 |
| 5-J22 | 46062 | 6386 | 3806 |
| 9-F11 | 44257 | 6944 | 3632 |
| 4-O20 | 43547 | 7224 | 3491 |
| 5-C11 | 43365 | 6888 | 3784 |
| 9-K11 | 40865 | 7016 | 3948 |
| 8-I24 | 39747 | 7966 | 3905 |
| 7-L9 | 38150 | 6783 | 3860 |
| 1-H16 | 121331 | 28327 | 4352 |
| 10-I12 | 119285 | 26758 | 4896 |
| 4-F18 | 109402 | 32276 | 7730 |
| 1-F6 | 58023 | 12895 | 3606 |
| 6-D1 | 50036 | 11955 | 4553 |
| 7-P4 | 49940 | 15289 | 4320 |
| 8-H4 | 48962 | 13534 | 3783 |
| 4-P21 | 44558 | 9387 | 4188 |
| 8-M8 | 39238 | 8576 | 4214 |
| 9-N3 | 38760 | 7858 | 4194 |
| 8-P15 | 37566 | 8060 | 3236 |
| 3-I12 | 30467 | 6751 | 3528 |
| 5-P2 | 28798 | 8537 | 3893 |
| 5-A20 | 26276 | 7676 | 3852 |
| 8-O21 | 26788 | 9630 | 3919 |
| 9-A23 | 33448 | 13815 | 4007 |
| 4-N12 | 29932 | 18913 | 3473 |
| 5-K2 | 30525 | 19294 | 9235 |
| 5-E17 | 51358 | 20172 | 4041 |
| 8-P13 | 44820 | 20573 | 4083 |
| 8-A15 | 53377 | 20821 | 5354 |
| 7-F11 | 39614 | 21398 | 4755 |
| 10-P6 | 52629 | 23578 | 3662 |
| 5-M3 | 63292 | 26358 | 3975 |
| 4-P18 | 52880 | 27341 | 3810 |
| 6-A10 | 89301 | 32530 | 5350 |
| 6-H21 | 29823 | 37507 | 3526 |
| 1-N20 | 57726 | 44276 | 4221 |
| 6-C16 | 59549 | 44809 | 6146 |
| 4-D1 | 102729 | 46446 | 3789 |
| 4-D4 | 35581 | 49168 | 4019 |
| 1-E13 | 50803 | 51843 | 5728 |
| 10-H21 | 30594 | 53489 | 15203 |
| 3-L3 | 35070 | 57621 | 3561 |
| 6-N13 | 48314 | 64702 | 3768 |
| 8-J1 | 44928 | 69748 | 3663 |
| 9-I23 | 43532 | 72107 | 3773 |
| 4-N19 | 48453 | 77540 | 4319 |
| 2-L5 | 49404 | 78753 | 3204 |
| 10-J17 | 45533 | 79229 | 3467 |
| 4-K18 | 37286 | 79928 | 3880 |
| 3-G18 | 37057 | 82686 | 4219 |
| 10-N3 | 114234 | 87051 | 8823 |
| 7-L14 | 50201 | 90572 | 3606 |
| 2-A5 | 49693 | 92444 | 5849 |
| 2-C20 | 50222 | 92934 | 3794 |
| 8-K19 | 48908 | 93411 | 4065 |
| 1-I19 | 73756 | 110453 | 4573 |
| 8-O3 | 35337 | 113110 | 7076 |
| 9-B7 | 54131 | 114703 | 4409 |
| 5-K4 | 70828 | 126401 | 4852 |
| 1-C11 | 71919 | 131244 | 5226 |
| 1-L3 | 80498 | 133274 | 3901 |
| 2-L19 | 47855 | 137503 | 4504 |
| 1-G10 | 52185 | 142540 | 4832 |
| 7-J5 | 76832 | 148050 | 6615 |
| 9-P3 | 123284 | 162177 | 7064 |
| 1-H9 | 144871 | 169034 | 10063 |
| 9-M14 | 48093 | 171134 | 8629 |
| 2-F13 | 137980 | 232194 | 6061 |
| 7-B7 | 15741 | 21276 | 10258 |
| 5-M7 | 12352 | 6473 | 4707 |
| 5-M5 | 12113 | 23583 | 8091 |
| 7-M12 | 11939 | 25387 | 5648 |
| 5-J8 | 11347 | 24742 | 5498 |
| 2-E2 | 11181 | 30692 | 4109 |
| 6-O15 | 6198 | 11448 | 3618 |
| 10-C17 | 4921 | 7570 | 4278 |
| 10-C6 | 3801 | 6514 | 3420 |

Next, the EC50 values of 20 hybridoma clone supernatants to CLDN18.2 were determined via in-cell ELISA. The supernatant of hybridoma 5K41B, which contains an antibody that binds to both CLDN18.1 and CLDN18.2 (see FIG. 1) was used as a positive control. In-cell ELISAs were performed as follows: $5 \times 10^3$ HEK293-CLDN18.2 cells were seeded per well in a poly-L-lysine-coated 96-well plate. The plates were then incubated at 37° C. with 5% $CO_2$ for 2 days. Following incubation, culture media was removed from each well, and the HEK293-CLDN18.2 cells were blocked with 200 μl blocking buffer (3% BSA/PBS (pH 7.4)) per well for 1 hour at room temperature. Each hybridoma supernatant was incubated with cells at room temperature for 1 hour. Cells were gently washed 3 times with 200 μl PBS (pH 7.4) containing 1 mM $Ca^{2+}$ and 0.5 mM $Mg^{2+}$. Next, cells were incubated with 100 μl of HRP-conjugated goat anti-human IgG (H+L) antibody for 1 hour at room temperature. Following the incubation, the cells were washed three times with 200 μl PBS (pH 7.4) containing 1 mM $Ca^{2+}$ and 0.5 mM $Mg^{2+}$. 100 μl of 1-Step™ Ultra TMB-ELISA Substrate was added to each well, and the reactions were stopped by addition of 50 μl of stop solution. $OD_{450}$ was measured using CLARIOStar microplate reader. The in-cell ELISAs were repeated for each clone using HEK293-CLDN18.1 cells. The results are shown in Table 6 below.

TABLE 6

| Hybridoma Clone | Binding to CLDN18.2 OD450/μg IgG | Binding to CLDN 18.1 OD450/μg IgG |
|---|---|---|
| mouse IgG (control) | 3.23 | 1.54 |
| 10-K12-A | 12.90 | 2.11 |
| 10-L9-A | 9.52 | 0.62 |
| 10-P2-A | 4.71 | 0.34 |
| 1-M5-A | 21.07 | 1.11 |
| 2-D22-A | 16.78 | 2.22 |
| 4-N1-A | 17.97 | 2.87 |
| 5-J22-A | 15.43 | 2.16 |
| 6-C5-A | 12.19 | 1.04 |
| 6-M11-A | 11.43 | 1.55 |
| 7-A21-A | 18.41 | 2.51 |
| 7-B15-A | 13.18 | 1.32 |
| 7-E20-A | 20.35 | 2.23 |
| 7-G17-A | 30.84 | 6.70 |
| 9-A13-B | 48.63 | 3.34 |

TABLE 6-continued

| Hybridoma Clone | Binding to CLDN18.2 OD450/μg IgG | Binding to CLDN 18.1 OD450/μg IgG |
|---|---|---|
| 9-B11-A | 25.95 | 2.18 |
| 9-C6-A | 28.30 | 3.82 |
| 9-M7-A | 19.24 | 0.79 |
| 9-N14-A | 34.42 | 3.14 |
| 10-J10-B | 101.53 | 3.05 |
| 10-P12-A | 29.35 | 4.30 |
| 1-H16-A | 14.17 | 1.05 |
| 2-F13-A | 6.49 | 13.34 |
| 5-K4-B | 88.24 | 139.10 |

Hybridomas producing antibodies that bound CLDN18.2 but not CLDN18.1 or antibodies that preferentially bound CLDN18.2 over CLDN18.1 were selected for cloning. Hybridomas 5K4B and 2F13A, which demonstrated strong binding to both CLDN18.2 and CLD18.1 were also selected for cloning. Briefly, 1 cell from each hybridoma tested in Table 6, and hybridoma 1B13A, was seeded per well in 384-well plates. Supernatants from the expanded clones were screened by FACS to re-confirm binding to CLDN18.2. DNA fragments encoding the heavy chain variable domain (VH) and light chain variable domain (VL) from clonal hybridomas showing high affinity for CLDN18.2 were amplified via 5' RACE, TOPO cloned, and sequenced. The amino acid sequences of the VH domains of the clones are shown in Table 7, and the amino acid sequences of the VL domains of the clones are shown in Table 8 (CDRs are bolded an underlined).

TABLE 7

| | VH SEQUENCES |
|---|---|
| 10K12A | EVQLVESGGGLVKPGGSRKLSCAASGFTFSDYGMFWVRQAPEK<br>GLEWVGYISSGSSNIYYADTVKGRFTISRDNAKNTLFLQMTSL<br>RSEDTAMYYCARIARGNAMDYWGQGTSVTVSS<br>(SEQ ID NO: 72) |
| 10L9A | EVQLVESGGGLVKPGGSRKLSCAASGFTFSDYGMHWVRQAPEK<br>GLEWIAYINSGSSTIYYADTVKGRFTISRDNAKNTLFLQMTSL<br>RSEDTAMFYCARFARGNVLDYWGQGTSVTVSS<br>(SEQ ID NO: 73) |
| 10P2A | EVQLQQSGPALVKPGASVKMSCKASGYSFTGYNIHWVKQSHGK<br>SLEWIGYIDPNNGVTYSNQKFKGKATLTVDKSSSTAYMQLNSL<br>TSEDSAVYYCARPYYGNSFDYWGQGTTLTVSS<br>(SEQ ID NO: 74) |
| 1B13A | QVQLQQSGAELARPGASVKLSCKASGYTFTVWSMSWVKQRTGQ<br>GLQWIGEIYPKSGNTHYNEKFKGKATLTADKSSSTVYMQLSSL<br>TSEDSAVYFCARAAYYGNSFAYWGQGTLVTVPA<br>(SEQ ID NO: 75) |
| 1M5A | EVQLVESGGALVKSGGSLRLSCAASGFTFSNNAMSWIRQTPEK<br>RLEWVATIIGGTYTYYPDSVKGRFTISRDNAKNTLYLQMSSL<br>RSEDTAFYYCARQVYGNSFAYWGQGTLVSVSA<br>(SEQ ID NO: 76) |
| 2D22A | EVQLVESGGGLVKPGGSRKLSCAASGFTFSDYGMHWVRQAPEK<br>GLEWIAYISSGSSSIYYADTVKGRFTMSRDNAKKTLFLQTTSL<br>RSEDTAMYYCARIARGNAMDYWGQGTSVTVTS<br>(SEQ ID NO: 77) |
| 4N1A | EVQLVNSGGGLVKPGGSRKLSCAASGFTFSDYGMHWVRQAPEK<br>GLEWVAYISSGSSTIYYADTMKGRFTISRDNAKNTLFLQMTSL<br>RSEDTAMYYCARFVRGNSMDYWGQGTSVTVSS<br>(SEQ ID NO: 78) |
| 5J22A | EVQLVESGGGLVKPGGSRKLSCAASGFTFSDYGMHWVRQAPEK<br>GLEWVAHISSGSNIIHYADTLKGRFTISRDNAKNTLFLQMTSL<br>RSEDTAMYYCARFARGNTMDYWGQGTSVTVSS<br>(SEQ ID NO: 79) |

TABLE 7-continued

| | VH SEQUENCES |
|---|---|
| 6C5A | EVQLVESGGGLVKPGGSRKLSCAASGFTFSDYGMHWVRQAPEK<br>GLEWVAYISSGSSTIYYADTMKGRFTISRDNAKNTLFLQMTSL<br>RSEDTAMYYCTRFARGNTMDYWGQGTSVTVSS<br>(SEQ ID NO: 80) |
| 6M11A | EVQLVESGGGSVKPGGSRKLSCAASGFTFSDYGMHWVRQAPEK<br>GLEWVAYISSGSNTFYYTDTVKGRFTISRDNAKNTLFLQMTGL<br>RSEDTAMYYCARFTRGNALDYWGQGTSVTVSS<br>(SEQ ID NO: 81) |
| 7A21A | EVQLVESGGGLVKPGGSRKLSCAASGFTFSDYGMYWVRQAPEK<br>GLEWLAYISSGSNTIYYADTVKGRFTISRDNAKNTLFLQMTSL<br>RSEDTAMYYCARIARGNAMDYWGQGTSVTVSS<br>(SEQ ID NO: 82) |
| 7B15A | EVQLVESGGGLVKPGGSRKLSCAASGFTFSDYGMHWVRQAPEK<br>GLEWIAHISSGSSTIYYADTMKGRFTISRDNAKNTLFLQMTSL<br>RSEDTAMYYCARFVRGNALDYWGQGTSVTVSS<br>(SEQ ID NO: 83) |
| 7E20A | EVQLVESGGGLVKPGGSRKLSCAASGFTFSDYGMHWVRQAPEK<br>GLEWVAYISSGSSTIHYVDTMKGRFTISRDNAKNTLFLQMTSL<br>RSEDTAMYYCARFARGNTLDYWGQGTSVTVSS<br>(SEQ ID NO: 84) |
| 7G17A | EVQLVESGGGLVKPGGSRKLSCAVSGFTFSDYGMYWVRQAPEK<br>GLEWVAYISSGSSTIYYADTVKGRFTMSRDNAKNTLFLQMTSL<br>RSEDTAMYYCARIARGNANDYWGQGTSVTVSS<br>(SEQ ID NO: 85) |
| 9A13B | EVQLVESGGGLVKPGGSRKLSCAASGFSFSDYGMHWVRQAPEK<br>GLEWVAHISSGSSTIYYADTVKGRFTISRDNAKNTLFLQMTSL<br>RSEDTAMYYCARFARGNTMDYWGQGTSVTVSS<br>(SEQ ID NO: 86) |
| 9B11A | EVQLVESGGGLVKPGGSRKLSCAASGFTFSDYGMHWVRQAPEK<br>GLEWVAYISSGSSPIYYADTVKGRFTISRDNAKNTLFLQMTSL<br>RSEDTAMYYCARFARGNANDYWGQGTSVTVSS<br>(SEQ ID NO: 87) |
| 9C6A | EVQLVESGGGLVKPGGSRKLSCAASGFTFSDYGMHWVRQAPEK<br>GLEWVAYISSGSSTIYYADTMKGRFTISRDNAKNTLFLQMTSL<br>RSEDTAMYYCARFVRGNSMDYWGQGTSVTVSS<br>(SEQ ID NO: 88) |
| 9M7A | EVQLVESGGALVKPGGSLKLSCAASGFTFSNYAMSWIRQTPEK<br>RLEWVATIIIGGTYTYYPDSVKGRFTISRDNAKNTLYLQMSSL<br>RSEDTALYYCARQVYGNSFAYWGQGTLVTVSA<br>(SEQ ID NO: 89)f |
| 9N14A | EVQLVESGGGLVKPGGSRKLSCAASGFTFSDYGMYWVRQAPEK<br>GLEWLAYISSGSNNIYYADTVKGRFTISRDNAKNTLFLQMTSL<br>RSEDTAMYYCARIARGNANDYWGQGTSVTVSS<br>(SEQ ID NO: 90) |
| 10J10B | QVQLQQSGAELARPGASVKLSCKASGYTFTSWSISWVKQRTGQ<br>GLEWIGEIYPRSDNIHYNEKFKGKATLTADKSSSTVYMQLSSL<br>TSEDSAVYFCARAYYGNSFAYWGQGTLVTVSA<br>(SEQ ID NO: 91) |
| 10P12A | EIQLQQSGAELVKPGTSVKISCKASGYSFTGYNMNWVKQSHGK<br>SLEWIGNINPYYSNTNYNQRFKGKATLTVDKSSSTAYMQLNSL<br>TSEDSAVYYCARHVRGNSFDYWGQGTTLTVSS<br>(SEQ ID NO: 92) |
| 1H16A | EVQLVESGGGLVKPGGSRKLSCAASGFTFSDYGMYWVRQAPEK<br>GLEWVAFISSGSSTIYCADTVKGRFTISRDNAKNTLFLQMTSL<br>RSEDTAMYYCARIARGNAMDYWGQGTSVTVSS<br>(SEQ ID NO: 93) |
| 5K4B | EVQLQQSGPELVKPGASVKMSCKASGYTFISYLIHWVKQPGQ<br>GLEWIGYINPYNDGTKYNEKFKGKATLTSDKSSSTASMEFSSL<br>TSEDSAVYYCTRGDFWGQGTTLTVSS<br>(SEQ ID NO: 135) |

TABLE 7-continued

VH SEQUENCES

| | |
|---|---|
| 2F13A | EVQLQQSGPELVKPGASVKMSCKASGYTFTNYVMHWVKQKPGQ GLEWIGYINPFDDGTKYNEKFKGKATLTSDKSSSTAYMELSSL TSEDSAVYYCTRGDYWGQGTTLTVSS (SEQ ID NO: 136) |

TABLE 8

VL SEQUENCES

| | |
|---|---|
| 10K12A | DIVMTQSPSSLTVTAGEKVTMSCKSSQSLLNSGNQKNYLTWY QQKPGQPPKLLIYWASTRESGVPDRFTGSGSGTDFTLTISSV QAEDLAIYYCQNDYFYPLTFGAGTKLELK (SEQ ID NO: 94) |
| 10L9A | DIVMTQSPSSLTVTAGEKVTMSCRSSQSLLNSGNQRNYLTWY QQKPGHPPKLLIYWASTRESGVPDRFTGSGSGTDFTLTISGV QAEDLAVYYCQNGYSYPLTFGAGTKLEVK (SEQ ID NO: 95) |
| 10P2A | DIVMTQSPSSLTVTAGEKVTMSCKSSQSLLNSGNLRNYLTWY QQKPGQPPKLLIYWASTRESGVPDRFTGSGSGTDFTLTINSV QAEDLALYFCQDGYFYPFPFGSGTKLVIK (SEQ ID NO: 96) |
| 1B13A | DIVMTQSPSPLTVTAGEKATMSCKSSQSLLNSGNQRNYLTWY QQKPGQPPKLLIYWASTRESGVPDRFTGSGSGTDFSLTISSV QAEDLAVYYCQNDFIYPFTFGSGTKLEIK (SEQ ID NO: 97) |
| 1M5A | DIVMTQSPSSLTVTAGEKVTMSCKSSQSLLNSGNQKNYLTWY QQKPGQPPKLLIYWASTRESGVPDRFTGSGSGTDFTLTISSV QAEDLAVYYCQNNYFYPFTFGSGTKLEIK (SEQ ID NO: 98) |
| 2D22A | DIVMTQSPSSLTVTAGEKVTMSCKSSQSLLNSGNQRNYLAWY QQKPGQPPKLLIYWASTRESGVPDRFTGSGSGTDFTLTISSV QAEDLAVYYCQNDYSYPLTFGAGTKLELK (SEQ ID NO: 99) |
| 4N1A | DIVMTQSPSSLTVTAGEKVTMSCKSSQSLLNSGNQKNYLTWY QQKPGQPPKLLIYWASTRESGVPDRFTGSGSGTDFTLTISSV QAEDLTVYYCQNAYSYPLTFGAGTKLELK (SEQ ID NO: 100) |
| 5J22A | DIVMTQSPSSLTVTAGEKVTMSCKSSQSLLNSGNQKNYLTWY QQKPGQPPKLLIYWASTRESGVPDRFTGSGSGTDFTLTISSV QAEDLTVYYCQNAYSFPLTFGAGTKLELK (SEQ ID NO: 101) |
| 6C5A | DIVMTQSPSSLTVTAGEKVTMSCKSSQSLLNSGNQRNYLTWY QRKPGQPPKLLIYWASTRESGVPDRFTGSGSGTDFTLTISSV QAEDLTFYYCQNGYSYPLTFGAGTKLELK (SEQ ID NO: 102) |
| 6M11A | DIVMTQSPSSLTVTAGEKVTMSCKSSQSLLNSGNQKNYLTWY QQKPGQPPKLLLYWASTRESGVPDRFTGSGSGTDFTLTISSV QAEDLTVYYCQNAYSYPLTFGAGTKLELK (SEQ ID NO: 103) |
| 7A21A | DIVMTQSPSSLTVTAGEKVTMSCKSSQSLLNSGNQKNYLTWY QQKPGQPPKLLIYWASTRESGVPDRFTGSGSGTDFTLTISSV QAEDLAVYYCQNDYIYPLTFGAGTKLGLK (SEQ ID NO: 104) |
| 7B15A | DIVMTQSPSSLTVTAGEKVTMNCKSSQSLLNSGNQKNYLTWY QQKPGQPPKLLIYWASTRESGVPDRFTGSGSGTDFTLTISSV QAEDLTVYYCQNGYSYPLTFGAGTKLELK (SEQ ID NO: 105) |
| 7E20A | DIVMTQSPSSLTVTAGEKVTMSCKSSQSLFNTGNQKNYLTWY QQKPGQPPKLLIYWASTRESGVPDRFTGSGSGTDFTLTISSV QAEDLTVYYCQNGYSYPLTFGAGTKLELK (SEQ ID NO: 106) |

TABLE 8-continued

VL SEQUENCES

| | |
|---|---|
| 7G17A | DIVMTQSPSSLTVTPGEKVTMSCKSSQSLFNSGNQRNYLAWY QQKPGQPPKLLIYWASTRESGVPDRFTGSGSGTDFTLTISSV QAEDLAVYYCQNDYFYPLTFGAGTKLELK (SEQ ID NO: 107) |
| 9A13B | DIVMTQSPSSLTVTAGEKVTMSCKSSQSLLNSGNQKNYLTWY QQKPGQPPKLLIYWASTRESGVPDRFTGSGSGTDFTLTISSV QAEDLTVYYCQNGYSYPLTFGAGTKLELK (SEQ ID NO: 108) |
| 9B11A | DIVMTQSPSSLTVTAGEKVTMSCKSSQSLLNSGNQKNYLTWY QQKPGQPPKLLIYWASTRDSGVPDRFTGSGSGTDFTLTISSV QAEDLAVYYCQNNYYYPLTFGAGTNLELK (SEQ ID NO: 109) |
| 9C6A | DIVMTQSPSSLTVTAGEKVTLSCKSSQSLLNSGNQKNYLTWY QQKPRQPPKLLIYWASTRESGVPDRFTGSGSGTDFTLTISNV QAEDLTVYYCQNAYSYPLTFGAGTKLELK (SEQ ID NO: 110) |
| 9M7A | DIVMTQSPSSLTVTAGEKVTMSCKSSQSLLNSGNQKNYLTWY QQKPGQPPKLLIYWASTRESGVPDRFTGSGSGTDFTLTISSV QAEDLAVYYCQNNYIYPFTFGSGTKLEIK (SEQ ID NO: 111) |
| 9N14A | DIVMTQSPSSLTVTAGEKVTMSCKSSQSLLNSGNQKNYLTWY QQKPGQPPKLLIYWASTRESGVPDRFTGSGSGTDFTLTISSV QAEDLAVYYCQNDYIYPLTFGAGTKLGLK (SEQ ID NO: 112) |
| 10J10B | DIVMTQSPSSLTVTAGEKVTMTCKSSQILLNSGNQKNYLTWY QQKPGQPPKLLIYWASTRESGVPDRFTGSGSGTDFSLTISSV QAEDLAIYYCQNDYYYPFTFGSGTKLEIK (SEQ ID NO: 113) |
| 10P12A | DIVMTQSPSSLTVTAGERVTVGCKSRQSLFNSENQKNYLSWY QQKPGQPPKLLLYWTSTRESGVPERFTGSGSGTDFTLTISSV QAEDLAVYYCQNNYIYPFTFGSGTKLEIK (SEQ ID NO: 114) |
| 1H16A | DIVMTQSPSSLTVTAGERVTMSCKSSQSLLNSGNLKNYLTWY QQKPGQPPKLLIYWASTRESGVPDRFTGSGSGTDFTLTISTV QAEDLAVYYCQNDYFYPLTFGAGTKLELK (SEQ ID NO: 115) |
| 5K4B | DIVMTQSPSSLTVTAGEKVTMSCKSSQSLLNSGNQKNYLTWY QQKPGQPPKLLIYWASIRASGVPDRFTGSGSGTDFTLTISSV QAEDLALYYCLNDYSFPLTFGAGTKLELK (SEQ ID NO: 137) |
| 2F13A | DIVMTQSPSSLTVTAGEKVTMTCKSSQSLLNSGNQKNYLTWY QQKPGQPPKLLIYWASTRDSGVPDRFRGSGSGTDFTLTISSV QAEDLAVYYCLNDYSFPLTFGAGTKLELK (SEQ ID NO: 138) |

DNA fragments encoding the VH and VL domains of each clone shown in Tables 7 and 8 were synthesized. DNA fragments encoding a VH domain were each cloned into pcDNA3.4 in frame with human IgG1 constant region, and DNA fragments encoding a VL domain were each cloned into pcDNA3.4 in frame with human Ig Kappa constant region. Plasmids expressing the heavy chain and the light chain for each of the antibody clones shown in Tables 7 and 8 were then co-transfected into 293-6E cells grown in serum-free FreeStyle™ 293 Expression Medium. The cell culture supernatants were collected on day 6 and purified using Eshmuno® A chromatography. The eluted protein fractions were pooled and buffer exchanged to PBS, pH 7.2. Protein concentration for each eluted fraction was determined by A280, and the purity of each fraction was determined to be >95% via SDS-PAGE.

The interaction of 20 purified chimeric antibodies with CLDN18.2 was assessed by in-cell ELISAs and FACS using HEK293-CLDN18.2 cells. The in-cell ELISAs were performed as described above. The FACS assays were performed as follows: Serial dilutions for each antibody clone shown in Tables 7 and 8 were prepared and stained with HEK293-CLDN18.2 cells on ice for 30 min, with final antibody concentrations of 10 g/ml, 3 g/ml, 1 g/ml, 0.3 µg/ml, 0.1 µg/ml, 0.03 µg/ml, 0.01 µg/ml, and 0 µg/ml. The cells were washed with staining buffer (PBS+2% fetal bovine serum) to remove free antibodies, and further stained with AlexFluor 488-conjugated anti-human IgG antibody for 30 min on ice. Cells were washed, and analyzed by FACS. The EC50s of the chimeric antibodies are summarized in Table 9 below:

TABLE 9

| Chimeric Ab | In-cell ELISA EC50 (µg/ml) | FACS EC50 (ug/ml) |
|---|---|---|
| 10-K12-A | 0.05 | 0.075 |
| 1-B13-A | 0.059 | 0.036 |
| 1-M5-A | 0.042 | 0.044 |
| 2-D22-A | 0.065 | 0.051 |
| 4-N1-A | 0.059 | 0.029 |
| 5-J22-A | 0.065 | 0.023 |
| 6-C5-A | 0.058 | 0.044 |
| 6-M11-A | 0.098 | 0.026 |
| 7-A21-A | 0.23 | 0.134 |
| 7-B15-A | 0.066 | 0.032 |
| 7-E20-A | 0.198 | 0.050 |
| 7-G17-A | 0.098 | 0.033 |
| 9-A13-B | 0.15 | 0.068 |
| 9-B11-A | 0.069 | 0.045 |
| 9-C6-A | 0.491 | 0.032 |
| 9-M7-A | 0.154 | 0.095 |
| 9-N14-A | 0.218 | 0.075 |
| 10-J10-B | 0.062 | 0.141 |
| 10-P12-A | 0.106 | 0.018 |
| 1-H16-A | 0.08 | 0.101 |

Figure 2:
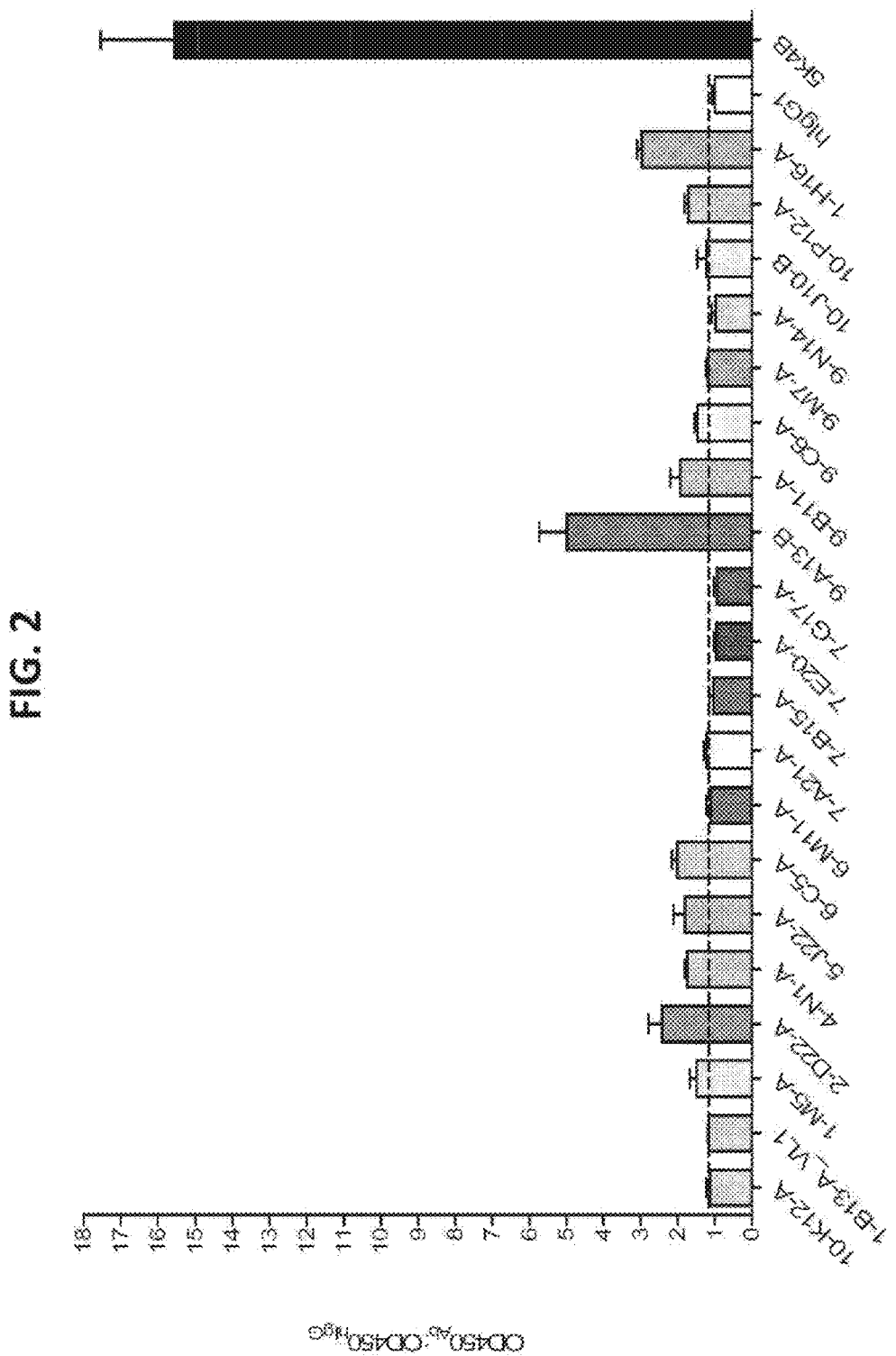
FIG. 2 shows the results of ELISAs performed to assess the interaction of purified chimeric anti-CLDN18.2 antibodies with HEK293-CLDN18.1.

A second set of in-cell ELISA assays were performed to assess the binding of the purified chimeric antibodies to CLDN18.1, a different splice variant of the CLDN protein. The assays were performed as described above using 1 µg/ml of each antibody clone and HEK293-CLDN18.1 cells. 1 µg/ml human IgG1 was used as a negative control. The supernatant of hybridoma 5K4B, which contains an antibody that binds to both CLDN18.1 and CLDN18.2 (see FIG. 1) was used as a positive control. As shown in FIG. 2, 2-D22-A, 9-A13-B and 1H16-A showed some degree of interaction with CLDN18.1, whereas the others only bound to CLDN18.2, but not CLDN18.1.

Example 2: CLDN18.2 Specific Antibody Binding to Gastric Cancer Cell Lines

Figure 3A:
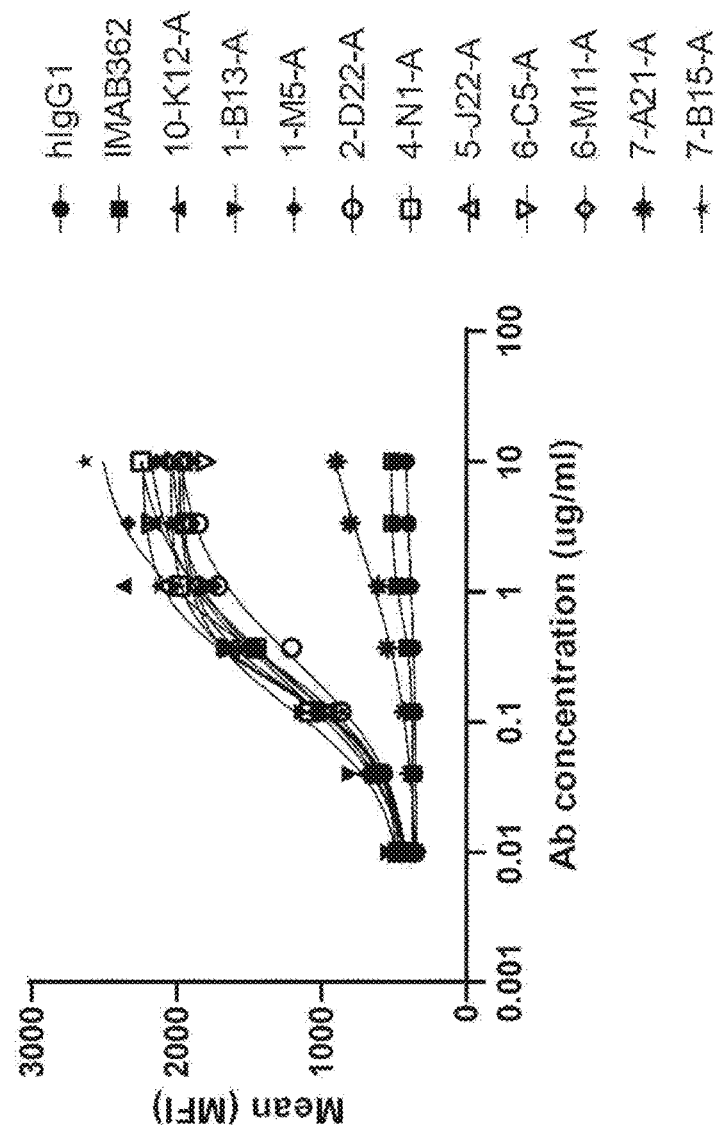
FIG. 3A provides the results of experiments that were performed to assess the binding of anti-CLDN antibodies 10-K12-A, 1-B13-A, 1-M5-A, 2-D22-A, 4-N1-A, 5-22-A, 6-C5-A, 6-M11-A, 7-A21-A, and 7-B15-A as compared to reference anti-CLDN18.2 antibody IMAB362 to CLDN18.2 expressed on the surface of KATO III human gastric carcinoma cells.
Figure 3B:
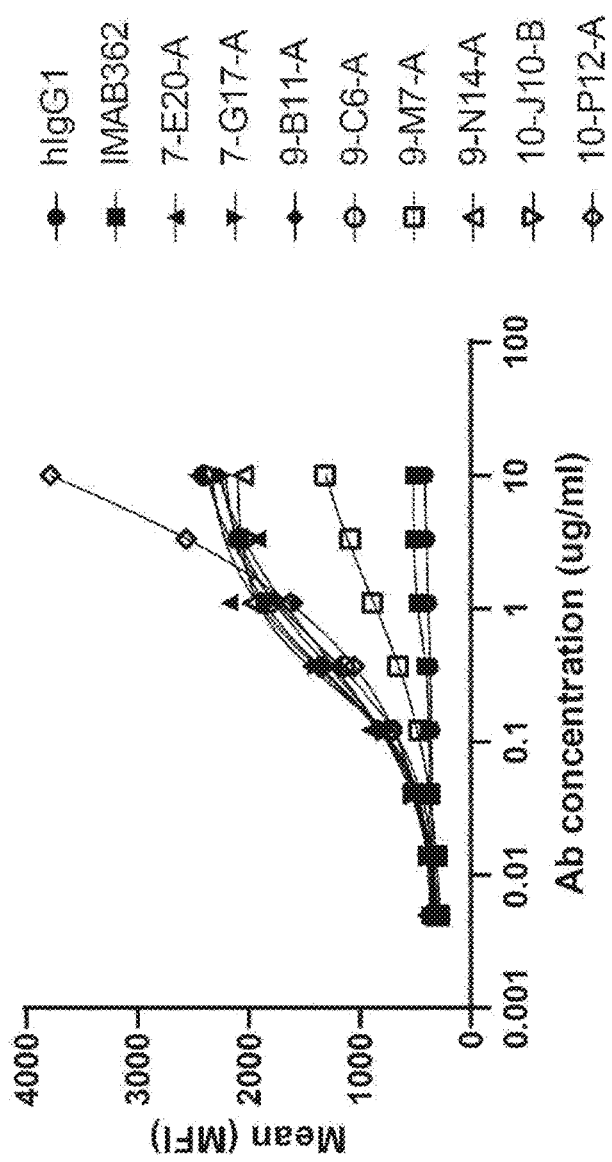
FIG. 3B provides the results of experiments that were performed to assess the binding of anti-CLDN antibodies 7-E20A, 7-G17-A, 9-B11-A, 9-C6-A, 9-M7-A, 9-N14-A, 10-J10-B, and 10-P12-A as compared to reference anti-CLDN18.2 antibody IMAB362 to CLDN18.2 expressed on the surface of KATO III human gastric carcinoma cells.

Human gastric carcinoma cell lines KATO-III (ATCC HTB-103) and NUGC-4 (JCRB0834) were found to display robust endogenous expression of CLDN 18. Cell Surface binding of purified chimeric antibodies described in Example ito constitutively expressed CLDN18.2 on KATO-III and NUGC-4 living cells was analyzed by FACS, and the binding EC50 value for each antibody was determined. The EC50s of 18 of the 20 antibodies described in Example 1, namely, 10-K12-A, 1-B13-A, 1-M5-A, 2-D22-A, 4-N1-A, 5-22-A, 6-C5-A, 6-M11-A, 7-A21-A, 7-B15-A, 7-E20-A, 7-G17-A, 9-B11-A, 9-C6-A, 9-M7-A, 9-N14-A, 10-110-B, and 10-P12-A have EC50 values lower than the EC50 value of the anti-CLDN18.2 reference antibody IMAB362. These 18 antibodies, also have higher maximum binding value than IMAB362, indicating that antibodies 10-K12-A, 1-B13-A, 1-M5-A, 2-D22-A, 4-N1-A, 5-22-A, 6-C5-A, 6-M11-A, 7-A21-A, 7-B15-A, 7-E20-A, 7-G17-A, 9-B11- A, 9-C6-A, 9-M7-A, 9-N14-A, 10-J10-B, 10-P12-A have higher affinity to CLDN18.2 than reference antibody IMAB362. See FIGS. 3A, 3B, and 3C.

Example 3: Assessing the Binding of Anti-CLDN18.2 Antibodies to IMAB362-Specific Peptides IMAB362 (also known as zolbetuximab or claudiximab) is a chimeric IgG1 antibody that is specific for CLDN18.2. Two small cyclized peptides (i.e., peptide 2C and peptide 3C) were previously developed by phage display and then optimized via peptide microarray technology to bind to IMAB362 for detection of serum IMAB362 by ELISA in clinical tissue samples (see Daneschdar et al. (2014) *JPT Peptide Technologies*, Volmerstrasse 5, 12489). Daneschdar and colleagues showed via ELISA that IMAB362 bound to peptide 2C and to peptide 3C with sub-nanomolar affinity. The antibodies described in Example 1 and reference antibody IMAB362 were assessed for their abilities to bind peptide 2C and peptide 3Cby ELISA. Antibodies 10-K12A, 1-B13-A, 6-C5-A, 7-G17-A, 9-B11-A, 9-N14-A, 10-110-B, 7-A21-A and 9-M7-A were chosen for the representative affinity range from high to low. Only reference antibody IMAB362 was found to bind peptides 2C and 3C, whereas antibodies 10-K12A, 1-B13-A, 6-C5-A, 7-A21-A, 7-G17-A, 9-B11-A, 9-M7-A, 9-N14-A and 10-10-B did not bind to either peptide. Such results indicate that antibodies 10-K12A, 1-B13-A, 6-C5-A, 7-A21-A, 7-G17-A, 9-B11-A, 9-M7-A, 9-N14-A and 10-10-B. bind to an epitope of CLDN18.2 that is distinct from the epitope bound by IMAB362.

A further competition experiment was performed using peptides 2C and 3C to assess whether the peptides interfere with the abilities of antibodies 10-K12-A, 1-B13-A, 1-M5-A, 2-D22-A, 4-N1-A, 5-22-A, 6-C5-A, 6-M11-A, 7-A21-A, 7-B15-A, 7-E20-A, 7-G17-A, 9-B11-A, 9-C6-A, 9-M7-A, 9-N14-A, 10-110-B, 10-P12-Ato bind to the surface of HEK293-CLDN18.2 cells (which were described in Example 1). As shown in FIG. 5, both peptide 2C and peptide 3C competed efficiently with reference antibody (IMAB362 in the figure below) for binding to CLDN18.2 expressed on the surface of HEK293 cells. Neither peptide affected the abilities of antibodies 10-K12-A, 1-B13-A, 1-M5-A, 2-D22-A, 4-N1-A, 5-22-A, 6-C5-A, 6-M11-A, 7-A21-A, 7-B15-A, 7-E20-A, 7-G17-A, 9-B11-A, 9-C6-A, 9-M7-A, 9-N14-A, 10-110-B, 10-P12-Ato bind HEK293-CLDN18.2 cells.

Example 4: In Vivo Efficacy Study of Selected Antibodies in Mouse PDX Models

Three antibody clones, 1-B13-A, 7-G17-A and 9-M7-A, and reference antibody IMAB362 were reformatted to mouse IgG2a and their in vivo antitumor efficacies were test using patient-derived gastric tumor xenografts (i.e., patient derived-xenografts or PDX). 1-B13-A, 7-G17-A and 9-M7-A were selected by binding affinity to the gastric cancer cell lines from high to low. One hundred and forty BALB/c nude mice (female, 6-10 weeks of age, obtained from CrownBio: www(dot)crownbio(dot)com/oncology/in-vivo-services/patient-derived-xenograft-pdx-tumor-models) were implanted with patient-derived gastric tumor (about 2-3 mm$^3$). When tumor sizes reached 50-100 mm$^3$, the mice were sorted randomly into 6 groups (8 mice/group) and dosed according to the dosing schedule listed in Table 10 below.

TABLE 10

Dosing Schedule for Efficacy Study in Gastric PDX Model

| Group | Number of Animals | Antibody | Ab Dose (μg/mouse) | Dosing Route | Dosing Frequency | Duration of Ab Treatment |
|---|---|---|---|---|---|---|
| 1 | 8 | Vehicle control (PBS) | 0 | IV* | BIW** for 4 weeks | 4 weeks |
| 2 | 8 | IMAB362 | 800 | IV | BIW for 4 weeks | 4 weeks |
| 3 | 8 | 1-B13-A | 800 | IV | BIW for 4 weeks | 4 weeks |
| 4 | 8 | 7-G17-A | 800 | IV | BIW for 4 weeks | 4 weeks |
| 5 | 8 | 9-M7-A | 800 | IV | BIW for 4 weeks | 4 weeks |
| 6 | 8 | 7-G17-A | 200 | IV | BIW for 4 weeks | 4 weeks |

*IV = intravenous
**BIW = biweekly (twice a week).

Figure 6A:
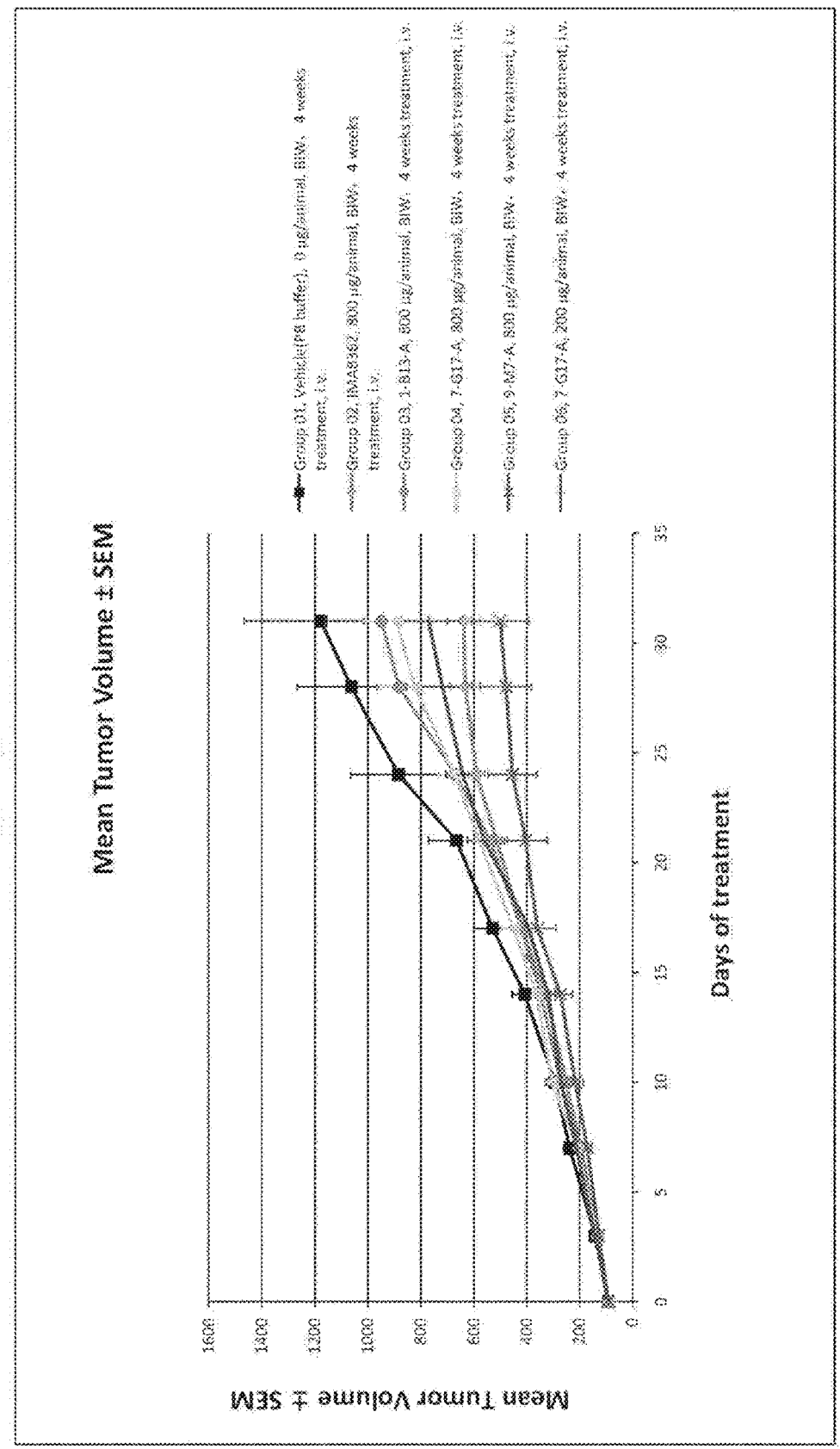
FIG. 6A and FIG. 6B provide the results of patient-derived gastric tumor xenograft (PDX) experiments in mice that were performed to assess the in vivo efficacy of antibodies 1-B13-A, 7-G17-A, 9-M7-A, and reference antibody IMAB362 in inhibiting tumor growth.
Figure 6B:
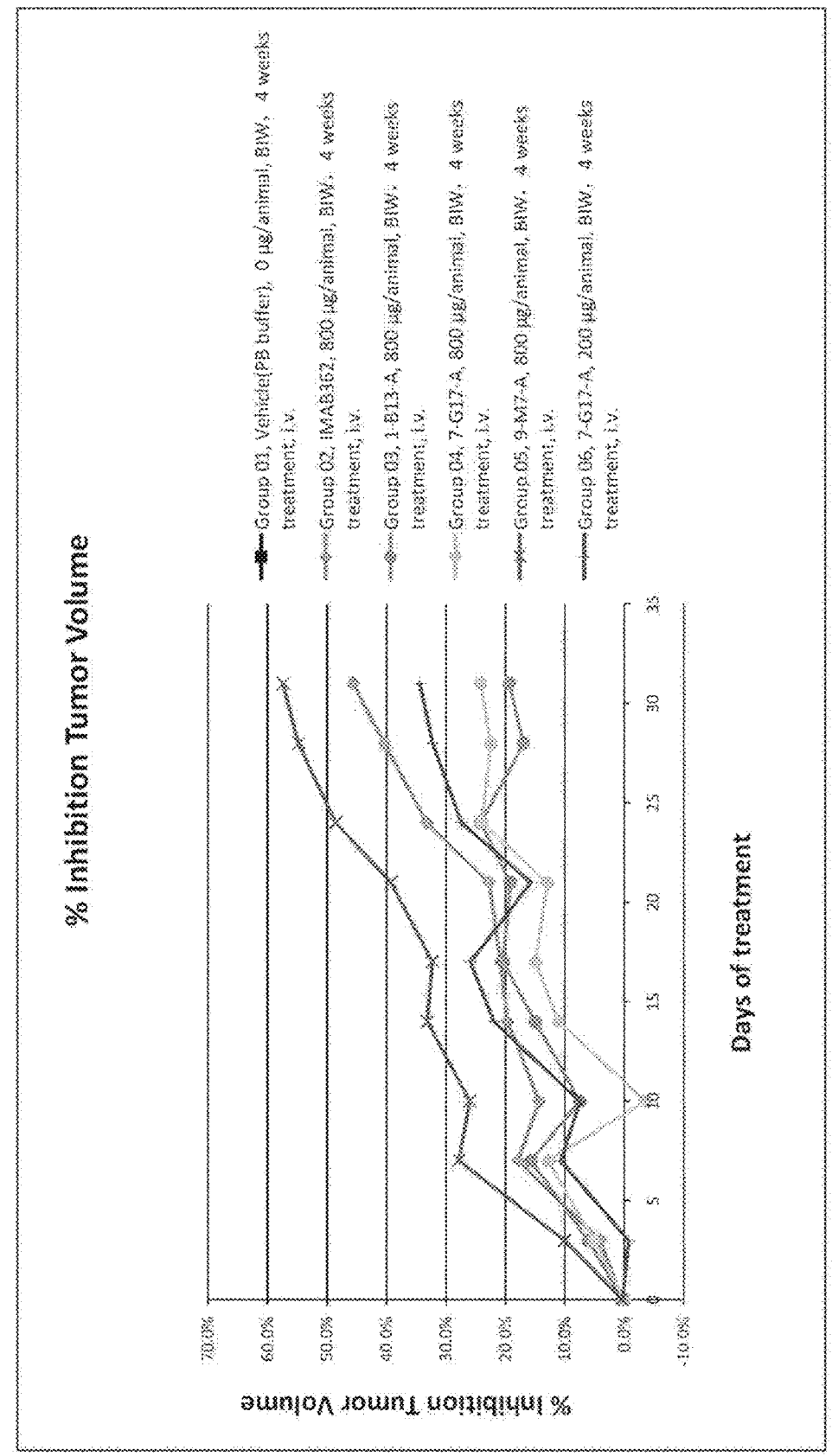

As shown in FIG. 6A, the mice treated with 9-M7-A demonstrated significantly reduced tumor burden relative to mice treated with 1-B13-A, 7-G17-A, or reference antibody IMAB362. Correspondingly, FIG. 6B shows that treatment with 9-M7-A inhibited tumor growth in mice by 55%, whereas reference antibody IMAB362 only inhibited tumor growth by 40% in the same study.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

The invention claimed is:

1. The anti-CLDN18.2 antibody or antigen binding fragment thereof, comprising:
   (i) a VH domain comprising (a) a CDR-H1 comprising GFTFSDYGMF (SEQ ID NO: 1), (b) a CDR-H2 comprising YISSGSSNIYYADTVKG (SEQ ID NO: 12), and (c) a CDR-H3 comprising IARGNAMDY (SEQ ID NO: 31); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYFYPLT (SEQ ID NO: 59);
   (ii) a VH domain comprising (a) a CDR-H1 comprising GFTFSDYGMH (SEQ ID NO: 2), (b) a CDR-H2 comprising YINSGSSTIYYADTVKG (SEQ ID NO: 13), and (c) a CDR-H3 comprising FARGNVLDY (SEQ ID NO: 32); and/or a VL domain comprising (d) a CDR-L1 comprising RSSQSLLNSGNQRNYLT (SEQ ID NO: 45), (e) a CDR-L2 comprising WASTRES (SEQ ID NO: 55), and (f) a CDR-L3 comprising QNGYSYPLT (SEQ ID NO: 60);
   (iii) a VH domain comprising (a) a CDR-H1 comprising GYSFTGYNIH (SEQ ID NO: 3), (b) a CDR-H2 comprising YIDPNNGVTYSNQKFKG (SEQ ID NO: 14), and (c) a CDR-H3 comprising PYYGNSFDY (SEQ ID NO: 33); and/or a VL domain comprising (d) a CDR-L1 comprising KSSQSLLNSGNLRNYLT (SEQ ID NO: 46), (e) a CDR-L2 comprising WASTRES (SEQ ID NO: 55), and (f) a CDR-L3 comprising QDGYFYPFP (SEQ ID NO: 61);
   (iv) a VH domain comprising (a) a CDR-H1 comprising GYTFTVWSMS (SEQ ID NO: 4), (b) a CDR-H2 comprising EIYPKSGNTHYNEKFKG (SEQ ID NO: 15), and (c) a CDR-H3 comprising AYYGNSFAY (SEQ ID NO: 34); and/or a VL domain comprising (d) a CDR-L1 comprising KSSQSLLNSGNQRNYLT (SEQ ID NO: 47), (e) a CDR-L2 comprising WASTRES (SEQ ID NO: 55), and (f) a CDR-L3 comprising QNDFIYPFT (SEQ ID NO: 62);
   (v) a VH domain comprising (a) a CDR-H1 comprising GFTFSNNAMS (SEQ ID NO: 5), (b) a CDR-H2 comprising TIIGGTYTYYPDSVKG (SEQ ID NO: 16), and (c) a CDR-H3 comprising QVYGNSFAY (SEQ ID NO: 35); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNNYFYPFT (SEQ ID NO: 63);
   (vi) a VH domain comprising (a) a CDR-H1 comprising GFTFSDYGMH (SEQ ID NO: 2), (b) a CDR-H2 comprising YISSGSSTIYYADTMKG (SEQ ID NO: 18), and (c) a CDR-H3 comprising FVRGNSMDY (SEQ ID NO: 36); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65);

(vii) a VH domain comprising (a) a CDR-H1 comprising GFTFSDYGMH (SEQ ID NO: 2), (b) a CDR-H2 comprising HISSGSNIIHYADTLKG (SEQ ID NO: 19), and (c) a CDR-H3 comprising FARGNTMDY (SEQ ID NO: 37); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSFPLT (SEQ ID NO: 66);

(viii) a VH domain comprising (a) a CDR-H1 comprising GFTFSDYGMH (SEQ ID NO: 2), (b) a CDR-H2 comprising YISSGSSTIYYADTMKG (SEQ ID NO: 18), and (c) a CDR-H3 comprising FARGNTMDY (SEQ ID NO: 37); and/or a VL domain comprising (d) a CDR-L1 comprising KSSQSLLNSGNQRNYLT (SEQ ID NO: 47), (e) a CDR-L2 comprising WASTRES (SEQ ID NO: 55), and (f) a CDR-L3 comprising QNGYSYPLT (SEQ ID NO: 60);

(ix) a VH domain comprising (a) a CDR-H1 comprising GFTFSDYGMH (SEQ ID NO: 2), (b) a CDR-H2 comprising YISSGSNTFYYTDTVKG (SEQ ID NO: 20), and (c) a CDR-H3 comprising FTRGNALDY (SEQ ID NO: 38); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65);

(x) a VH domain comprising (a) a CDR-H1 comprising GFTFSDYGMY (SEQ ID NO: 6), (b) a CDR-H2 comprising YISSGSNTIYYADTVKG (SEQ ID NO: 21), and (c) a CDR-H3 comprising IARGNAMDY (SEQ ID NO: 31); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYIYPLT (SEQ ID NO: 67);

(xi) a VH domain comprising (a) a CDR-H1 comprising GFTFSDYGMH (SEQ ID NO: 2), (b) a CDR-H2 comprising HISSGSSTIYYADTMKG (SEQ ID NO: 22), and (c) a CDR-H3 comprising FVRGNALDY (SEQ ID NO: 39); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNGYSYPLT (SEQ ID NO: 60);

(xii) a VH domain comprising (a) a CDR-H1 comprising GFTFSDYGMH (SEQ ID NO: 2), (b) a CDR-H2 comprising YISSGSSTIHYVDTMKG (SEQ ID NO: 23), and (c) a CDR-H3 comprising FARGNTLDY (SEQ ID NO: 40); and/or a VL domain comprising (d) a CDR-L1 comprising KSSQSLFNTGNQKNYLT (SEQ ID NO: 49), (e) a CDR-L2 comprising WASTRES (SEQ ID NO: 55), and (f) a CDR-L3 comprising NGYSYPLT (SEQ ID NO: 60);

(xiii) a VH domain comprising (a) a CDR-H1 comprising GFTFSDYGMY (SEQ ID NO: 6), (b) a CDR-H2 comprising YISSGSSTIYYADTVKG (SEQ ID NO: 24), and (c) a CDR-H3 comprising IARGNAMDY (SEQ ID NO: 31); and/or a VL domain comprising (d) a CDR-L1 comprising KSSQSLFNSGNQRNYLA (SEQ ID NO: 50), (e) a CDR-L2 comprising WASTRES (SEQ ID NO: 55), and (f) a CDR-L3 comprising QNDYFYPLT (SEQ ID NO: 59);

(xiv) a VH domain comprising (a) a CDR-H1 comprising GFTFSDYGMH (SEQ ID NO: 2), (b) a CDR-H2 comprising YISSGSSPIYYADTVKG (SEQ ID NO: 25), and (c) a CDR-H3 comprising FARGNAMDY (SEQ ID NO: 41); and/or a VL domain comprising (d) a CDR-L1 comprising KSSQSLLNSGNQKNYLT (SEQ ID NO: 44), (e) a CDR-L2 comprising WASTRDS (SEQ ID NO: 56), and (f) a CDR-L3 comprising QNNYYYPLT (SEQ ID NO: 68);

(xv) a VH domain comprising (a) a CDR-H1 comprising GFTFSDYGMH (SEQ ID NO: 2), (b) a CDR-H2 comprising YISSGSSTIYYADTMKG (SEQ ID NO: 18), and (c) a CDR-H3 comprising FVRGNSMDY (SEQ ID NO: 36); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNAYSYPLT (SEQ ID NO: 65);

(xvi) a VH domain comprising (a) a CDR-H1 comprising GFTFSNYAMS (SEQ ID NO: 8), (b) a CDR-H2 comprising TIIIGGTYTYYPDSVKG (SEQ ID NO: 16), and (c) a CDR-H3 comprising QVYGNSFAY (SEQ ID NO: 35); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNNYIYPFT (SEQ ID NO: 69);

(xvii) a VH domain comprising (a) a CDR-H1 comprising GFTFSDYGMY (SEQ ID NO: 6), (b) a CDR-H2 comprising YISSGSNNIYYADTVKG (SEQ ID NO: 26), and (c) a CDR-H3 comprising IARGNAMDY (SEQ ID NO: 31); and/or a VL domain comprising (d) a CDR-L1 comprising KSSQSLLNSGNQKNYLT (SEQ ID NO: 44), (e) a CDR-L2 comprising WASTRES (SEQ ID NO: 55), and (f) a CDR-L3 comprising QNDYIYPLT (SEQ ID NO: 67);

(xviii) a VH domain comprising (a) a CDR-H1 comprising GYTFTSWSIS (SEQ ID NO: 9), (b) a CDR-H2 comprising EIYPRSDNIHYNEKFKG (SEQ ID NO: 27), and (c) a CDR-H3 comprising AYYGNSFAY (SEQ ID NO: 34); and/or a VL domain comprising (d) a CDR-L1 comprising KSSQILLNSGNQKNYLT (SEQ ID NO: 51), (e) a CDR-L2 comprising WASTRES (SEQ ID NO: 55), and (f) a CDR-L3 comprising QNDYYYPFT (SEQ ID NO: 70); or (xix) a VH domain comprising (a) a CDR-H1 comprising GYSFTGYNMN (SEQ ID NO: 10), (b) a CDR-H2 comprising NINPYYSNTNYNQRFKG (SEQ ID NO: 28), and (c) a CDR-H3 comprising CDRGNSFDY (SEQ ID NO: 42); and/or a VL domain comprising (d) a CDR-L1 comprising KSRQSLFNSENQKNYLS (SEQ ID NO: 52), (e) a CDR-L2 comprising WTSTRES (SEQ ID NO: 57), and (f) a CDR-L3 comprising QNNYIYPFT (SEQ ID NO: 69).

2. The anti-CLDN18.2 antibody or antigen binding fragment thereof of claim 1, comprising:
(i) a VH domain comprising SEQ ID NO: 72; and/or a VL domain comprising SEQ ID NO: 94;
(ii) a VH domain comprising SEQ ID NO: 73; and/or a VL domain comprising SEQ ID NO: 95;
(iii) a VH domain comprising SEQ ID NO: 74; and/or a VL domain comprising SEQ ID NO: 96;
(iv) a VH domain comprising SEQ ID NO: 75; and/or a VL domain comprising SEQ ID NO: 97;
(v) a VH domain comprising SEQ ID NO: 76; and/or a VL domain comprising SEQ ID NO: 98;
(vi) a VH domain comprising SEQ ID NO: 78; and/or a VL domain comprising SEQ ID NO: 100;
(vii) a VH domain comprising SEQ ID NO: 79; and/or a VL domain comprising SEQ ID NO: 101;

(viii) a VH domain comprising SEQ ID NO: 80; and/or a VL domain comprising SEQ ID NO: 102;
(ix) a VH domain comprising SEQ ID NO: 81; and/or a VL domain comprising SEQ ID NO: 103;
(x) a VH domain comprising SEQ ID NO: 82; and/or a VL domain comprising SEQ ID NO: 104;
(xi) a VH domain comprising SEQ ID NO: 83; and/or a VL domain comprising SEQ ID NO: 105;
(xii) a VH domain comprising SEQ ID NO: 84; and/or a VL domain comprising SEQ ID NO: 106;
(xiii) a VH domain comprising SEQ ID NO: 85; and/or a VL domain comprising SEQ ID NO: 107;
(xiv) a VH domain comprising SEQ ID NO: 87; and/or a VL domain comprising SEQ ID NO: 109;
(xv) a VH domain comprising SEQ ID NO: 88; and/or a VL domain comprising SEQ ID NO: 110;
(xvi) a VH domain comprising SEQ ID NO: 89; and/or a VL domain comprising SEQ ID NO: 111;
(xvii) a VH domain comprising SEQ ID NO: 90; and/or a VL domain comprising SEQ ID NO: 112;
(xviii) a VH domain comprising SEQ ID NO: 91; and/or a VL domain comprising SEQ ID NO: 113; or
(xix) a VH domain comprising SEQ ID NO: 92; and/or a VL domain comprising SEQ ID NO: 114.

3. The anti-CLDN18.2 antibody or antigen binding fragment thereof of claim 1, wherein the antibody comprises an Fc sequence of a human IgG1, a human IgG2, a human IgG3 or a human IgG4.

4. The anti-CLDN18.2 antibody or antigen binding fragment thereof of claim 1, wherein the antibody is a chimeric, humanized, or human antibody.

5. The antigen binding fragment of the anti-CLDN18.2 antibody of claim 1, wherein the antigen binding fragment is selected from the group consisting of: a Fab, a Fab', a F(ab)'2, a single-chain Fv (scFv), an Fv fragment, a diabody, and a linear antibody.

6. The anti-CLDN18.2 antibody of claim 1, wherein the antibody is a multispecific antibody.

7. The anti-CLDN18.2 antibody of claim 1, wherein the CLDN18.2 is human CLDN18.2.

8. The anti-CLDN18.2 antibody or antigen binding fragment thereof of claim 1 conjugated to:
(a) a therapeutic agent, or
(b) a label, wherein the label is selected from the group consisting of a radioisotope, a fluorescent dye, and an enzyme.

9. Isolated nucleic acid molecule(s) that encode the anti-CLDN18.2 antibody or antigen binding fragment thereof of claim 1.

10. An expression vector encoding the nucleic acid molecule(s) of claim 9.

11. A host cell comprising the nucleic acid molecule(s) of claim 9.

12. A method of producing an anti-CLDN18.2 antibody, comprising culturing the host cell of claim 11 and recovering the antibody from the cell culture.

13. A composition comprising the anti-CLDN18.2 antibody or antigen binding fragment thereof of claim 1 and a pharmaceutically acceptable carrier.

14. A method of detecting a CLDN18.2 protein in sample from a patient by contacting the anti-CLDN18.2 antibody or antigen binding fragment thereof of claim 1 to the sample and detecting the anti-CLDN18.2 antibody bound to the CLDN18.2 protein.

15. A method of treating cancer in a subject, comprising administering an effective amount of the composition of claim 13 to the subject.

16. The method of claim 15, wherein the subject is further administered a therapeutic agent selected from the group consisting of: an anti-neoplastic agent, a chemotherapeutic agent, a growth inhibitory agent and a cytotoxic agent.

* * * * *

SEQUENCE LISTING

```
<160> NUMBER OF SEQ ID NOS: 141

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Asp Tyr Gly Met Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Gly Phe Thr Phe Ser Asp Tyr Gly Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Tyr Ser Phe Thr Gly Tyr Asn Ile His
1               5                   10

<210> SEQ ID NO 4
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 4

Gly Tyr Thr Phe Thr Val Trp Ser Met Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Phe Thr Phe Ser Asn Asn Ala Met Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gly Phe Thr Phe Ser Asp Tyr Gly Met Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Phe Ser Phe Ser Asp Tyr Gly Met His
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Gly Phe Thr Phe Ser Asn Tyr Ala Met Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Gly Tyr Thr Phe Thr Ser Trp Ser Ile Ser
1               5                   10

<210> SEQ ID NO 10
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 10

Gly Tyr Ser Phe Thr Gly Tyr Asn Met Asn
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Phe or Tyr
<220> FEATURE:
<221> NAME/KEY: VARIANT
<222> LOCATION: 3
<223> OTHER INFORMATION: Xaa = Thr or Ser
<220> FEATURE:
<221> NAME/KEY: VARIANT
<222> LOCATION: 5
<223> OTHER INFORMATION: Xaa = Thr or Ser
<220> FEATURE:
<221> NAME/KEY: VARIANT
<222> LOCATION: 6
<223> OTHER INFORMATION: Xaa = Asp, Gly, Val, Asn, or Ser
<220> FEATURE:
<221> NAME/KEY: VARIANT
<222> LOCATION: 7
<223> OTHER INFORMATION: Xaa = Tyr, Trp, or Asn
<220> FEATURE:
<221> NAME/KEY: VARIANT
<222> LOCATION: 8
<223> OTHER INFORMATION: Xaa = Gly, Asn, Ser or Ala
<220> FEATURE:
<221> NAME/KEY: VARIANT
<222> LOCATION: 9
<223> OTHER INFORMATION: Xaa = Met or Ile
<220> FEATURE:
<221> NAME/KEY: VARIANT
<222> LOCATION: 10
<223> OTHER INFORMATION: Xaa = Phe, His, Ser, Tyr, or Asn

<400> SEQUENCE: 11

Gly Xaa Xaa Phe Xaa Xaa Xaa Xaa Xaa Xaa
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Tyr Ile Ser Ser Gly Ser Ser Asn Ile Tyr Tyr Ala Asp Thr Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13
```

Tyr Ile Asn Ser Gly Ser Ser Thr Ile Tyr Tyr Ala Asp Thr Val Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Tyr Ile Asp Pro Asn Asn Gly Val Thr Tyr Ser Asn Gln Lys Phe Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Glu Ile Tyr Pro Lys Ser Gly Asn Thr His Tyr Asn Glu Lys Phe Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Thr Ile Ile Ile Gly Gly Thr Tyr Thr Tyr Tyr Pro Asp Ser Val Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Tyr Ile Ser Ser Gly Ser Ser Ser Ile Tyr Tyr Ala Asp Thr Val Lys
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Tyr Ile Ser Ser Gly Ser Ser Thr Ile Tyr Tyr Ala Asp Thr Met Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

His Ile Ser Ser Gly Ser Asn Ile Ile His Tyr Ala Asp Thr Leu Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Tyr Ile Ser Ser Gly Ser Asn Thr Phe Tyr Tyr Thr Asp Thr Val Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Tyr Ile Ser Ser Gly Ser Asn Thr Ile Tyr Tyr Ala Asp Thr Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

His Ile Ser Ser Gly Ser Ser Thr Ile Tyr Tyr Ala Asp Thr Met Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Synthetic Construct

<400> SEQUENCE: 23

Tyr Ile Ser Ser Gly Ser Ser Thr Ile His Tyr Val Asp Thr Met Lys
1               5                   10                  15

Gly

<210> SEQ ID NO 24
<211> LENGTH: 17

<212> TYPE: PRT
<213> ORGANISM: Artificial Sequence
<220> FEATURE:
<223> OTHER INFORMATION: Synthetic Construct

<400> SEQUENCE: 24

Tyr Ile Ser Ser Gly Ser Ser Thr Ile Tyr Tyr Ala Asp Thr Val Lys
1               5                   10                  15
Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Tyr Ile Ser Ser Gly Ser Ser Pro Ile Tyr Tyr Ala Asp Thr Val Lys
1               5                   10                  15
Gly

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Tyr Ile Ser Ser Gly Ser Asn Asn Ile Tyr Tyr Ala Asp Thr Val Lys
1               5                   10                  15
Gly

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Glu Ile Tyr Pro Arg Ser Asp Asn Ile His Tyr Asn Glu Lys Phe Lys
1               5                   10                  15
Gly

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Asn Ile Asn Pro Tyr Tyr Ser Asn Thr Asn Tyr Asn Gln Arg Phe Lys
1               5                   10                  15
Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Phe Ile Ser Ser Gly Ser Ser Thr Ile Tyr Cys Ala Asp Thr Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Tyr, Glu, Thr, His, Asn, or Phe
<220> FEATURE:
<221> NAME/KEY: VARIANT
<222> LOCATION: 3
<223> OTHER INFORMATION: Xaa = Ser, Asn, Asp, Tyr, or Ile
<220> FEATURE:
<221> NAME/KEY: VARIANT
<222> LOCATION: 4
<223> OTHER INFORMATION: Xaa = Ser, Pro, or Ile
<220> FEATURE:
<221> NAME/KEY: VARIANT
<222> LOCATION: 5
<223> OTHER INFORMATION: Xaa = Gly, Asn, Lys, Arg, or Tyr
<220> FEATURE:
<221> NAME/KEY: VARIANT
<222> LOCATION: 6
<223> OTHER INFORMATION: Xaa = Ser, Asn, Gly, or Tyr
<220> FEATURE:
<221> NAME/KEY: VARIANT
<222> LOCATION: 7
<223> OTHER INFORMATION: Xaa = Ser, Gly, Thr, Asn, or Asp
<220> FEATURE:
<221> NAME/KEY: VARIANT
<222> LOCATION: 8
<223> OTHER INFORMATION: Xaa = Asn, Thr, Val, Tyr, Ser, Ile, or Pro
<220> FEATURE:
<221> NAME/KEY: VARIANT
<222> LOCATION: 9
<223> OTHER INFORMATION: Xaa = Ile, Thr, or Phe
<220> FEATURE:
<221> NAME/KEY: VARIANT
<222> LOCATION: 10
<223> OTHER INFORMATION: Xaa = Tyr, His, or Asn
<220> FEATURE:
<221> NAME/KEY: VARIANT
<222> LOCATION: 11
<223> OTHER INFORMATION: Xaa = Tyr, Ser, or Cys
<220> FEATURE:
<221> NAME/KEY: VARIANT
<222> LOCATION: 12
<223> OTHER INFORMATION: Xaa = Ala, Asn, Pro, Thr, or Val
<220> FEATURE:
<221> NAME/KEY: VARIANT
<222> LOCATION: 13
<223> OTHER INFORMATION: Xaa = Asp, Gln, or Glu
<220> FEATURE:
<221> NAME/KEY: VARIANT
<222> LOCATION: 14
<223> OTHER INFORMATION: Xaa = Thr, Lys, Ser, or Arg
<220> FEATURE:
<221> NAME/KEY: VARIANT
<222> LOCATION: 15
<223> OTHER INFORMATION: Xaa = Val, Phe, Met, or Leu

<400> SEQUENCE: 30

Xaa Ile Xaa Xaa Xaa Xaa Xaa Xaa Xaa Xaa Xaa Xaa Xaa Xaa Xaa Lys
1               5                   10                  15

Gly

```
<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Ile Ala Arg Gly Asn Ala Met Asp Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Phe Ala Arg Gly Asn Val Leu Asp Tyr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Pro Tyr Tyr Gly Asn Ser Phe Asp Tyr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Ala Tyr Tyr Gly Asn Ser Phe Ala Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Gln Val Tyr Gly Asn Ser Phe Ala Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Phe Val Arg Gly Asn Ser Met Asp Tyr
1               5
```

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Phe Ala Arg Gly Asn Thr Met Asp Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Phe Thr Arg Gly Asn Ala Leu Asp Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Phe Val Arg Gly Asn Ala Leu Asp Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Phe Ala Arg Gly Asn Thr Leu Asp Tyr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Phe Ala Arg Gly Asn Ala Met Asp Tyr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

His Val Arg Gly Asn Ser Phe Asp Tyr
1               5

<210> SEQ ID NO 43

```
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ile, Phe, Pro, Ala, Gln, or His
<220> FEATURE:
<221> NAME/KEY: VARIANT
<222> LOCATION: 2
<223> OTHER INFORMATION: Xaa = Ala, Tyr, Val, or Thr
<220> FEATURE:
<221> NAME/KEY: VARIANT
<222> LOCATION: 3
<223> OTHER INFORMATION: Xaa = Arg or Tyr
<220> FEATURE:
<221> NAME/KEY: VARIANT
<222> LOCATION: 6
<223> OTHER INFORMATION: Xaa = Ala, Val, Ser, or Thr
<220> FEATURE:
<221> NAME/KEY: VARIANT
<222> LOCATION: 7
<223> OTHER INFORMATION: Xaa = Met, Leu, or Phe
<220> FEATURE:
<221> NAME/KEY: VARIANT
<222> LOCATION: 8
<223> OTHER INFORMATION: Xaa = Asp or Ala

<400> SEQUENCE: 43

Xaa Xaa Xaa Gly Asn Xaa Xaa Xaa Tyr
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Lys Ser Ser Gln Ser Leu Leu Asn Ser Gly Asn Gln Lys Asn Tyr Leu
1               5                   10                  15

Thr

<210> SEQ ID NO 45
<211> LENGTH: 17
<212> TYPE: PRT
<213> ORGANISM: Artificial Sequence
<220> FEATURE:
<223> OTHER INFORMATION: Synthetic Construct

<400> SEQUENCE: 45

Arg Ser Ser Gln Ser Leu Leu Asn Ser Gly Asn Gln Arg Asn Tyr Leu
1               5                   10                  15

Thr

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Lys Ser Ser Gln Ser Leu Leu Asn Ser Gly Asn Leu Arg Asn Tyr Leu
1               5                   10                  15

Thr
```

<210> SEQ ID NO 47
<211> LENGTH: 17
<212> TYPE: PRT
<213> ORGANISM: Artificial Sequence
<220> FEATURE:
<223> OTHER INFORMATION: Synthetic Construct

<400> SEQUENCE: 47

Lys Ser Ser Gln Ser Leu Leu Asn Ser Gly Asn Gln Arg Asn Tyr Leu
1               5                   10                  15

Thr

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

Lys Ser Ser Gln Ser Leu Leu Asn Ser Gly Asn Gln Arg Asn Tyr Leu
1               5                   10                  15

Ala

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Lys Ser Ser Gln Ser Leu Phe Asn Thr Gly Asn Gln Lys Asn Tyr Leu
1               5                   10                  15

Thr

<210> SEQ ID NO 50
<211> LENGTH: 17
<212> TYPE: PRT
<213> ORGANISM: Artificial Sequence
<220> FEATURE:
<223> OTHER INFORMATION: Synthetic Construct

<400> SEQUENCE: 50

Lys Ser Ser Gln Ser Leu Phe Asn Ser Gly Asn Gln Arg Asn Tyr Leu
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

Lys Ser Ser Gln Ile Leu Leu Asn Ser Gly Asn Gln Lys Asn Tyr Leu
1               5                   10                  15

Thr

<210> SEQ ID NO 52
<211> LENGTH: 17

-continued

```
<212> TYPE: PRT
<213> ORGANISM: Artificial Sequence
<220> FEATURE:
<223> OTHER INFORMATION: Synthetic Construct

<400> SEQUENCE: 52

Lys Ser Arg Gln Ser Leu Phe Asn Ser Glu Asn Gln Lys Asn Tyr Leu
1               5                   10                  15

Ser

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Lys Ser Ser Gln Ser Leu Leu Asn Ser Gly Asn Leu Lys Asn Tyr Leu
1               5                   10                  15

Thr

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Lys or Arg
<220> FEATURE:
<221> NAME/KEY: VARIANT
<222> LOCATION: 3
<223> OTHER INFORMATION: Xaa = Ser or Arg
<220> FEATURE:
<221> NAME/KEY: VARIANT
<222> LOCATION: 5
<223> OTHER INFORMATION: Xaa = Ser or Ile
<220> FEATURE:
<221> NAME/KEY: VARIANT
<222> LOCATION: 7
<223> OTHER INFORMATION: Xaa = Leu or PHe
<220> FEATURE:
<221> NAME/KEY: VARIANT
<222> LOCATION: 9
<223> OTHER INFORMATION: Xaa = Ser or Thr
<220> FEATURE:
<221> NAME/KEY: VARIANT
<222> LOCATION: 10
<223> OTHER INFORMATION: Xaa = Gly or Glu
<220> FEATURE:
<221> NAME/KEY: VARIANT
<222> LOCATION: 12
<223> OTHER INFORMATION: Xaa = Gln or Leu
<220> FEATURE:
<221> NAME/KEY: VARIANT
<222> LOCATION: 13
<223> OTHER INFORMATION: Xaa = Lys or Arg
<220> FEATURE:
<221> NAME/KEY: VARIANT
<222> LOCATION: 17
<223> OTHER INFORMATION: Xaa = Thr, Ala, or Ser

<400> SEQUENCE: 54

Xaa Ser Xaa Gln Xaa Leu Xaa Asn Xaa Xaa Asn Xaa Xaa Asn Tyr Leu
1               5                   10                  15

Xaa
```

```
<210> SEQ ID NO 55
<211> LENGTH: 7
<212> TYPE: PRT
<213> ORGANISM: Artificial Sequence
<220> FEATURE:
<223> OTHER INFORMATION: Synthetic Construct

<400> SEQUENCE: 55

Trp Ala Ser Thr Arg Glu Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Trp Ala Ser Thr Arg Asp Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Trp Thr Ser Thr Arg Glu Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala or Thr
<220> FEATURE:
<221> NAME/KEY: VARIANT
<222> LOCATION: 6
<223> OTHER INFORMATION: Xaa = Glu or Asp

<400> SEQUENCE: 58

Trp Xaa Ser Thr Arg Xaa Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Asn Asp Tyr Phe Tyr Pro Leu Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 60

Gln Asn Gly Tyr Ser Tyr Pro Leu Thr
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Asp Gly Tyr Phe Tyr Pro Phe Pro
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Gln Asn Asp Phe Ile Tyr Pro Phe Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Gln Asn Asn Tyr Phe Tyr Pro Phe Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Gln Asn Asp Tyr Ser Tyr Pro Leu Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Gln Asn Ala Tyr Ser Tyr Pro Leu Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 66

Gln Asn Ala Tyr Ser Phe Pro Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Gln Asn Asp Tyr Ile Tyr Pro Leu Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gln Asn Asn Tyr Tyr Tyr Pro Leu Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Gln Asn Asn Tyr Ile Tyr Pro Phe Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Gln Asn Asp Tyr Tyr Tyr Pro Phe Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Asn or Asp
<220> FEATURE:
<221> NAME/KEY: VARIANT
<222> LOCATION: 3
<223> OTHER INFORMATION: Xaa = Asp, Gly, Asn, or Ala
<220> FEATURE:
<221> NAME/KEY: VARIANT
<222> LOCATION: 4
<223> OTHER INFORMATION: Xaa = Tyr or Phe
<220> FEATURE:
<221> NAME/KEY: VARIANT
<222> LOCATION: 5
```

<223> OTHER INFORMATION: Xaa = Phe, Ser, Ile, or Tyr
<220> FEATURE:
<221> NAME/KEY: VARIANT
<222> LOCATION: 6
<223> OTHER INFORMATION: Xaa = Tyr or Phe
<220> FEATURE:
<221> NAME/KEY: VARIANT
<222> LOCATION: 8
<223> OTHER INFORMATION: Xaa = Leu or Phe
<220> FEATURE:
<221> NAME/KEY: VARIANT
<222> LOCATION: 9
<223> OTHER INFORMATION: Xaa = Thr or Phe

<400> SEQUENCE: 71

Gln Xaa Xaa Xaa Xaa Xaa Pro Xaa Xaa
1               5

<210> SEQ ID NO 72
<211> LENGTH: 118
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met Phe Trp Val Arg Gln Ala Pro Glu Lys Gly Leu Glu Trp Val
        35                  40                  45

Gly Tyr Ile Ser Ser Gly Ser Ser Asn Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ile Ala Arg Gly Asn Ala Met Asp Tyr Trp Gly Gln Gly Thr
            100                 105                 110

Ser Val Thr Val Ser Ser
        115

<210> SEQ ID NO 73
<211> LENGTH: 118
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Ile
        35                  40                  45

Ala Tyr Ile Asn Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Phe Tyr Cys

```
                85                  90                  95
Ala Arg Phe Ala Arg Gly Asn Val Leu Asp Tyr Trp Gly Gln Gly Thr
            100                 105                 110

Ser Val Thr Val Ser Ser
        115

<210> SEQ ID NO 74
<211> LENGTH: 118
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Gln Gln Ser Gly Pro Ala Leu Val Lys Pro Gly Ala
1               5                   10                  15

Ser Val Lys Met Ser Cys Lys Ala Ser Gly Tyr Ser Phe Thr Gly Tyr
            20                  25                  30

Asn Ile His Trp Val Lys Gln Ser His Gly Lys Ser Leu Glu Trp Ile
        35                  40                  45

Gly Tyr Ile Asp Pro Asn Asn Gly Val Thr Tyr Ser Asn Gln Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Pro Tyr Tyr Gly Asn Ser Phe Asp Tyr Trp Gly Gln Gly Thr
            100                 105                 110

Thr Leu Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Val Trp
            20                  25                  30

Ser Met Ser Trp Val Lys Gln Arg Thr Gly Gln Gly Leu Gln Trp Ile
        35                  40                  45

Gly Glu Ile Tyr Pro Lys Ser Gly Asn Thr His Tyr Asn Glu Lys Phe
    50                  55                  60

Lys Gly Lys Ala Thr Leu Thr Ala Asp Lys Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Ala Tyr Tyr Gly Asn Ser Phe Ala Tyr Trp Gly Gln Gly Thr
            100                 105                 110

Leu Val Thr Val Pro Ala
        115

<210> SEQ ID NO 76
<211> LENGTH: 118
```

```
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Ala Leu Val Lys Ser Gly Gly
1               5                   10                  15

Ser Leu Arg Leu Ser Cys Ala Ala Ser Gly Phe Thr Phe Ser Asn Asn
            20                  25                  30

Ala Met Ser Trp Ile Arg Gln Thr Pro Glu Lys Arg Leu Glu Trp Val
        35                  40                  45

Ala Thr Ile Ile Ile Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Phe Tyr Tyr Cys
                85                  90                  95

Ala Arg Gln Val Tyr Gly Asn Ser Phe Ala Tyr Trp Gly Gln Gly Thr
            100                 105                 110

Leu Val Ser Val Ser Ala
        115

<210> SEQ ID NO 77
<211> LENGTH: 118
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Ile
        35                  40                  45

Ala Tyr Ile Ser Ser Gly Ser Ser Ile Tyr Tyr Ala Asp Thr Val
    50                  55                  60

Lys Gly Arg Phe Thr Met Ser Arg Asp Asn Ala Lys Lys Thr Leu Phe
65                  70                  75                  80

Leu Gln Thr Thr Ser Leu Arg Ser Glu Asp Thr Ala Met Tyr Tyr Cys
                85                  90                  95

Ala Arg Ile Ala Arg Gly Asn Ala Met Asp Tyr Trp Gly Gln Gly Thr
            100                 105                 110

Ser Val Thr Val Thr Ser
        115

<210> SEQ ID NO 78
<211> LENGTH: 118
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Asn Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
```

```
                    20                  25                  30
Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Met
        50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Val Arg Gly Asn Ser Met Asp Tyr Trp Gly Gln Gly Thr
            100                 105                 110

Ser Val Thr Val Ser Ser
        115

<210> SEQ ID NO 79
<211> LENGTH: 118
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala His Ile Ser Ser Gly Ser Asn Ile Ile His Tyr Ala Asp Thr Leu
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Ala Arg Gly Asn Ser Met Asp Tyr Trp Gly Gln Gly Thr
            100                 105                 110

Ser Val Thr Val Ser Ser
        115

<210> SEQ ID NO 80
<211> LENGTH: 118
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Met
    50                  55                  60

Lys Gly Arg Phe Thr Ile Ser Arg Asp Asn Ala Lys Asn Thr Leu Phe
65                  70                  75                  80
```

```
Leu Gln Met Thr Ser Leu Arg Ser Glu Asp Thr Ala Met Tyr Tyr Cys
                85                  90                  95

Thr Arg Phe Ala Arg Gly Asn Thr Met Asp Tyr Trp Gly Gln Gly Thr
            100                 105                 110

Ser Val Thr Val Ser Ser
        115
```

<210> SEQ ID NO 81
<211> LENGTH: 118
<212> TYPE: PRT
<213> ORGANISM: Artificial Sequence
<220> FEATURE:
<223> OTHER INFORMATION: Synthetic Construct

<400> SEQUENCE: 81

```
Glu Val Gln Leu Val Glu Ser Gly Gly Gly Ser Val Lys Pro Gly Gly
1               5                   10                  15

Ser Arg Lys Leu Ser Cys Ala Ala Ser Gly Phe Thr Phe Ser Asp Tyr
                20                  25                  30

Gly Met His Trp Val Arg Gln Ala Pro Glu Lys Gly Leu Glu Trp Val
            35                  40                  45

Ala Tyr Ile Ser Ser Gly Ser Asn Thr Phe Tyr Tyr Thr Asp Thr Val
        50                  55                  60

Lys Gly Arg Phe Thr Ile Ser Arg Asp Asn Ala Lys Asn Thr Leu Phe
65                  70                  75                  80

Leu Gln Met Thr Gly Leu Arg Ser Glu Asp Thr Ala Met Tyr Tyr Cys
                85                  90                  95

Ala Arg Phe Thr Arg Gly Asn Ala Leu Asp Tyr Trp Gly Gln Gly Thr
            100                 105                 110

Ser Val Thr Val Ser Ser
        115
```

<210> SEQ ID NO 82
<211> LENGTH: 118
<212> TYPE: PRT
<213> ORGANISM: Artificial Sequence
<220> FEATURE:
<223> OTHER INFORMATION: Synthetic Construct

<400> SEQUENCE: 82

```
Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
                20                  25                  30

Gly Met Tyr Trp Val Arg Gln Ala Pro Glu Lys Gly Leu Glu Trp Leu
            35                  40                  45

Ala Tyr Ile Ser Ser Gly Ser Asn Thr Ile Tyr Tyr Ala Asp Thr Val
        50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ile Ala Arg Gly Asn Ala Met Asp Tyr Trp Gly Gln Gly Thr
            100                 105                 110

Ser Val Thr Val Ser Ser
        115
```

<210> SEQ ID NO 83

<211> LENGTH: 118
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Ile
        35                  40                  45

Ala His Ile Ser Ser Gly Ser Ser Thr Ile Tyr Tyr Ala Asp Thr Met
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Val Arg Gly Asn Ala Leu Asp Tyr Trp Gly Gln Gly Thr
            100                 105                 110

Ser Val Thr Val Ser Ser
        115

<210> SEQ ID NO 84
<211> LENGTH: 118
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile His Tyr Val Asp Thr Met
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Ala Arg Gly Asn Thr Leu Asp Tyr Trp Gly Gln Gly Thr
            100                 105                 110

Ser Val Thr Val Ser Ser
        115

<210> SEQ ID NO 85
<211> LENGTH: 118
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Lys Pro Gly Gly
1               5                   10                  15

```
Ser Arg Lys Leu Ser Cys Ala Val Ser Gly Phe Thr Phe Ser Asp Tyr
            20                  25                  30

Gly Met Tyr Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ile Ala Arg Gly Asn Ala Met Asp Tyr Trp Gly Gln Gly Thr
            100                 105                 110

Ser Val Thr Val Ser Ser
            115
```

<210> SEQ ID NO 86
<211> LENGTH: 118
<212> TYPE: PRT
<213> ORGANISM: Artificial Sequence
<220> FEATURE:
<223> OTHER INFORMATION: Synthetic Construct

<400> SEQUENCE: 86

```
Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Ser Phe Ser Asp Tyr
            20                  25                  30

Gly Met His Trp Val Arg Gln Ala Pro Glu Lys Gly Leu Glu Trp Val
        35                  40                  45

Ala His Ile Ser Ser Gly Ser Ser Thr Ile Tyr Tyr Ala Asp Thr Met
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Ala Arg Gly Asn Thr Met Asp Tyr Trp Gly Gln Gly Thr
            100                 105                 110

Ser Val Thr Val Ser Ser
            115
```

<210> SEQ ID NO 87
<211> LENGTH: 118
<212> TYPE: PRT
<213> ORGANISM: Artificial Sequence
<220> FEATURE:
<223> OTHER INFORMATION: Synthetic Construct

<400> SEQUENCE: 87

```
Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Pro Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80
```

Leu Gln Met Thr Ser Leu Arg Ser Glu Asp Thr Ala Met Tyr Tyr Cys
                85                  90                  95

Ala Arg Phe Ala Arg Gly Asn Ala Met Asp Tyr Trp Gly Gln Gly Thr
            100                 105                 110

Ser Val Thr Val Ser Ser
        115

<210> SEQ ID NO 88
<211> LENGTH: 118
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Met
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Val Arg Gly Asn Ser Met Asp Tyr Trp Gly Gln Gly Thr
            100                 105                 110

Ser Val Thr Val Ser Ser
        115

<210> SEQ ID NO 89
<211> LENGTH: 118
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Ile Arg Gln Thr Pro Glu Lys Arg Leu Glu Trp Val
        35                  40                  45

Ala Thr Ile Ile Ile Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Val Tyr Gly Asn Ser Phe Ala Tyr Trp Gly Gln Gly Thr
            100                 105                 110

Leu Val Thr Val Ser Ala
        115

```
<210> SEQ ID NO 90
<211> LENGTH: 118
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
                20                  25                  30

Gly Met Tyr Trp Val Arg Gln Ala Pro Glu Lys Gly Leu Glu Trp Leu
            35                  40                  45

Ala Tyr Ile Ser Ser Gly Ser Asn Asn Ile Tyr Tyr Ala Asp Thr Val
        50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ile Ala Arg Gly Asn Ala Met Asp Tyr Trp Gly Gln Gly Thr
            100                 105                 110

Ser Val Ile Val Ser Ser
        115

<210> SEQ ID NO 91
<211> LENGTH: 118
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Trp
                20                  25                  30

Ser Ile Ser Trp Val Lys Gln Arg Thr Gly Gln Gly Leu Glu Trp Ile
            35                  40                  45

Gly Glu Ile Tyr Pro Arg Ser Asp Asn Ile His Tyr Asn Glu Lys Phe
        50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Ala Tyr Tyr Gly Asn Ser Phe Ala Tyr Trp Gly Gln Gly Thr
            100                 105                 110

Leu Val Thr Val Ser Ala
        115

<210> SEQ ID NO 92
<211> LENGTH: 118
<212> TYPE: PRT
<213> ORGANISM: Artificial Sequence
<220> FEATURE:
<223> OTHER INFORMATION: Synthetic Construct

<400> SEQUENCE: 92

Glu Ile Gln Leu Gln Gln Ser Gly Ala Glu Leu Val Lys Pro Gly Thr
1               5                   10                  15
```

```
Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
         35                  40                  45

Gly Asn Ile Asn Pro Tyr Tyr Ser Asn Thr Asn Tyr Asn Gln Arg Phe
 50                      55                  60

Lys Gly Lys Ala Thr Leu Thr Val Asp Lys Ser Ser Ser Thr Ala Tyr
 65                      70                  75                  80

Met Gln Leu Asn Ser Leu Thr Ser Glu Asp Ser Ala Val Tyr Tyr Cys
                 85                  90                  95

Ala Arg His Val Arg Gly Asn Ser Phe Asp Tyr Trp Gly Gln Gly Thr
             100                 105                 110

Thr Leu Thr Val Ser Ser
             115
```

<210> SEQ ID NO 93
<211> LENGTH: 118
<212> TYPE: PRT
<213> ORGANISM: Artificial Sequence
<220> FEATURE:
<223> OTHER INFORMATION: Synthetic Construct

<400> SEQUENCE: 93

```
Glu Val Gln Leu Val Glu Ser Gly Gly Gly Leu Val Lys Pro Gly Gly
 1               5                  10                  15

Ser Arg Lys Leu Ser Cys Ala Ala Ser Gly Phe Thr Phe Ser Asp Tyr
            20                  25                  30

Gly Met Tyr Trp Val Arg Gln Ala Pro Glu Lys Gly Leu Glu Trp Val
         35                  40                  45

Ala Phe Ile Ser Ser Gly Ser Ser Thr Ile Tyr Cys Ala Asp Thr Val
 50                      55                  60

Lys Gly Arg Phe Thr Ile Ser Arg Asp Asn Ala Lys Asn Thr Leu Phe
 65                      70                  75                  80

Leu Gln Met Thr Ser Leu Arg Ser Glu Asp Thr Ala Met Tyr Tyr Cys
                 85                  90                  95

Ala Arg Ile Ala Arg Gly Asn Ala Met Asp Tyr Trp Gly Gln Gly Thr
             100                 105                 110

Ser Val Thr Val Ser Ser
             115
```

<210> SEQ ID NO 94
<211> LENGTH: 113
<212> TYPE: PRT
<213> ORGANISM: Artificial Sequence
<220> FEATURE:
<223> OTHER INFORMATION: Synthetic Construct

<400> SEQUENCE: 94

```
Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
         35                  40                  45

Pro Pro Lys Leu Leu Ile Tyr Trp Ala Ser Thr Arg Glu Ser Gly Val
 50                      55                  60

Pro Asp Arg Phe Thr Gly Ser Gly Ser Gly Thr Asp Phe Thr Leu Thr
```

```
              65                  70                  75                  80
Ile Ser Ser Val Gln Ala Glu Asp Leu Ala Ile Tyr Tyr Cys Gln Asn
                85                  90                  95

Asp Tyr Phe Tyr Pro Leu Thr Phe Gly Ala Gly Thr Lys Leu Glu Leu
            100                 105                 110

Lys

<210> SEQ ID NO 95
<211> LENGTH: 113
<212> TYPE: PRT
<213> ORGANISM: Artificial Sequence
<220> FEATURE:
<223> OTHER INFORMATION: Synthetic Construct

<400> SEQUENCE: 95

Asp Ile Val Met Thr Gln Ser Pro Ser Ser Leu Thr Val Thr Ala Gly
1               5                   10                  15

Glu Lys Val Thr Met Ser Cys Arg Ser Ser Gln Ser Leu Leu Asn Ser
            20                  25                  30

Gly Asn Gln Arg Asn Tyr Leu Thr Trp Tyr Gln Gln Lys Pro Gly His
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Gly Val Gln Ala Glu Asp Leu Ala Val Tyr Tyr Cys Gln Asn
                85                  90                  95

Gly Tyr Ser Tyr Pro Leu Thr Phe Gly Ala Gly Thr Lys Leu Glu Val
            100                 105                 110

Lys

<210> SEQ ID NO 96
<211> LENGTH: 113
<212> TYPE: PRT
<213> ORGANISM: Artificial Sequence
<220> FEATURE:
<223> OTHER INFORMATION: Synthetic Construct

<400> SEQUENCE: 96

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Leu Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Leu Tyr Phe Cys Gln Asp
                85                  90                  95

Gly Tyr Phe Tyr Pro Phe Pro Phe Gly Ser Gly Thr Lys Leu Val Ile
            100                 105                 110

Lys

<210> SEQ ID NO 97
<211> LENGTH: 113
```

```
<212> TYPE: PRT
<213> ORGANISM: Artificial Sequence
<220> FEATURE:
<223> OTHER INFORMATION: Synthetic Construct

<400> SEQUENCE: 97

Asp Ile Val Met Thr Gln Ser Pro Ser Leu Thr Val Thr Ala Gly
1               5                   10                  15

Glu Lys Ala Thr Met Ser Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Gln Ala Glu Asp Leu Ala Val Tyr Tyr Cys Gln Asn
                85                  90                  95

Asp Phe Ile Tyr Pro Phe Thr Phe Gly Ser Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic Construct

<400> SEQUENCE: 98

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Phe Tyr Pro Phe Thr Phe Gly Ser Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic Construct

<400> SEQUENCE: 99

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30
```

Gly Asn Gln Arg Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
            100                 105                 110

Lys

<210> SEQ ID NO 100
<211> LENGTH: 113
<212> TYPE: PRT
<213> ORGANISM: Artificial Sequence
<220> FEATURE:
<223> OTHER INFORMATION: Synthetic Construct

<400> SEQUENCE: 100

Asp Ile Val Met Thr Gln Ser Pro Ser Ser Leu Thr Val Thr Ala Gly
 1                5                  10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Thr Val Tyr Tyr Cys Gln Asn
                 85                  90                  95

Ala Tyr Ser Tyr Pro Leu Thr Phe Gly Ala Gly Thr Lys Leu Glu Leu
            100                 105                 110

Lys

<210> SEQ ID NO 101
<211> LENGTH: 113
<212> TYPE: PRT
<213> ORGANISM: Artificial Sequence
<220> FEATURE:
<223> OTHER INFORMATION: Synthetic Construct

<400> SEQUENCE: 101

Asp Ile Val Met Thr Gln Ser Pro Ser Ser Leu Thr Val Thr Ala Gly
 1                5                  10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Thr Val Tyr Tyr Cys Gln Asn
                 85                  90                  95

Ala Tyr Ser Phe Pro Leu Thr Phe Gly Ala Gly Thr Lys Leu Glu Leu

<210> SEQ ID NO 102
<211> LENGTH: 113
<212> TYPE: PRT
<213> ORGANISM: Artificial Sequence
<220> FEATURE:
<223> OTHER INFORMATION: Synthetic Construct

<400> SEQUENCE: 102

```
Asp Ile Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Arg Asn Tyr Leu Thr Trp Tyr Gln Arg Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Thr Phe Tyr Tyr Cys Gln Asn
                85                  90                  95
Gly Tyr Ser Tyr Pro Leu Thr Phe Gly Ala Gly Thr Lys Leu Glu Leu
            100                 105                 110
Lys
```

<210> SEQ ID NO 103
<211> LENGTH: 113
<212> TYPE: PRT
<213> ORGANISM: Artificial Sequence
<220> FEATURE:
<223> OTHER INFORMATION: Synthetic Construct

<400> SEQUENCE: 103

```
Asp Ile Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Lys Asn Tyr Leu Thr Trp Tyr Gln Lys Pro Gly Gln
        35                  40                  45
Pro Pro Lys Leu Leu Leu Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Thr Val Tyr Tyr Cys Gln Asn
                85                  90                  95
Ala Tyr Ser Tyr Pro Leu Thr Phe Gly Ala Gly Thr Lys Leu Glu Leu
            100                 105                 110
Lys
```

<210> SEQ ID NO 104
<211> LENGTH: 113
<212> TYPE: PRT
<213> ORGANISM: Artificial Sequence
<220> FEATURE:
<223> OTHER INFORMATION: Synthetic Construct

<400> SEQUENCE: 104

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Lys Pro Gly Gln
            35                  40                  45

Pro Pro Lys Leu Leu Ile Tyr Trp Ala Ser Thr Arg Glu Ser Gly Val
            50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ile Tyr Pro Leu Thr Phe Gly Ala Gly Thr Lys Leu Gly Leu
                100                 105                 110

Lys

<210> SEQ ID NO 105
<211> LENGTH: 113
<212> TYPE: PRT
<213> ORGANISM: Artificial Sequence
<220> FEATURE:
<223> OTHER INFORMATION: Synthetic Construct

<400> SEQUENCE: 105

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
                20                  25                  30

Gly Asn Gln Lys Asn Tyr Leu Thr Trp Tyr Gln Lys Pro Gly Gln
            35                  40                  45

Pro Pro Lys Leu Leu Ile Tyr Trp Ala Ser Thr Arg Glu Ser Gly Val
            50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Thr Val Tyr Tyr Cys Gln Asn
                85                  90                  95

Gly Tyr Ser Tyr Pro Leu Thr Phe Gly Ala Gly Thr Lys Leu Glu Leu
                100                 105                 110

Lys

<210> SEQ ID NO 106
<211> LENGTH: 113
<212> TYPE: PRT
<213> ORGANISM: Artificial Sequence
<220> FEATURE:
<223> OTHER INFORMATION: Synthetic Construct

<400> SEQUENCE: 106

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Thr
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
            50                  55                  60

```
Pro Asp Arg Phe Thr Gly Ser Gly Ser Gly Thr Asp Phe Thr Leu Thr
65                  70                  75                  80

Ile Ser Ser Val Gln Ala Glu Asp Leu Thr Val Tyr Tyr Cys Gln Asn
                85                  90                  95

Gly Tyr Ser Tyr Pro Leu Thr Phe Gly Ala Gly Thr Lys Leu Glu Leu
                100                 105                 110

Lys
```

<210> SEQ ID NO 107
<211> LENGTH: 113
<212> TYPE: PRT
<213> ORGANISM: Artificial Sequence
<220> FEATURE:
<223> OTHER INFORMATION: Synthetic Construct

<400> SEQUENCE: 107

```
Asp Ile Val Met Thr Gln Ser Pro Ser Ser Leu Thr Val Thr Pro Gly
1               5                   10                  15

Glu Lys Val Thr Met Ser Cys Lys Ser Ser Gln Ser Leu Phe Asn Ser
                20                  25                  30

Gly Asn Gln Arg Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Leu Thr Phe Gly Ala Gly Thr Lys Leu Glu Leu
                100                 105                 110

Lys
```

<210> SEQ ID NO 108
<211> LENGTH: 113
<212> TYPE: PRT
<213> ORGANISM: Artificial Sequence
<220> FEATURE:
<223> OTHER INFORMATION: Synthetic Construct

<400> SEQUENCE: 108

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Thr Val Tyr Tyr Cys Gln Asn
                85                  90                  95

Gly Tyr Ser Tyr Pro Leu Thr Phe Gly Ala Gly Thr Lys Leu Glu Leu
                100                 105                 110

Lys
```

<210> SEQ ID NO 109

```
<211> LENGTH: 113
<212> TYPE: PRT
<213> ORGANISM: Artificial Sequence
<220> FEATURE:
<223> OTHER INFORMATION: Synthetic Construct

<400> SEQUENCE: 109

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Tyr Tyr Pro Leu Thr Phe Gly Ala Gly Thr Asn Leu Glu Leu
                100                 105                 110

Lys

<210> SEQ ID NO 110
<211> LENGTH: 113
<212> TYPE: PRT
<213> ORGANISM: Artificial Sequence
<220> FEATURE:
<223> OTHER INFORMATION: Synthetic Construct

<400> SEQUENCE: 110

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Ser Leu Leu Asn Ser
            20                  25                  30

Gly Asn Gln Lys Asn Tyr Leu Thr Trp Tyr Gln Gln Lys Pro Arg Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Val Gln Ala Glu Asp Leu Thr Val Tyr Tyr Cys Gln Asn
                85                  90                  95

Ala Tyr Ser Tyr Pro Leu Thr Phe Gly Ala Gly Thr Lys Leu Glu Leu
                100                 105                 110

Lys

<210> SEQ ID NO 111
<211> LENGTH: 113
<212> TYPE: PRT
<213> ORGANISM: Artificial Sequence
<220> FEATURE:
<223> OTHER INFORMATION: Synthetic Construct

<400> SEQUENCE: 111

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30
```

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Ile Tyr Pro Phe Thr Phe Gly Ser Gly Thr Lys Leu Glu Ile
                100                 105                 110

Lys

<210> SEQ ID NO 112
<211> LENGTH: 113
<212> TYPE: PRT
<213> ORGANISM: Artificial Sequence
<220> FEATURE:
<223> OTHER INFORMATION: Synthetic Construct

<400> SEQUENCE: 112

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ile Tyr Pro Leu Thr Phe Gly Ala Gly Thr Lys Leu Gly Leu
                100                 105                 110

Lys

<210> SEQ ID NO 113
<211> LENGTH: 113
<212> TYPE: PRT
<213> ORGANISM: Artificial Sequence
<220> FEATURE:
<223> OTHER INFORMATION: Synthetic Construct

<400> SEQUENCE: 113

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ile Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Gln Ala Glu Asp Leu Ala Ile Tyr Tyr Cys Gln Asn
                85                  90                  95

```
Asp Tyr Tyr Tyr Pro Phe Thr Phe Gly Ser Gly Thr Lys Leu Glu Ile
            100                 105                 110

Lys

<210> SEQ ID NO 114
<211> LENGTH: 113
<212> TYPE: PRT
<213> ORGANISM: Artificial Sequence
<220> FEATURE:
<223> OTHER INFORMATION: Synthetic Construct

<400> SEQUENCE: 114

Asp Ile Val Met Thr Gln Ser Pro Ser Ser Leu Thr Val Thr Ala Gly
1               5                   10                  15

Glu Arg Val Thr Val Gly Cys Lys Ser Arg Gln Ser Leu Phe Asn Ser
            20                  25                  30

Glu Asn Gln Lys Asn Tyr Leu Ser Trp Tyr Gln Gln Lys Pro Gly Gln
        35                  40                  45

Pro Pro Lys Leu Leu Leu Tyr Trp Thr Ser Thr Arg Glu Ser Gly Val
    50                  55                  60

Pro Glu Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Ile Tyr Pro Phe Thr Phe Gly Ser Gly Thr Lys Leu Glu Ile
            100                 105                 110

Lys

<210> SEQ ID NO 115
<211> LENGTH: 113
<212> TYPE: PRT
<213> ORGANISM: Artificial Sequence
<220> FEATURE:
<223> OTHER INFORMATION: Synthetic Construct

<400> SEQUENCE: 115

Asp Ile Val Met Thr Gln Ser Pro Ser Ser Leu Thr Val Thr Ala Gly
1               5                   10                  15

Glu Arg Val Thr Met Ser Cys Lys Ser Gln Ser Leu Leu Asn Ser
            20                  25                  30

Gly Asn Leu Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Thr Val Gln Ala Glu Asp Leu Ala Val Tyr Tyr Cys Gln Asn
                85                  90                  95

Asp Tyr Phe Tyr Pro Leu Thr Phe Gly Ala Gly Thr Lys Leu Glu Leu
            100                 105                 110

Lys

<210> SEQ ID NO 116
<211> LENGTH: 17
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 3
<223> OTHER INFORMATION: Xaa = Ser or Arg
<220> FEATURE:
<221> NAME/KEY: VARIANT
<222> LOCATION: 5
<223> OTHER INFORMATION: Xaa = Ser or Ile
<220> FEATURE:
<221> NAME/KEY: VARIANT
<222> LOCATION: 7
<223> OTHER INFORMATION: Xaa = Leu or Phe
<220> FEATURE:
<221> NAME/KEY: VARIANT
<222> LOCATION: 9
<223> OTHER INFORMATION: Xaa = Ser or Thr
<220> FEATURE:
<221> NAME/KEY: VARIANT
<222> LOCATION: 10
<223> OTHER INFORMATION: Xaa = Gly or Glu
<220> FEATURE:
<221> NAME/KEY: VARIANT
<222> LOCATION: 12
<223> OTHER INFORMATION: Xaa = Gln or Leu
<220> FEATURE:
<221> NAME/KEY: VARIANT
<222> LOCATION: 13
<223> OTHER INFORMATION: Xaa = Lys or Arg
<220> FEATURE:
<221> NAME/KEY: VARIANT
<222> LOCATION: 17
<223> OTHER INFORMATION: Xaa = Thr, Ala, or Ser

<400> SEQUENCE: 116

Lys Ser Xaa Gln Xaa Leu Xaa Asn Xaa Xaa Asn Xaa Xaa Asn Tyr Leu
1               5                   10                  15

Xaa

<210> SEQ ID NO 117
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp, Gly, Asn, or Ala
<220> FEATURE:
<221> NAME/KEY: VARIANT
<222> LOCATION: 4
<223> OTHER INFORMATION: Xaa = Tyr or Phe
<220> FEATURE:
<221> NAME/KEY: VARIANT
<222> LOCATION: 5
<223> OTHER INFORMATION: Xaa = Phe, Ser, Ile, or Tyr
<220> FEATURE:
<221> NAME/KEY: VARIANT
<222> LOCATION: 6
<223> OTHER INFORMATION: Xaa = Tyr or Phe
<220> FEATURE:
<221> NAME/KEY: VARIANT
<222> LOCATION: 8
<223> OTHER INFORMATION: Xaa = Leu or Phe

<400> SEQUENCE: 117

Gln Asn Xaa Xaa Xaa Xaa Pro Xaa Thr
1               5

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 1
<223> OTHER INFORMATION: Xaa = Tyr, Glu, Thr, His, or Asn
<220> FEATURE:
<221> NAME/KEY: VARIANT
<222> LOCATION: 3
<223> OTHER INFORMATION: Xaa = Ser, Asn, Tyr, or Ile
<220> FEATURE:
<221> NAME/KEY: VARIANT
<222> LOCATION: 4
<223> OTHER INFORMATION: Xaa = Ser, Pro, or Ile
<220> FEATURE:
<221> NAME/KEY: VARIANT
<222> LOCATION: 5
<223> OTHER INFORMATION: Xaa = Gly, Lys, Arg, or Tyr
<220> FEATURE:
<221> NAME/KEY: VARIANT
<222> LOCATION: 6
<223> OTHER INFORMATION: Xaa = Ser, Gly, or Tyr
<220> FEATURE:
<221> NAME/KEY: VARIANT
<222> LOCATION: 7
<223> OTHER INFORMATION: Xaa = Ser, Gly, Thr, Asn, or Asp
<220> FEATURE:
<221> NAME/KEY: VARIANT
<222> LOCATION: 8
<223> OTHER INFORMATION: Xaa = Asn, Thr, Tyr, Ile, or Pro
<220> FEATURE:
<221> NAME/KEY: VARIANT
<222> LOCATION: 9
<223> OTHER INFORMATION: Xaa = Ile, Thr, or Phe
<220> FEATURE:
<221> NAME/KEY: VARIANT
<222> LOCATION: 10
<223> OTHER INFORMATION: Xaa = Tyr, His, or Asn
<220> FEATURE:
<221> NAME/KEY: VARIANT
<222> LOCATION: 12
<223> OTHER INFORMATION: Xaa = Ala, Asn, Pro, Thr, or Val
<220> FEATURE:
<221> NAME/KEY: VARIANT
<222> LOCATION: 13
<223> OTHER INFORMATION: Xaa = Asp, Gln, or Glu
<220> FEATURE:
<221> NAME/KEY: VARIANT
<222> LOCATION: 14
<223> OTHER INFORMATION: Xaa = Thr, Lys, Ser, or Arg
<220> FEATURE:
<221> NAME/KEY: VARIANT
<222> LOCATION: 15
<223> OTHER INFORMATION: Xaa = Val, Phe, Met, or Leu

<400> SEQUENCE: 118

Xaa Ile Xaa Xaa Xaa Xaa Xaa Xaa Xaa Xaa Tyr Xaa Xaa Xaa Xaa Lys
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ser or Arg
<220> FEATURE:
<221> NAME/KEY: VARIANT
<222> LOCATION: 5
<223> OTHER INFORMATION: Xaa = Ser or Ile
<220> FEATURE:
<221> NAME/KEY: VARIANT
<222> LOCATION: 7
<223> OTHER INFORMATION: Xaa = Leu or Phe
```

```
<220> FEATURE:
<221> NAME/KEY: VARIANT
<222> LOCATION: 9
<223> OTHER INFORMATION: Xaa = Ser or Thr
<220> FEATURE:
<221> NAME/KEY: VARIANT
<222> LOCATION: 10
<223> OTHER INFORMATION: Xaa = Gly or Glu
<220> FEATURE:
<221> NAME/KEY: VARIANT
<222> LOCATION: 13
<223> OTHER INFORMATION: Xaa = Lys or Arg
<220> FEATURE:
<221> NAME/KEY: VARIANT
<222> LOCATION: 17
<223> OTHER INFORMATION: Xaa = Thr, Ala, or Ser

<400> SEQUENCE: 119

Lys Ser Xaa Gln Xaa Leu Xaa Asn Xaa Xaa Asn Gln Xaa Asn Tyr Leu
1               5                   10                  15

Xaa

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp, Gly, Asn, or Ala
<220> FEATURE:
<221> NAME/KEY: VARIANT
<222> LOCATION: 4
<223> OTHER INFORMATION: Xaa = Tyr or Phe
<220> FEATURE:
<221> NAME/KEY: VARIANT
<222> LOCATION: 5
<223> OTHER INFORMATION: Xaa = Phe, Ser, Ile or Tyr
<220> FEATURE:
<221> NAME/KEY: VARIANT
<222> LOCATION: 6
<223> OTHER INFORMATION: Xaa = Tyr or Phe
<220> FEATURE:
<221> NAME/KEY: VARIANT
<222> LOCATION: 8
<223> OTHER INFORMATION: Xaa = Leu or Phe

<400> SEQUENCE: 120

Gln Asn Xaa Xaa Xaa Xaa Pro Xaa Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Thr or Ser
<220> FEATURE:
<221> NAME/KEY: VARIANT
<222> LOCATION: 10
<223> OTHER INFORMATION: Xaa = His or Tyr

<400> SEQUENCE: 121

Gly Phe Xaa Phe Ser Asp Tyr Gly Met Xaa
1               5                   10
```

```
<210> SEQ ID NO 122
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Tyr, His, or Phe
<220> FEATURE:
<221> NAME/KEY: VARIANT
<222> LOCATION: 8
<223> OTHER INFORMATION: Xaa = Ser or Thr
<220> FEATURE:
<221> NAME/KEY: VARIANT
<222> LOCATION: 11
<223> OTHER INFORMATION: Xaa = Tyr or Cys
<220> FEATURE:
<221> NAME/KEY: VARIANT
<222> LOCATION: 15
<223> OTHER INFORMATION: Xaa = Val or Met

<400> SEQUENCE: 122

Xaa Ile Ser Ser Gly Ser Ser Xaa Ile Tyr Xaa Ala Asp Thr Xaa Lys
1               5                   10                  15

Gly

<210> SEQ ID NO 123
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ile or Phe
<220> FEATURE:
<221> NAME/KEY: VARIANT
<222> LOCATION: 6
<223> OTHER INFORMATION: Xaa = Thr or Ala

<400> SEQUENCE: 123

Xaa Ala Arg Gly Asn Xaa Met Asp Tyr
1               5

<210> SEQ ID NO 124
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 12
<223> OTHER INFORMATION: Xaa = Gln or Leu
<220> FEATURE:
<221> NAME/KEY: VARIANT
<222> LOCATION: 13
<223> OTHER INFORMATION: Xaa = Arg or Lys
<220> FEATURE:
<221> NAME/KEY: VARIANT
<222> LOCATION: 17
<223> OTHER INFORMATION: Xaa = Thr or Ala

<400> SEQUENCE: 124

Lys Ser Ser Gln Ser Leu Leu Asn Ser Gly Asn Xaa Xaa Asn Tyr Leu
1               5                   10                  15

Xaa
```

-continued

```
<210> SEQ ID NO 125
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Gly or Asp
<220> FEATURE:
<221> NAME/KEY: VARIANT
<222> LOCATION: 5
<223> OTHER INFORMATION: Xaa = Ser or Phe

<400> SEQUENCE: 125

Gln Asn Xaa Tyr Xaa Tyr Pro Leu Thr
1               5

<210> SEQ ID NO 126
<211> LENGTH: 261
<212> TYPE: PRT
<213> ORGANISM: Artificial Sequence
<220> FEATURE:
<223> OTHER INFORMATION: Synthetic Construct

<400> SEQUENCE: 126

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
```

<210> SEQ ID NO 127
<211> LENGTH: 261
<212> TYPE: PRT
<213> ORGANISM: Artificial Sequence
<220> FEATURE:
<223> OTHER INFORMATION: Synthetic Construct

<400> SEQUENCE: 127

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Gly Tyr Thr Phe Ile Ser Tyr Leu Ile His
1               5                   10

<210> SEQ ID NO 129
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 129

Tyr Ile Asn Pro Tyr Asn Asp Gly Thr Lys Tyr Asn Glu Lys Phe Lys
1               5                   10                  15
Gly

<210> SEQ ID NO 130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 130

Trp Ala Ser Ile Arg Ala Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic Construct

<400> SEQUENCE: 131

Leu Asn Asp Tyr Ser Phe Pro Leu Thr
1               5

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

<400> SEQUENCE: 132

Gly Tyr Thr Phe Thr Asn Tyr Val Met His
1               5                   10

<210> SEQ ID NO 133
<211> LENGTH: 17
<212> TYPE: PRT
<213> ORGANISM: Artificial Sequence
<220> FEATURE:
<223> OTHER INFORMATION: Synthetic Construct

<400> SEQUENCE: 133

Tyr Ile Asn Pro Phe Asp Asp Gly Thr Lys Tyr Asn Glu Lys Phe Lys
1               5                   10                  15
Gly

<210> SEQ ID NO 134
<211> LENGTH: 7
<212> TYPE: PRT
<213> ORGANISM: Artificial Sequence
<220> FEATURE:
<223> OTHER INFORMATION: Synthetic Construct

<400> SEQUENCE: 134

Trp Ala Ser Thr Arg Asp Ser
1               5
```

-continued

```
<210> SEQ ID NO 135
<211> LENGTH: 112
<212> TYPE: PRT
<213> ORGANISM: Artificial Sequence
<220> FEATURE:
<223> OTHER INFORMATION: Synthetic Construct

<400> SEQUENCE: 135

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ile Ser Tyr
            20                  25                  30

Leu Ile His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Ser
65                  70                  75                  80

Met Glu Phe Ser Ser Leu Thr Ser Glu Asp Ser Ala Val Tyr Tyr Cys
                85                  90                  95

Thr Arg Gly Asp Phe Trp Gly Gln Gly Thr Thr Leu Thr Val Ser Ser
            100                 105                 110

<210> SEQ ID NO 136
<211> LENGTH: 112
<212> TYPE: PRT
<213> ORGANISM: Artificial Sequence
<220> FEATURE:
<223> OTHER INFORMATION: Synthetic Construct

<400> SEQUENCE: 136

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Met His Trp Val Lys Gln Lys Pro Gly Gln Gly Leu Glu Trp Ile
        35                  40                  45

Gly Tyr Ile Asn Pro Phe Asp Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Gly Asp Tyr Trp Gly Gln Gly Thr Thr Leu Thr Val Ser Ser
            100                 105                 110

<210> SEQ ID NO 137
<211> LENGTH: 113
<212> TYPE: PRT
<213> ORGANISM: Artificial Sequence
<220> FEATURE:
<223> OTHER INFORMATION: Synthetic Construct

<400> SEQUENCE: 137

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
```

```
                35                  40                  45
Pro Pro Lys Leu Leu Ile Tyr Trp Ala Ser Ile Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Leu Tyr Tyr Cys Leu Asn
                85                  90                  95

Asp Tyr Ser Phe Pro Leu Thr Phe Gly Ala Gly Thr Lys Leu Glu Leu
                100                 105                 110

Lys

<210> SEQ ID NO 138
<211> LENGTH: 113
<212> TYPE: PRT
<213> ORGANISM: Artificial Sequence
<220> FEATURE:
<223> OTHER INFORMATION: Synthetic Construct

<400> SEQUENCE: 138

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Asp Ser Gly Val
    50                  55                  60

Pro Asp Arg Phe Arg Gly Ser Gly Ser Gly Thr Asp Phe Thr Leu Thr
65                  70                  75                  80

Ile Ser Ser Val Gln Ala Glu Asp Leu Ala Val Tyr Tyr Cys Leu Asn
                85                  90                  95

Asp Tyr Ser Phe Pro Leu Thr Phe Gly Ala Gly Thr Lys Leu Glu Leu
                100                 105                 110

Lys

<210> SEQ ID NO 139
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Thr or Ile
<220> FEATURE:
<221> NAME/KEY: VARIANT
<222> LOCATION: 6
<223> OTHER INFORMATION: Xaa = Ser or Asn
<220> FEATURE:
<221> NAME/KEY: VARIANT
<222> LOCATION: 8
<223> OTHER INFORMATION: Xaa = Leu or Val
<220> FEATURE:
<221> NAME/KEY: VARIANT
<222> LOCATION: 9
<223> OTHER INFORMATION: Xaa = Ile or Met

<400> SEQUENCE: 139

Gly Tyr Thr Phe Xaa Xaa Tyr Xaa Xaa His
1               5                   10
```

```
<210> SEQ ID NO 140
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Tyr or Phe
<220> FEATURE:
<221> NAME/KEY: VARIANT
<222> LOCATION: 6
<223> OTHER INFORMATION: Xaa = Asn or Asp

<400> SEQUENCE: 140

Tyr Ile Asn Pro Xaa Xaa Asp Gly Thr Lys Tyr Asn Glu Lys Phe Lys
1               5                   10                  15
Gly

<210> SEQ ID NO 141
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Thr or Ile
<220> FEATURE:
<221> NAME/KEY: VARIANT
<222> LOCATION: 6
<223> OTHER INFORMATION: Xaa = Ala or Asp

<400> SEQUENCE: 141

Trp Ala Ser Xaa Arg Xaa Ser
1               5
```